United States Patent
Cheung et al.

(10) Patent No.: US 12,084,442 B2
(45) Date of Patent: Sep. 10, 2024

(54) NAPHTHYRIDINONE DERIVATIVES FOR THE TREATMENT OF A DISEASE OR DISORDER

(71) Applicant: Novartis AG, Basel (CH)

(72) Inventors: Atwood Kim Cheung, Arlington, MA (US); Donglei Liu, Dover, MA (US); Stefan Peukert, Arlington, MA (US); Heng Ge, Jiangsu (CN); Yu Gai, Shanghai (CN); Xingjuan Chang, Jiangsu (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 18/057,505

(22) Filed: Nov. 21, 2022

(65) Prior Publication Data
US 2023/0203032 A1 Jun. 29, 2023

Related U.S. Application Data

(60) Provisional application No. 63/282,492, filed on Nov. 23, 2021.

(51) Int. Cl.
*A61K 45/06* (2006.01)
*C07D 471/04* (2006.01)

(52) U.S. Cl.
CPC ............ *C07D 471/04* (2013.01); *A61K 45/06* (2013.01)

(58) Field of Classification Search
CPC .............................. C07D 471/04; A61K 45/06
See application file for complete search history.

(56) References Cited

FOREIGN PATENT DOCUMENTS

| WO | 2018073788 A1 | 4/2018 | |
| WO | WO2018/073788 | * 4/2018 | ........... C07D 471/04 |
| WO | 2019241311 A1 | 12/2019 | |
| WO | 2021178420 A1 | 9/2021 | |
| WO | 2022074567 A1 | 4/2022 | |

\* cited by examiner

*Primary Examiner* — Paul V Ward
(74) *Attorney, Agent, or Firm* — Timothy P. O'Dea

(57) ABSTRACT

The invention relates to a compound of formula (I):

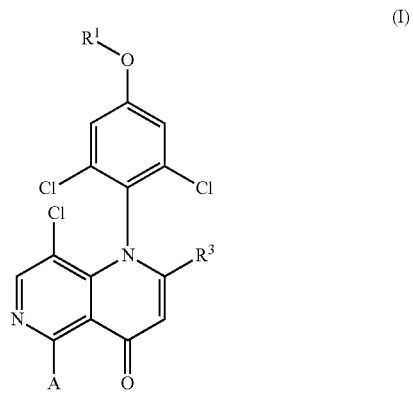

or a pharmaceutically acceptable salt thereof, wherein A, $R^1$ and $R^3$ are as described herein, as well as compositions and methods of using such compounds.

21 Claims, 31 Drawing Sheets

Figure A1-1. XRPD of Modification A-1 of Example 1
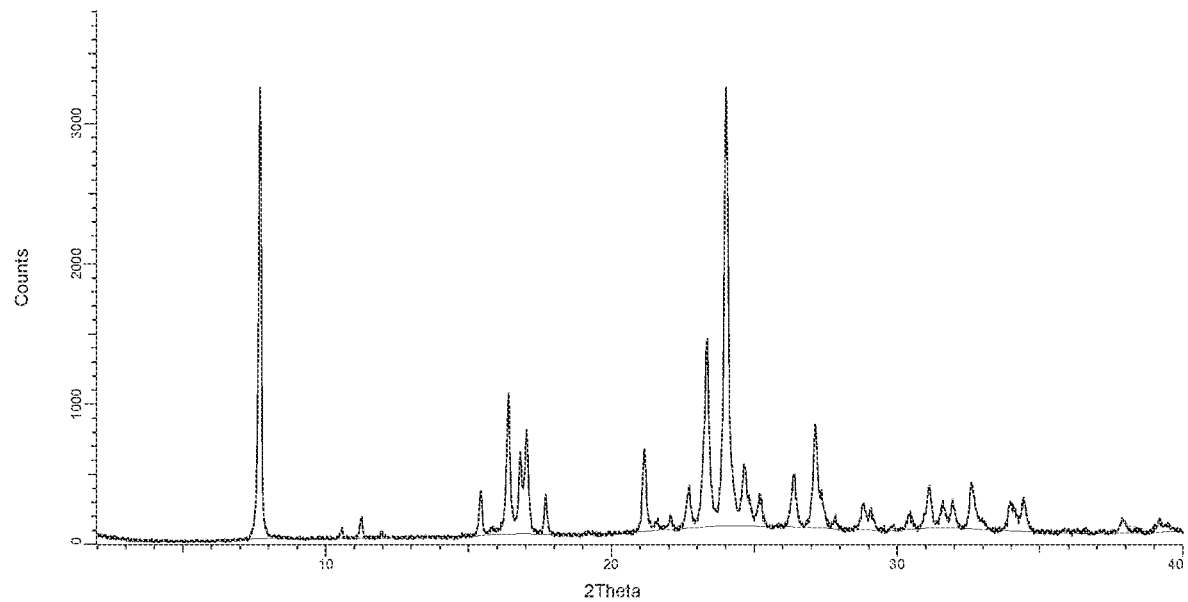
Figure A1-2. DSC of Modification A-1 of Example 1
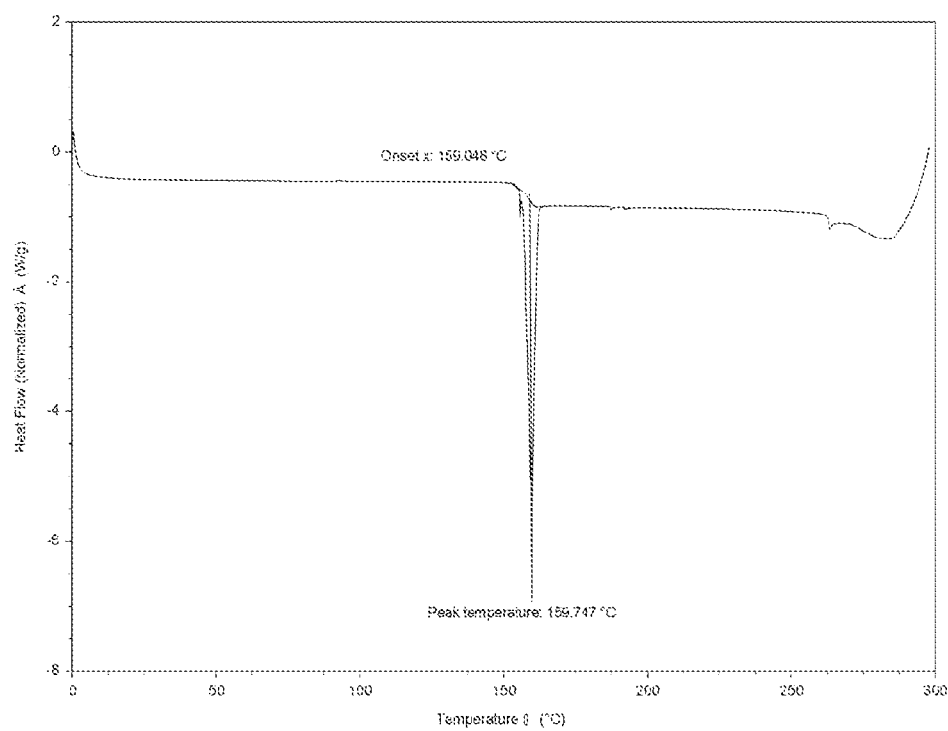

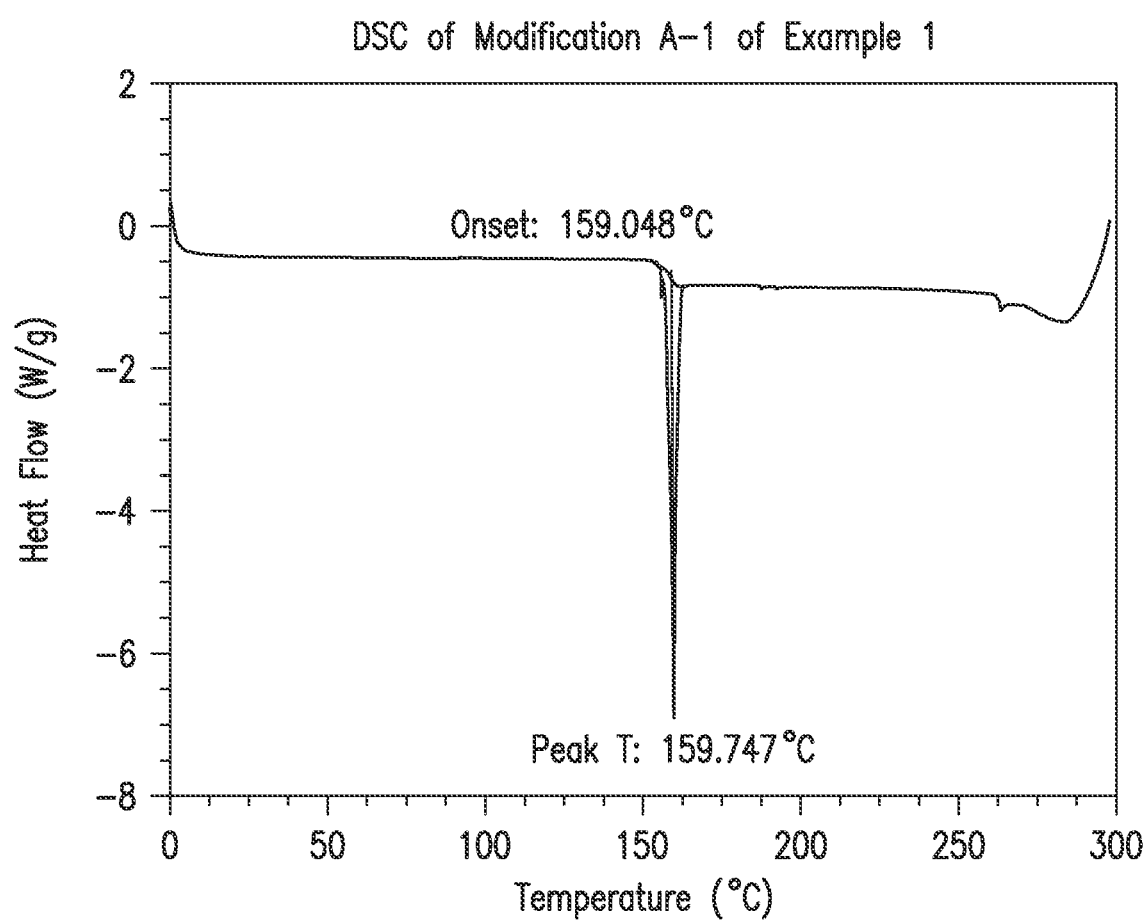
Figure A1-2

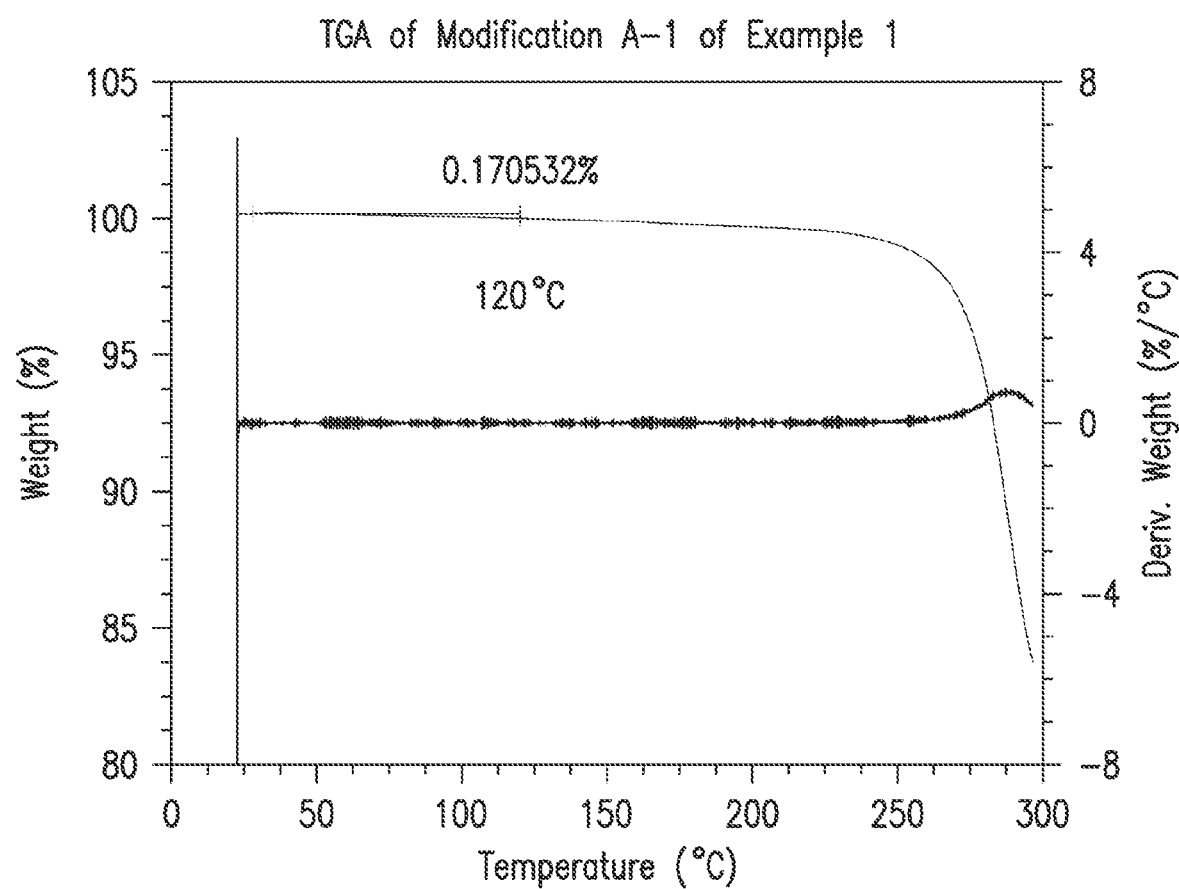
Figure A1-3

Figure A1-3. TGA of Modification A-1 of Example 1
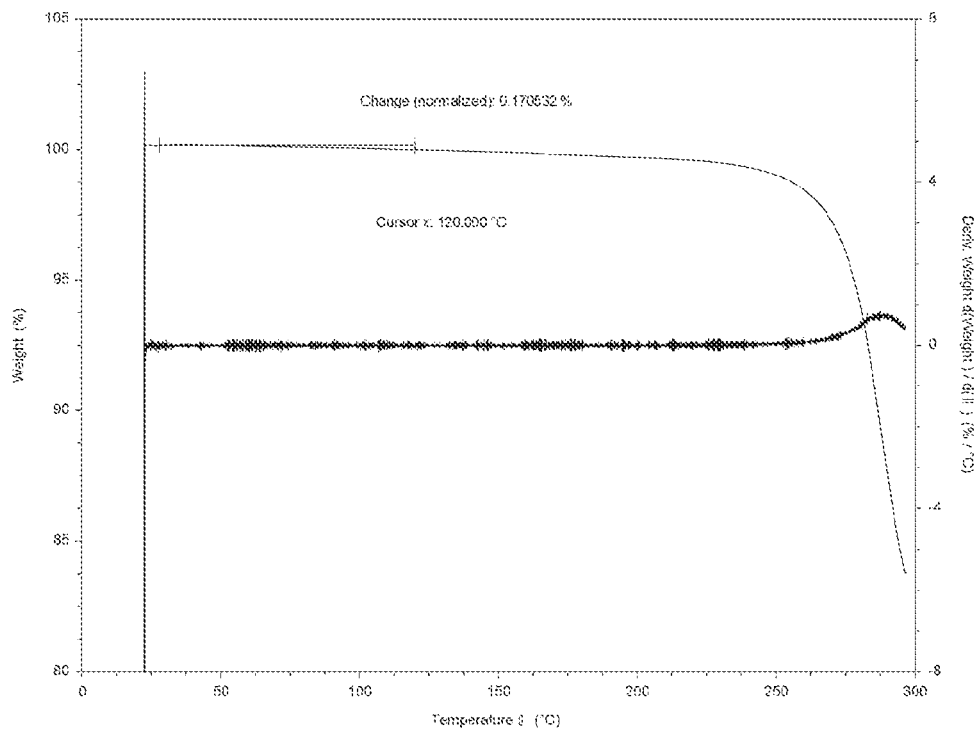
Figure A2-1. XRPD of Modification A-2 of Example 1
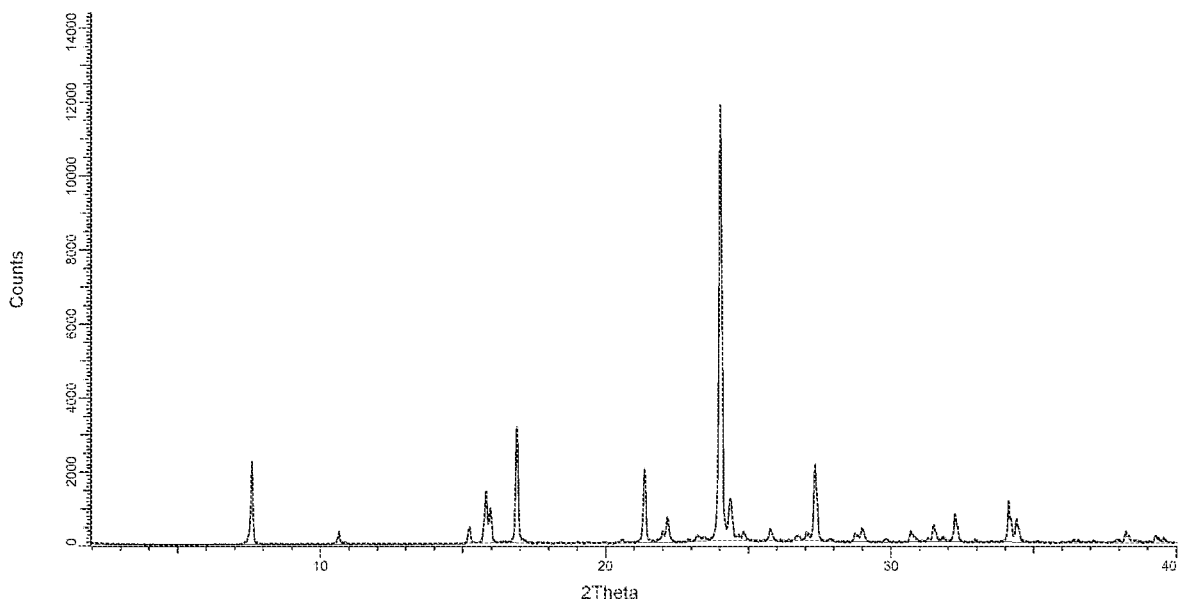

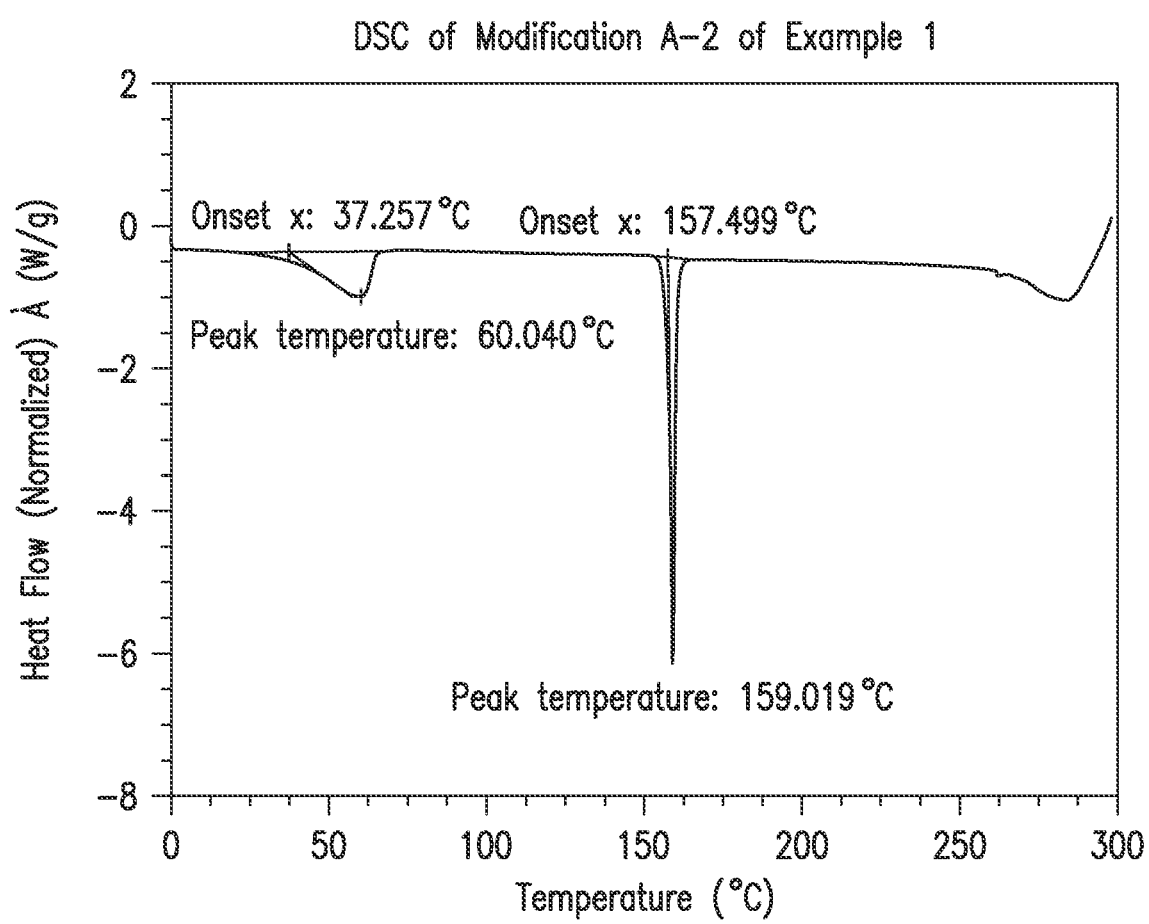
Figure A2-2

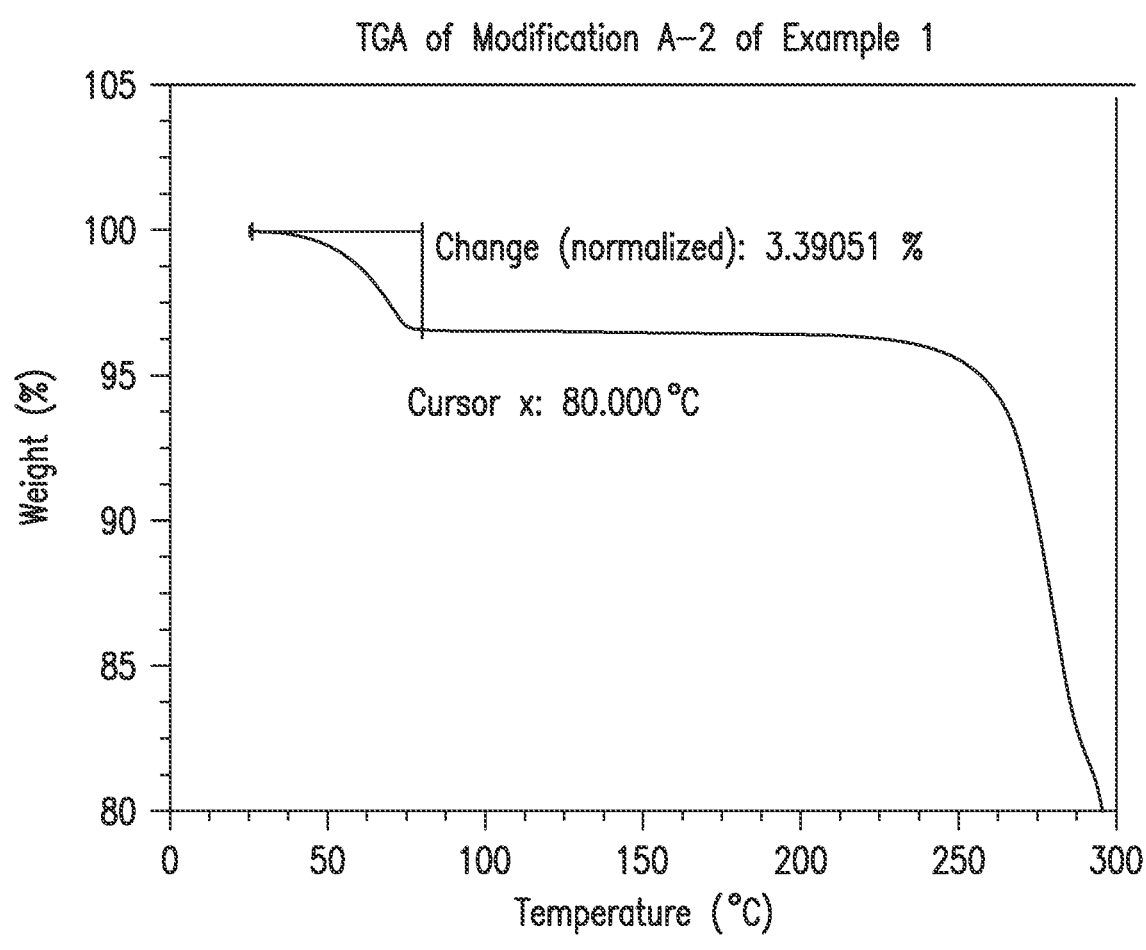
Figure A2-3

Figure A3-1. XRPD of Modification A-3 of Example 1
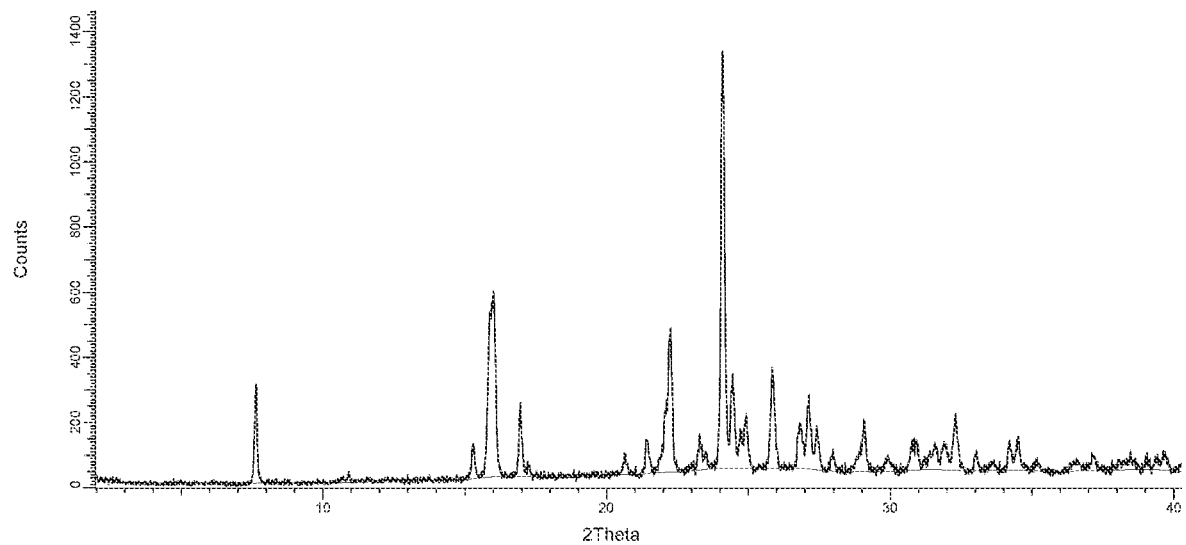
Figure A3-2. DSC of Modification A-3 of Example 1
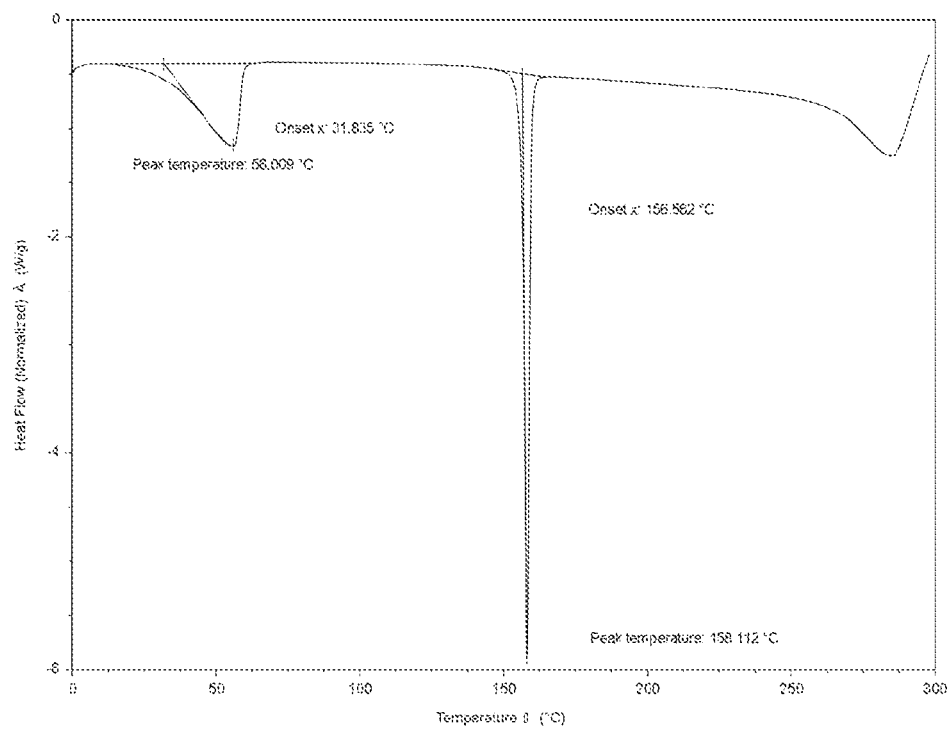

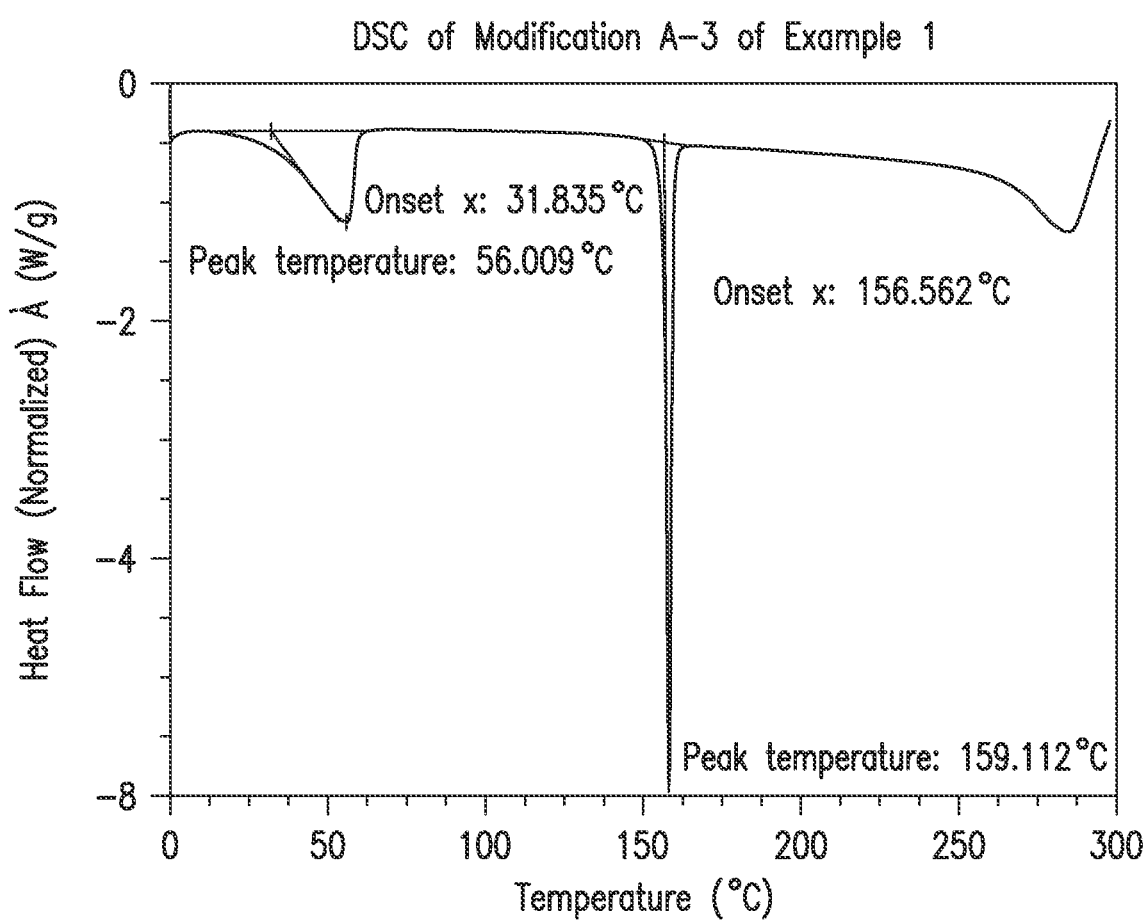
Figure A3-2

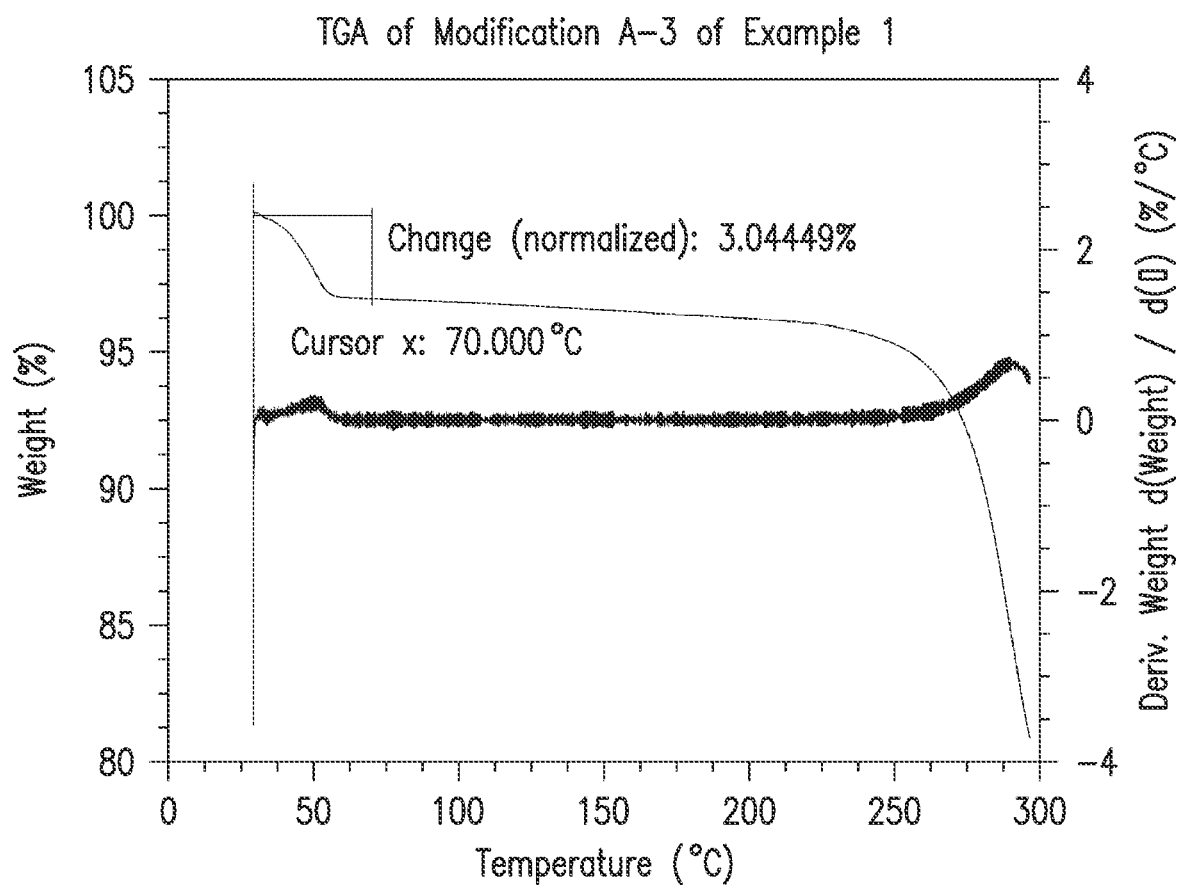
Figure A3-3

Figure A3-3. TGA of Modification A-3 of Example 1
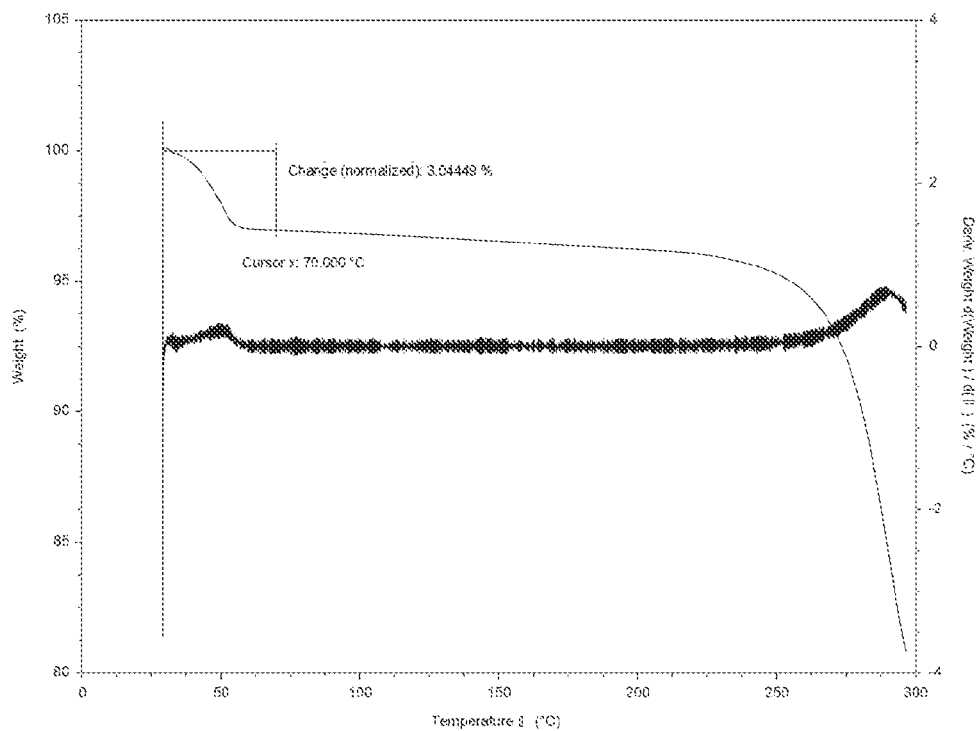
Figure A4-1. XRPD of Modification A-4 of Example 1
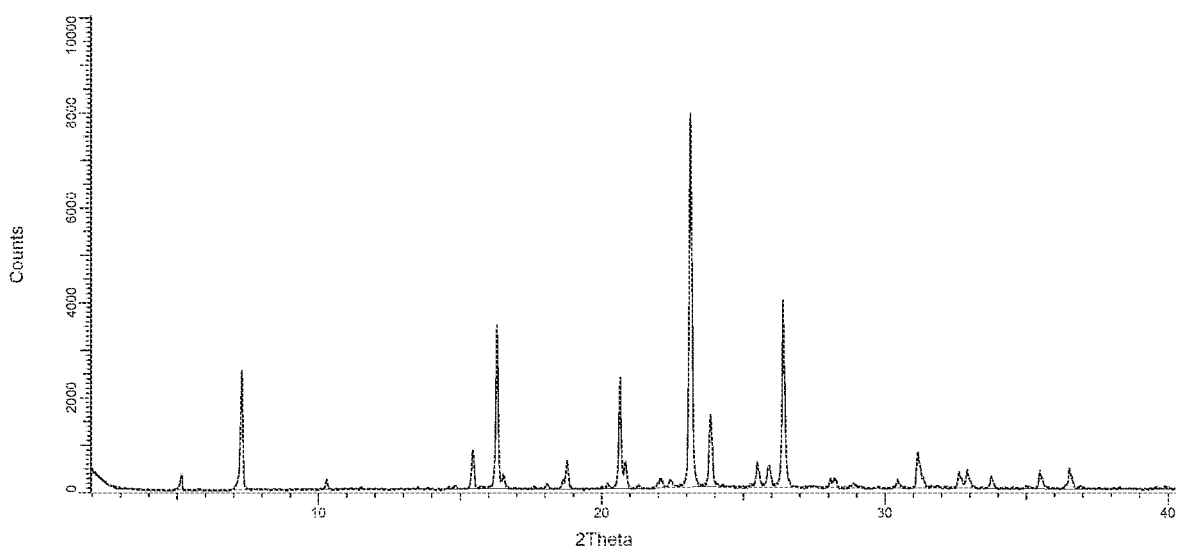

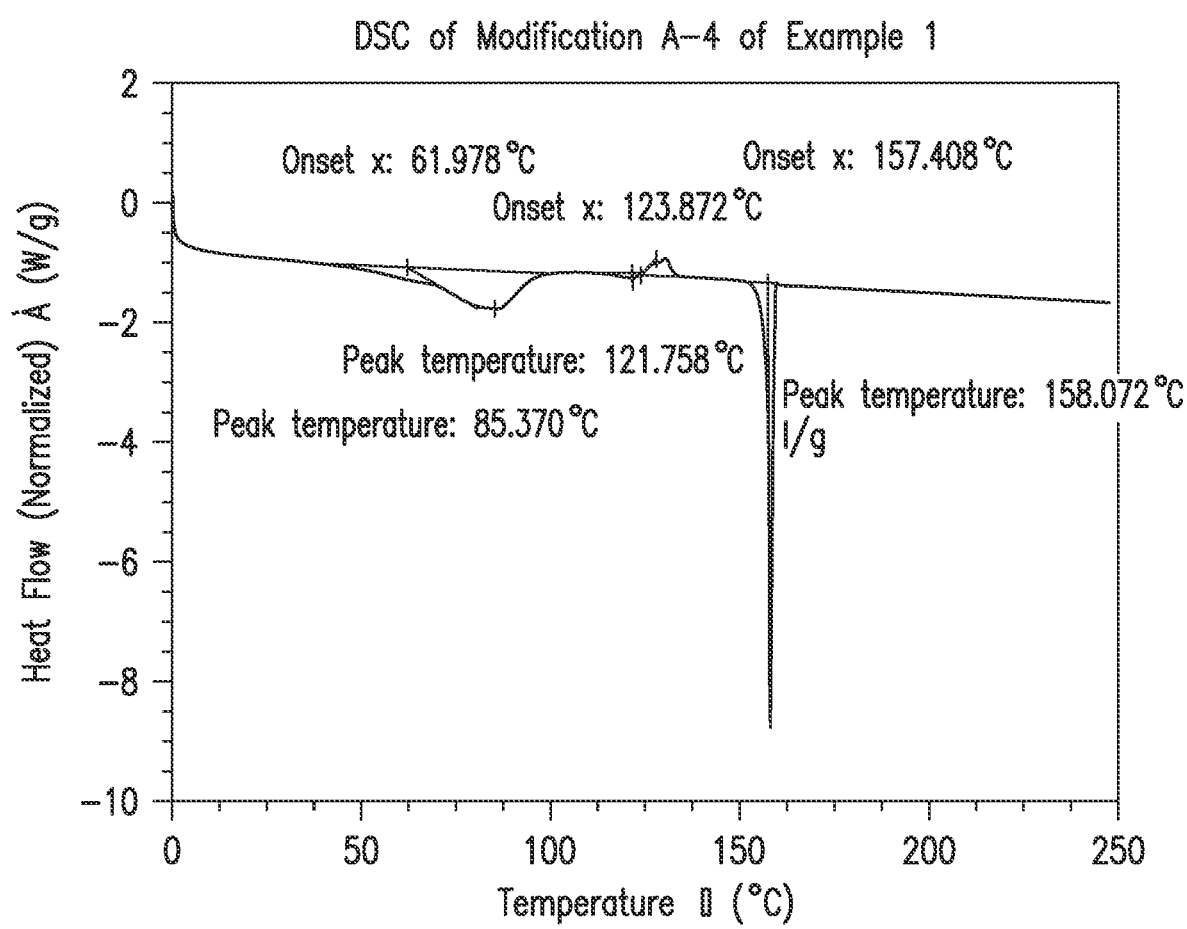
Figure A4-2

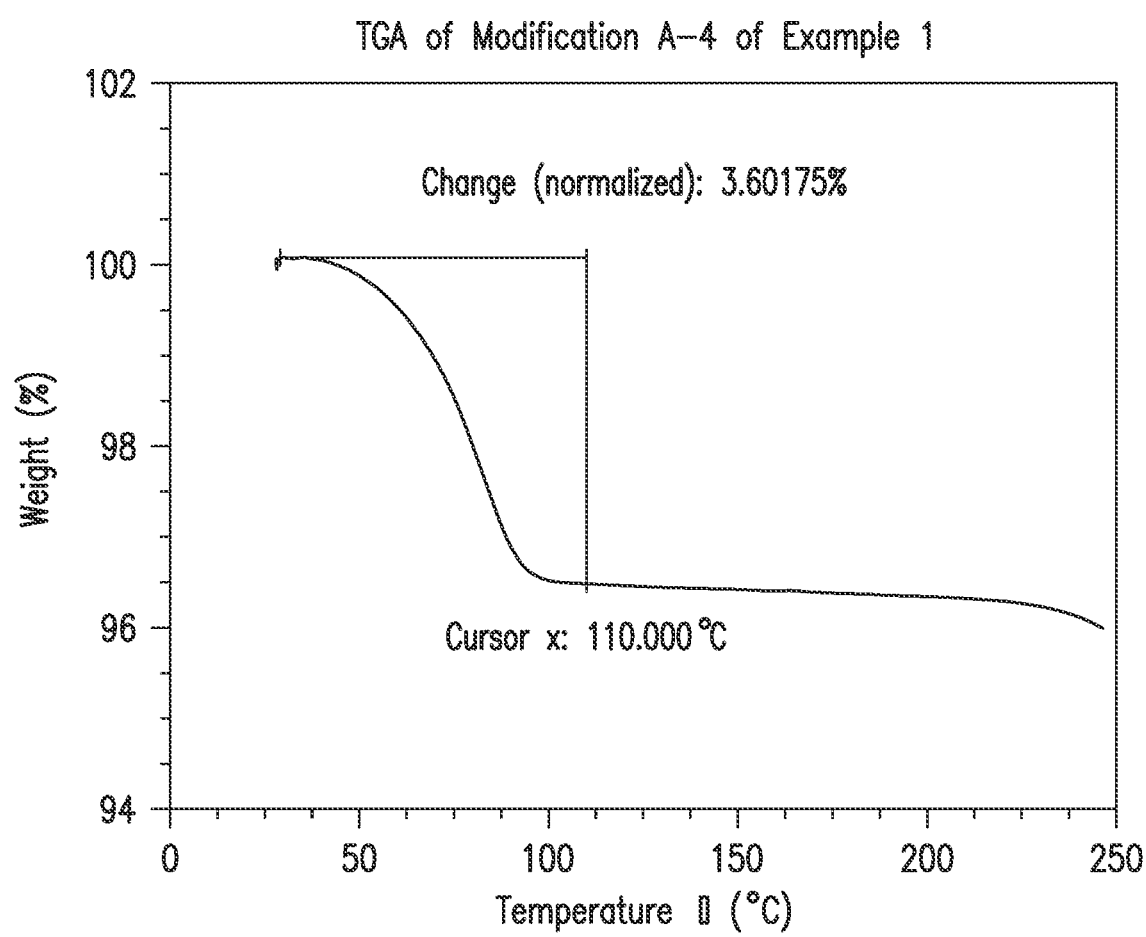
Figure A4-3

Figure A5-1. XRPD of Modification A-5 of Example 1
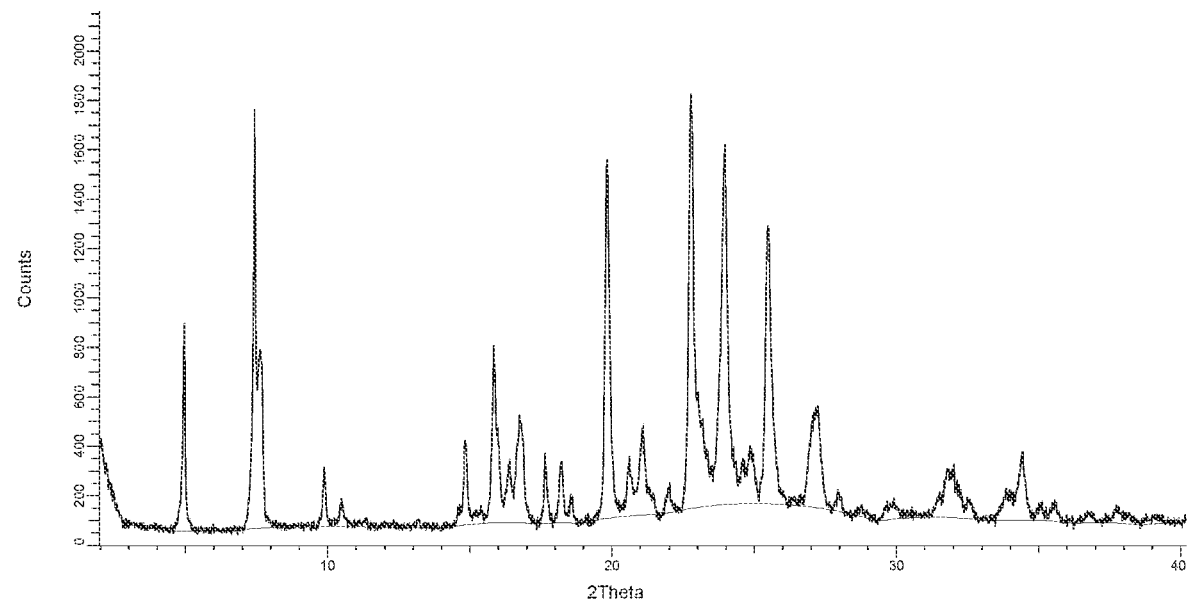
Figure A5-2. DSC of Modification A-5 of Example 1
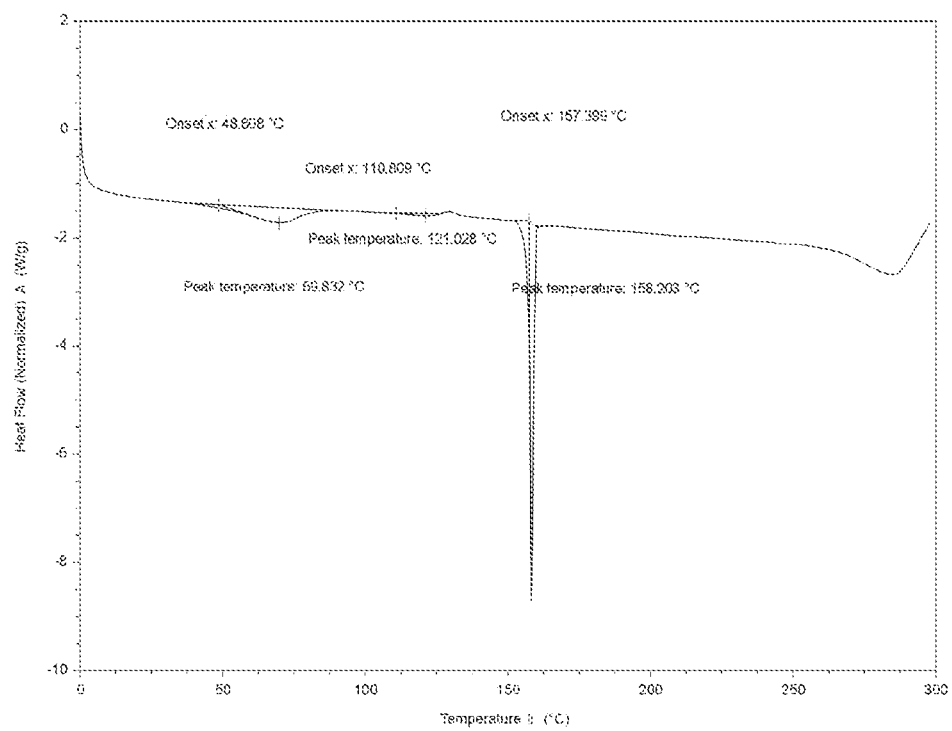

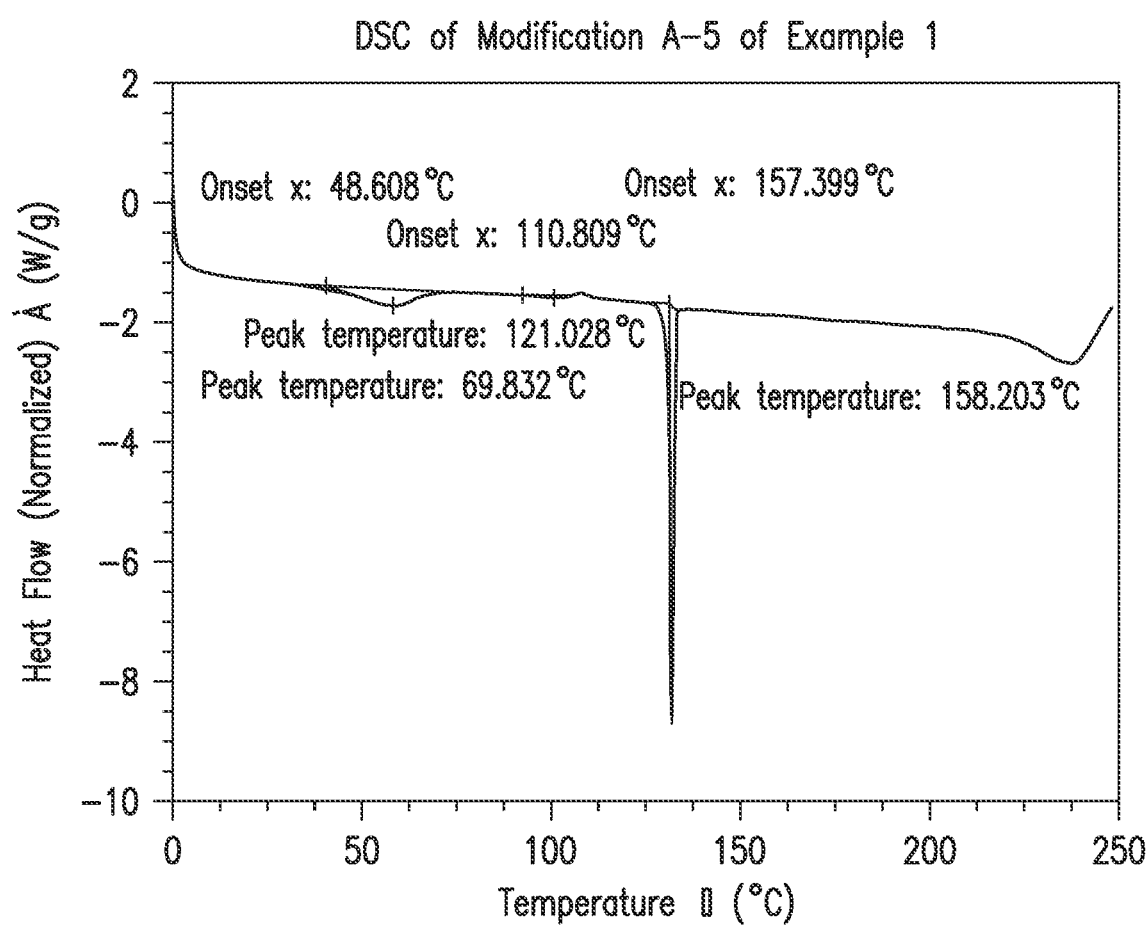
Figure A5-2

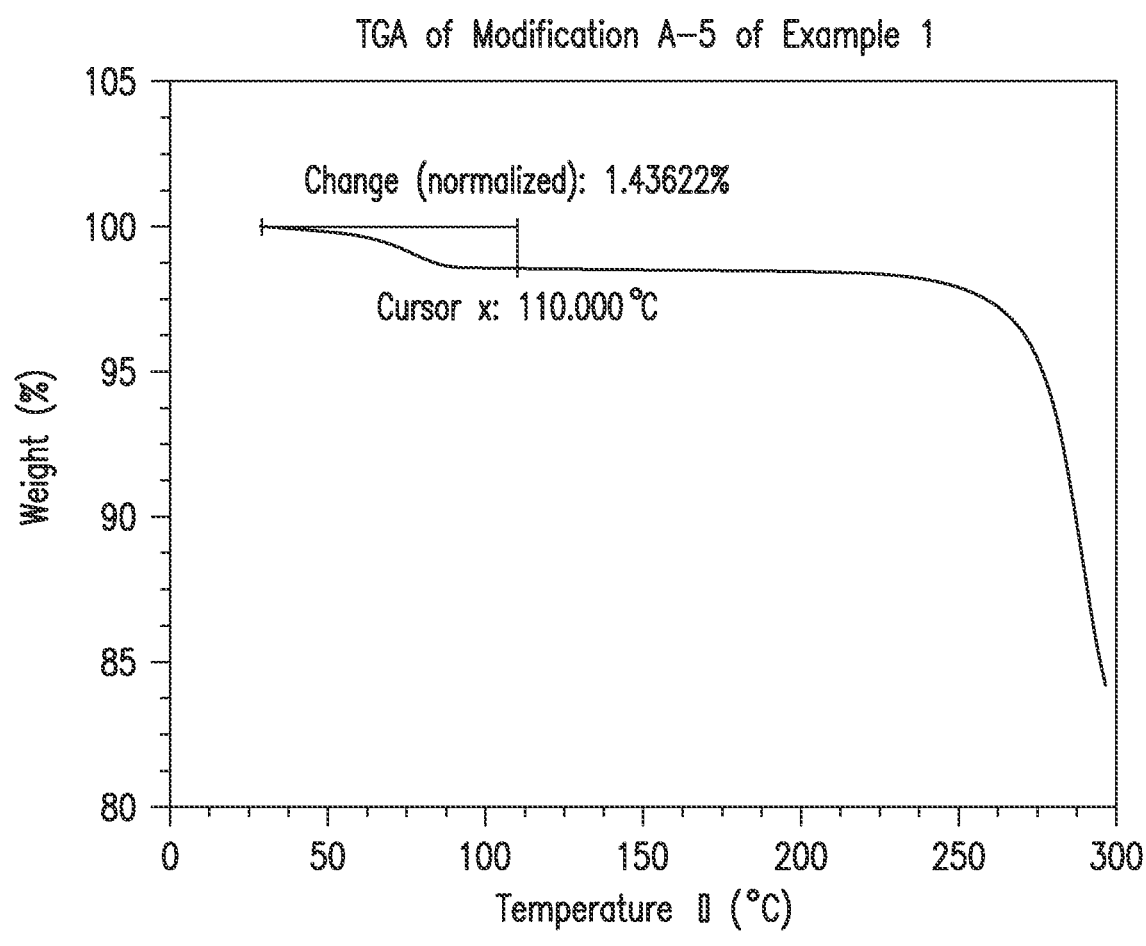
Figure A5-3

Figure A5-3. TGA of Modification A-5 of Example 1
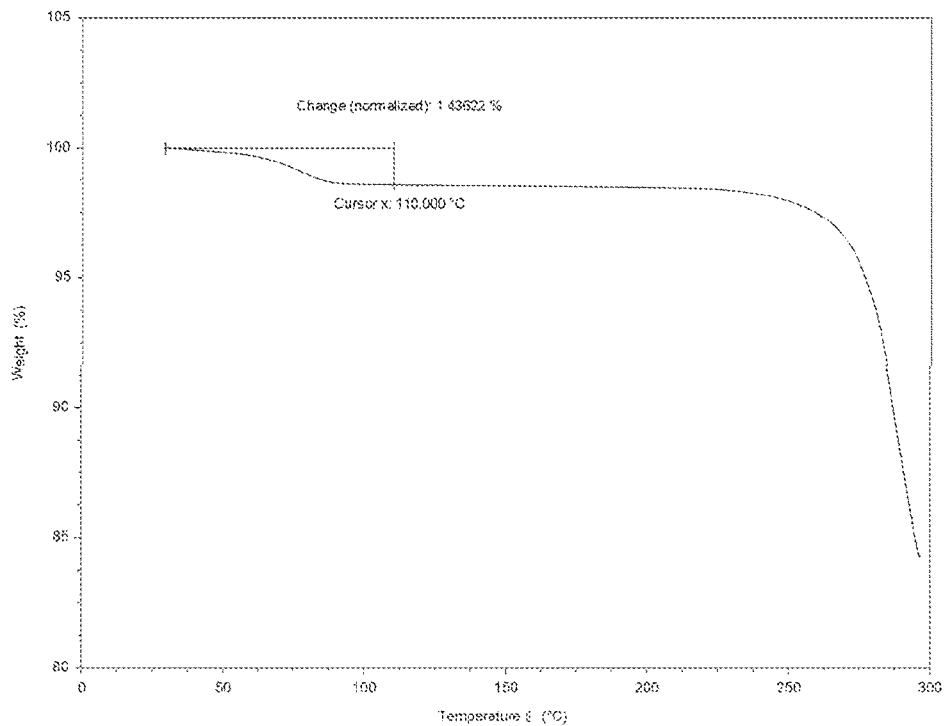
Figure A6-1. XRPD of Modification A-6 of Example 1
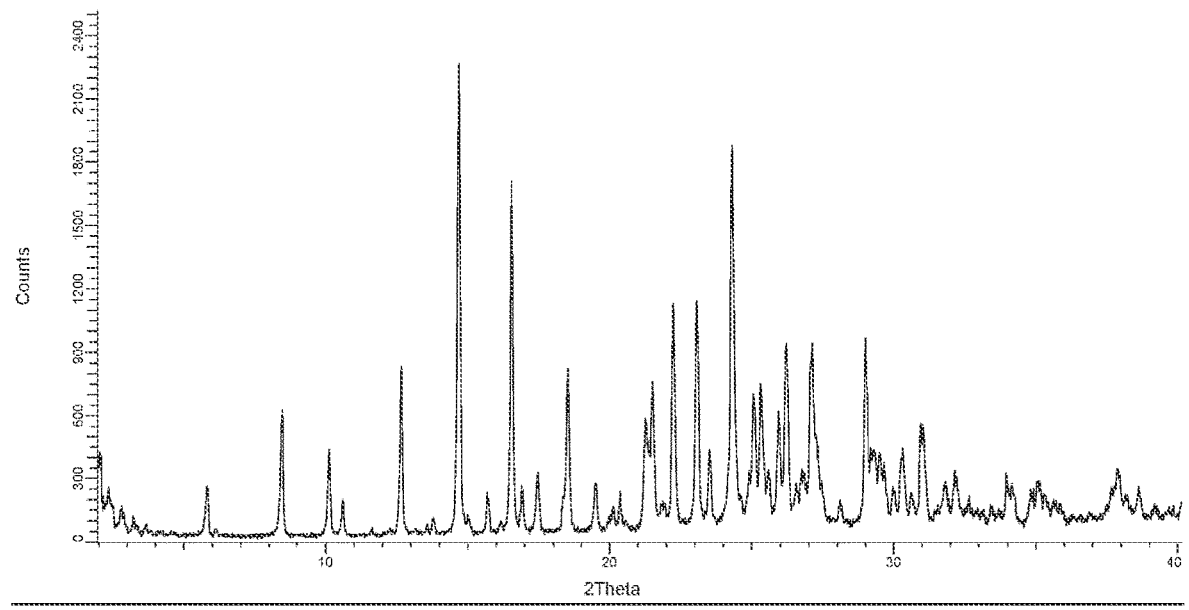

Figure A7-1. XRPD of Modification A-7 of Example 1
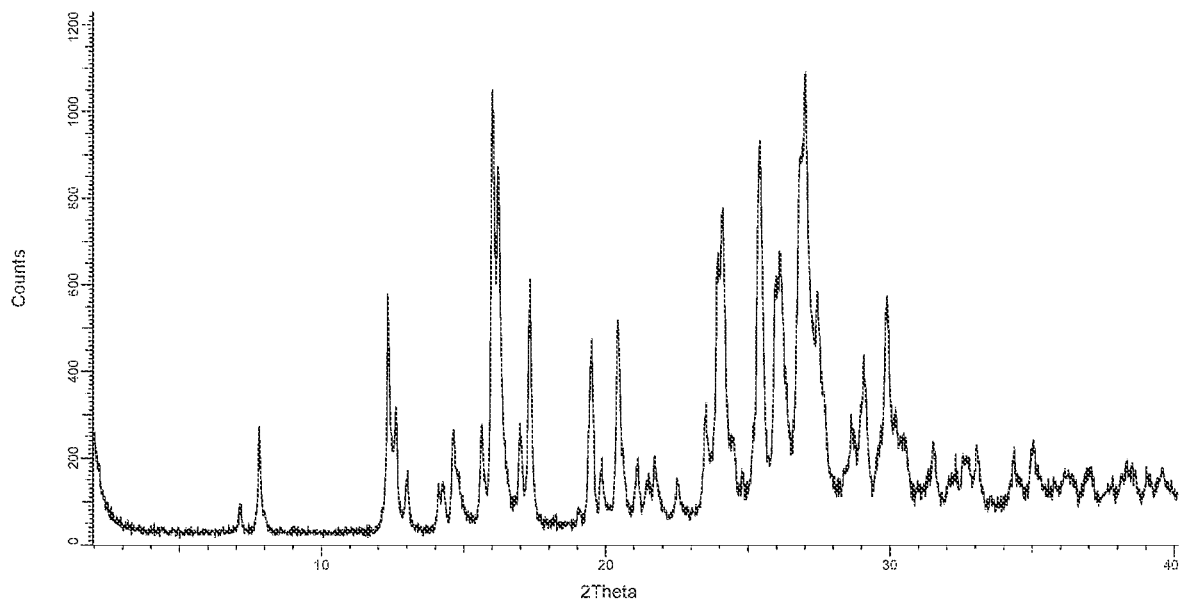
Figure A8-1. XRPD of Modification A-8 of Example 1
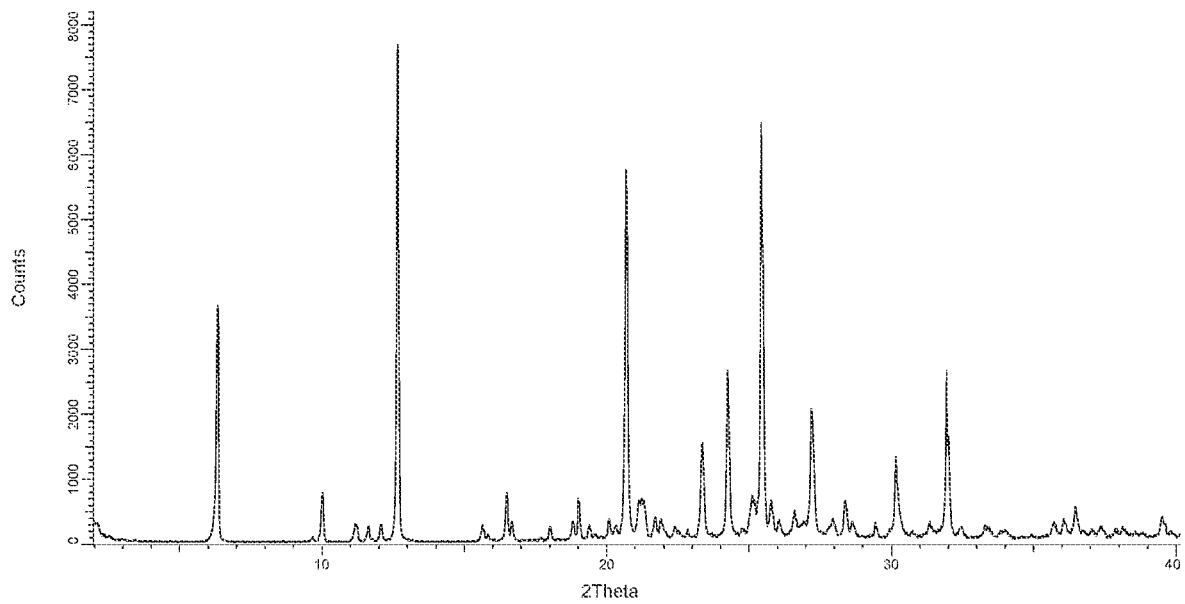

Figure A9-1. XRPD of Modification A-9 of Example 1
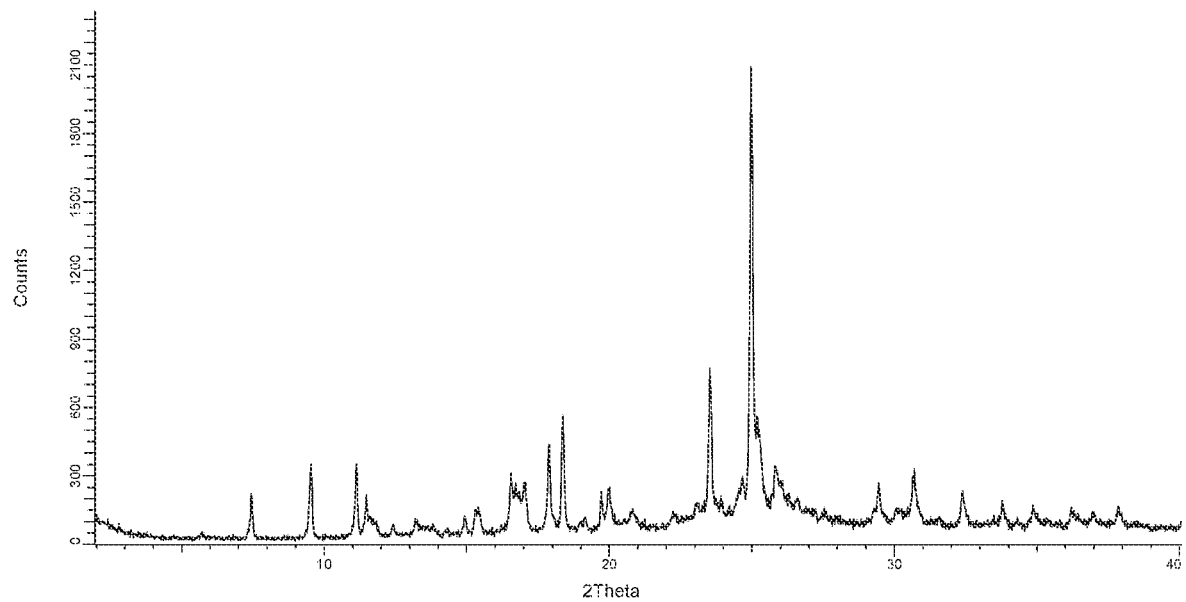
Figure A9-2. DSC of Modification A-9 of Example 1
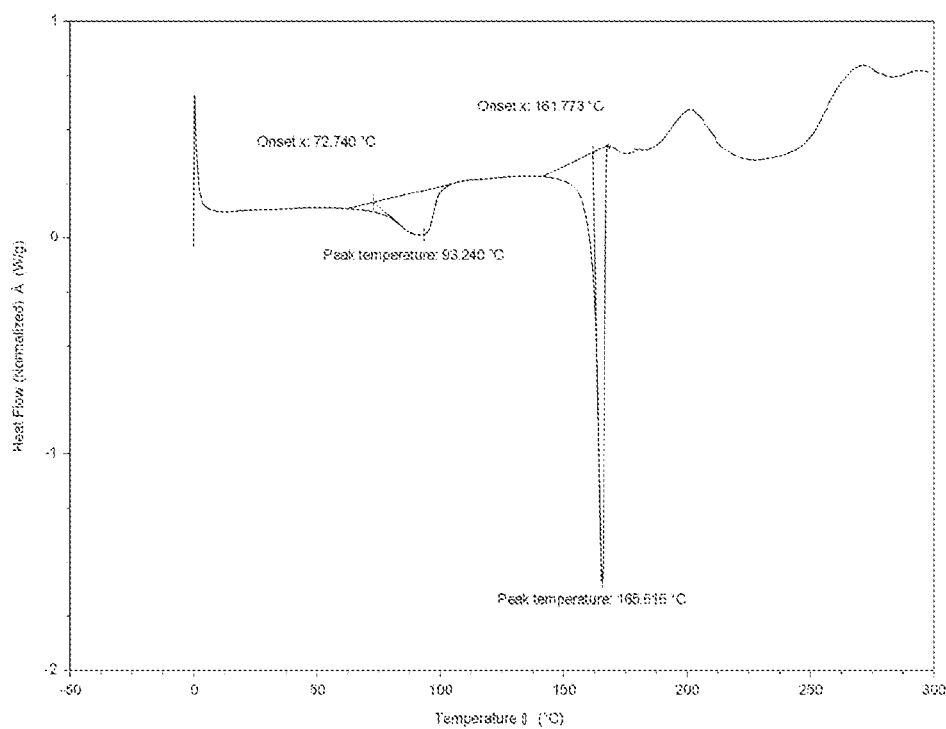

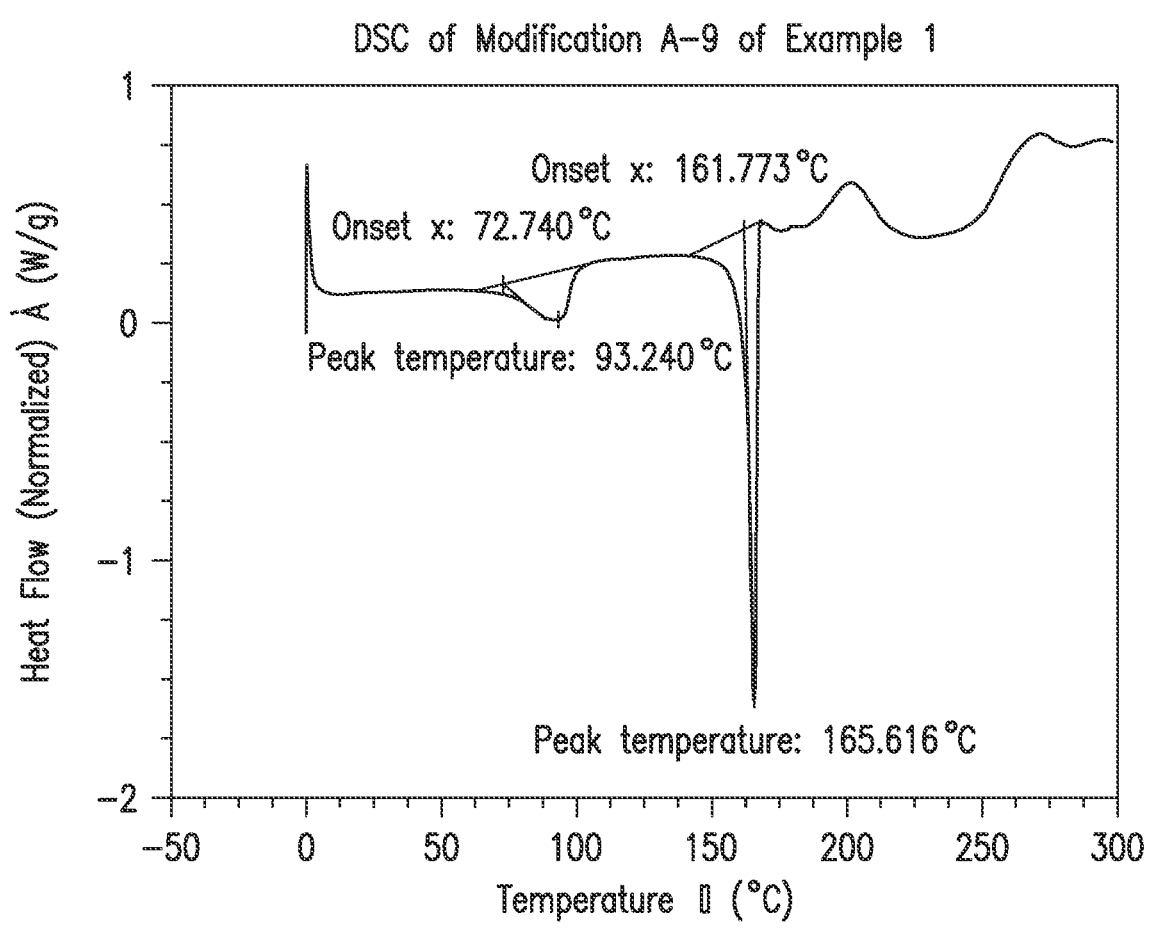
Figure A9-2

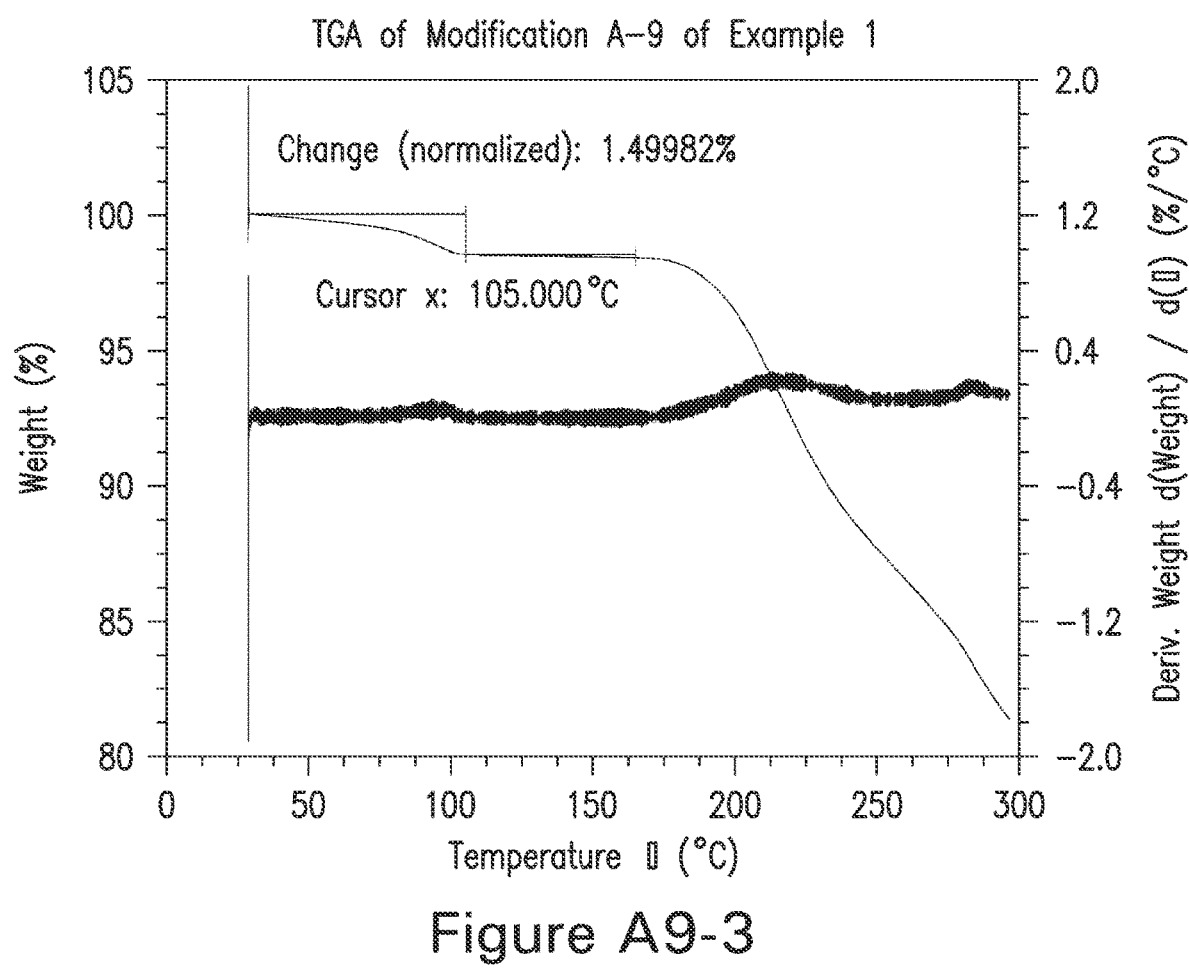
Figure A9-3

Figure A9-3. TGA of Modification A-9 of Example 1
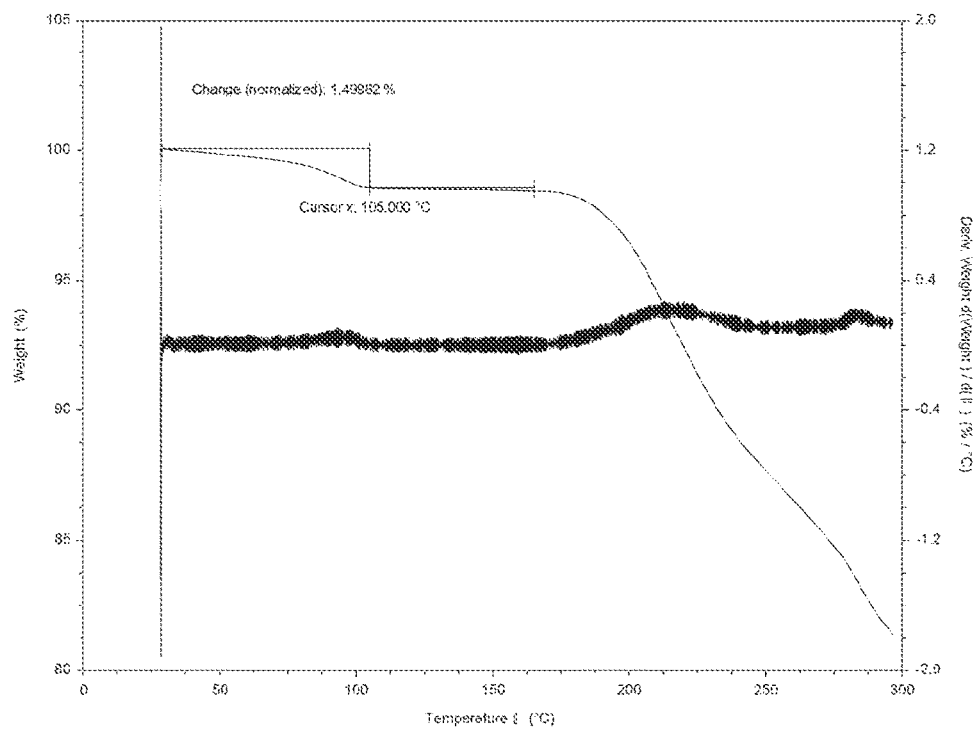
Figure A10-1. XRPD of Modification A-10 of Example 1
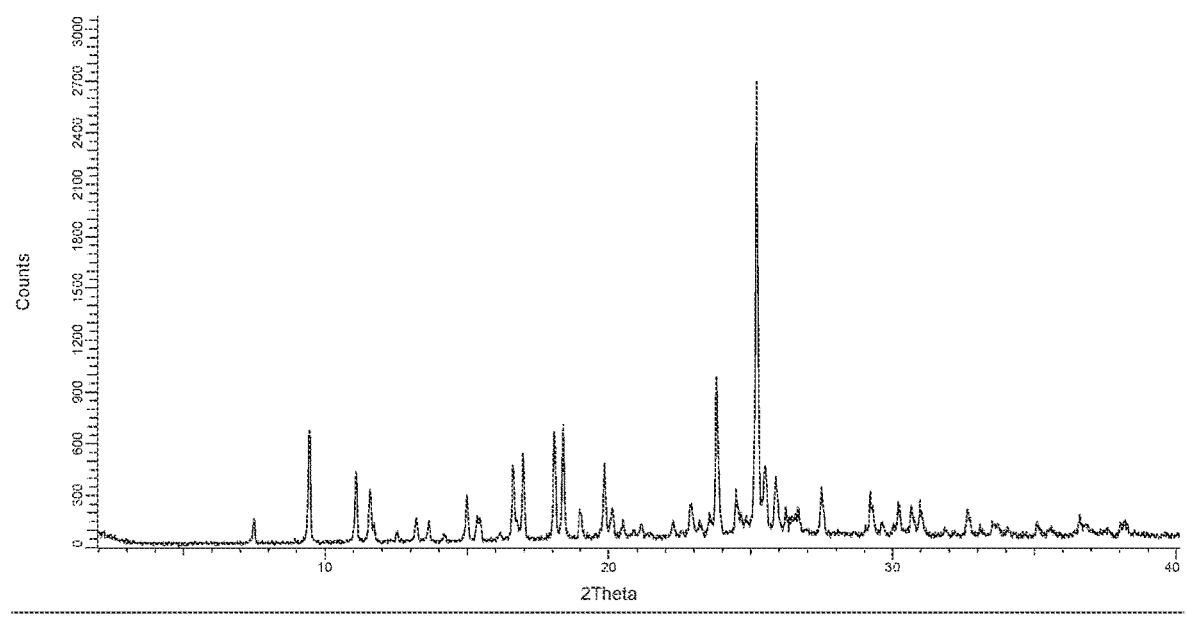

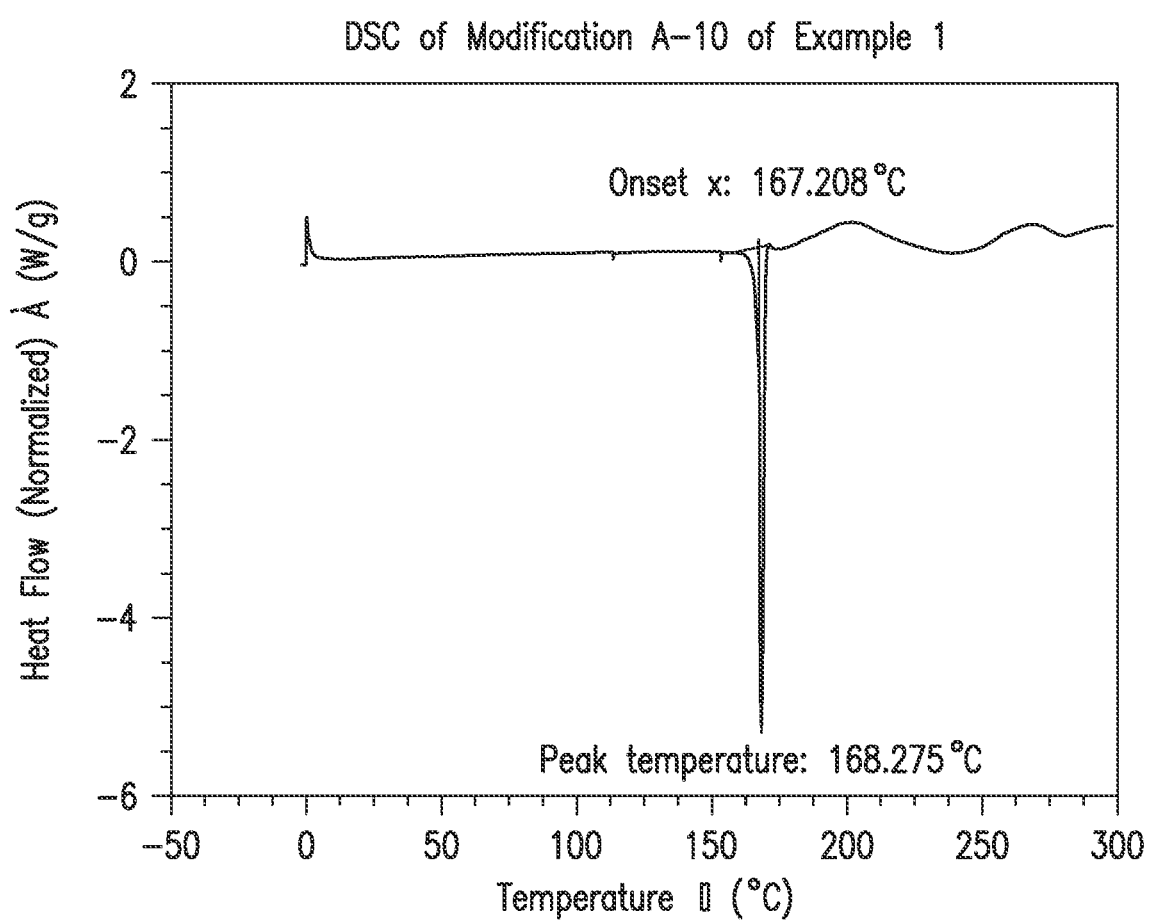
Figure A10-2

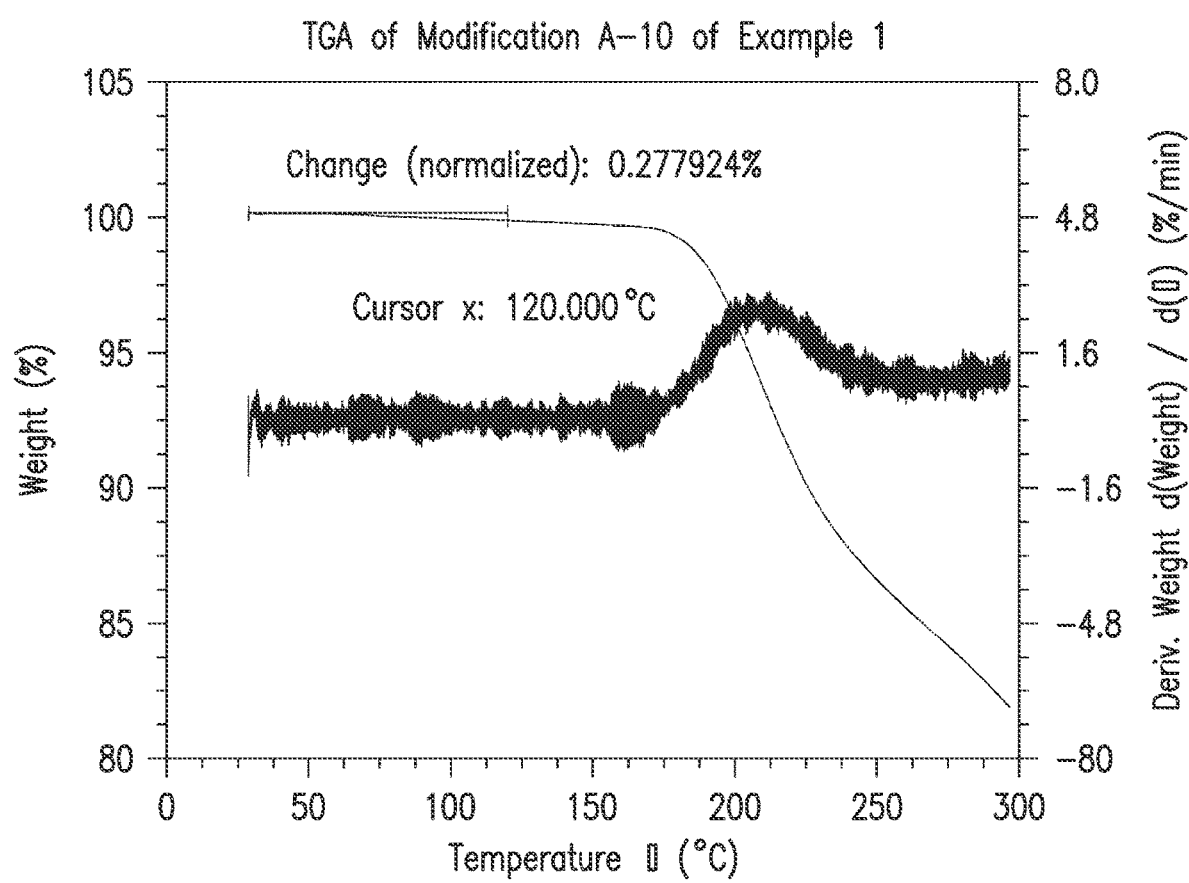
Figure A10-3

Figure A11-1. XRPD of Modification A-11 of Example 1
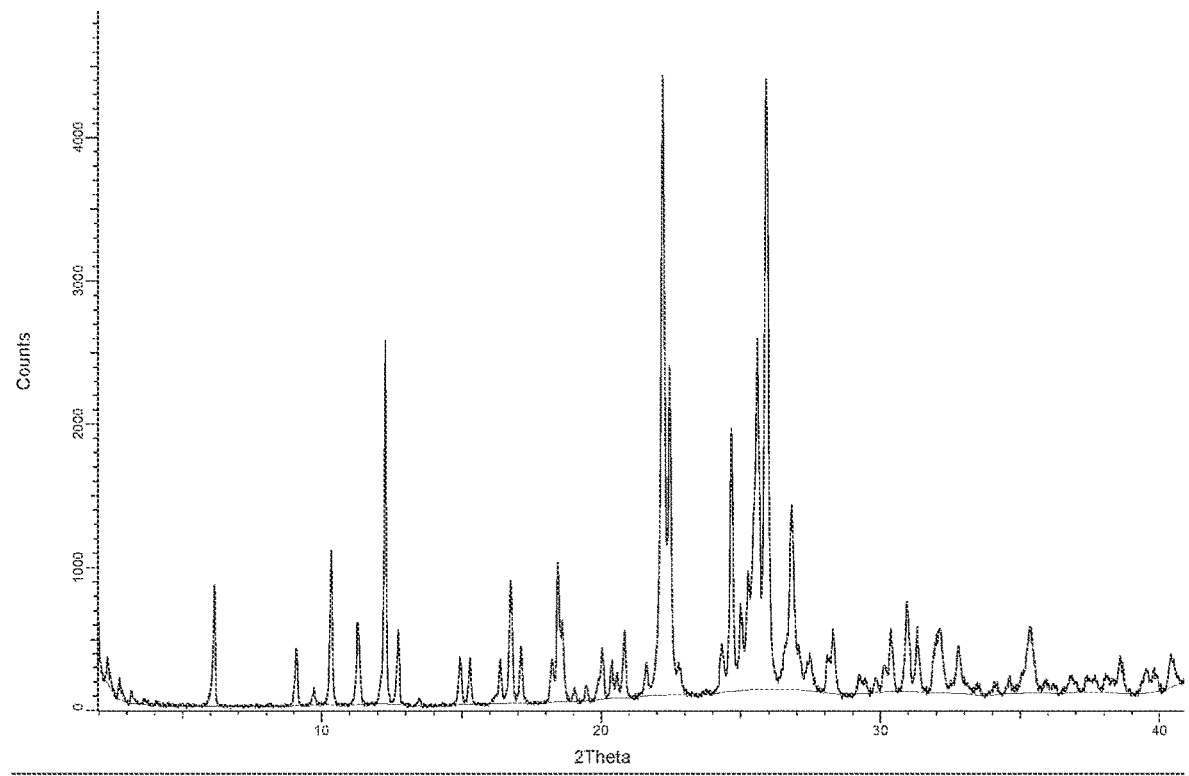
Figure A11-2. DSC of Modification A-11 of Example 1
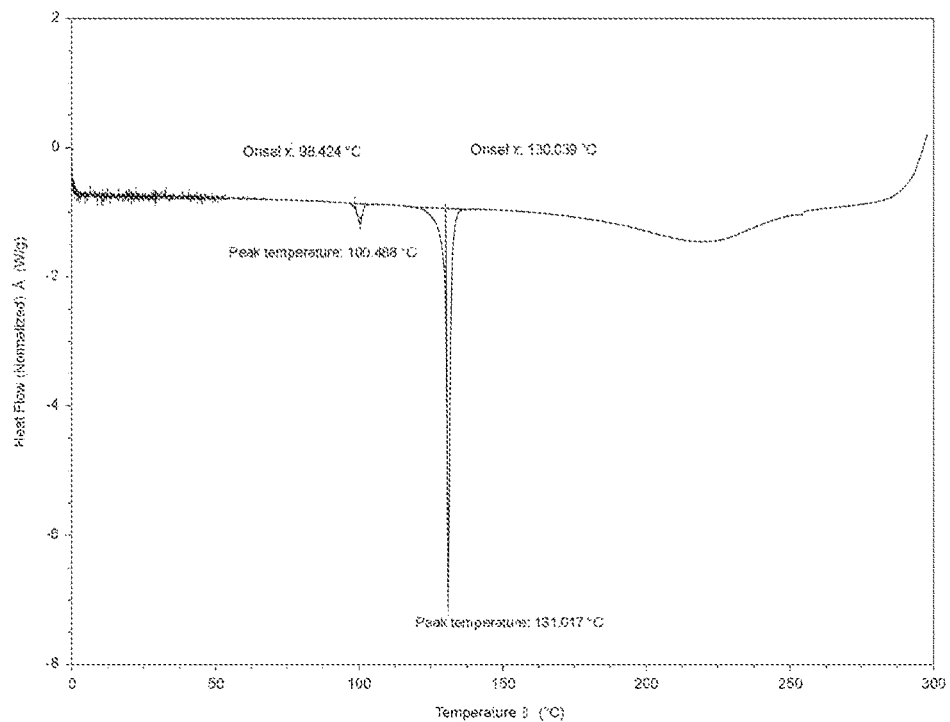

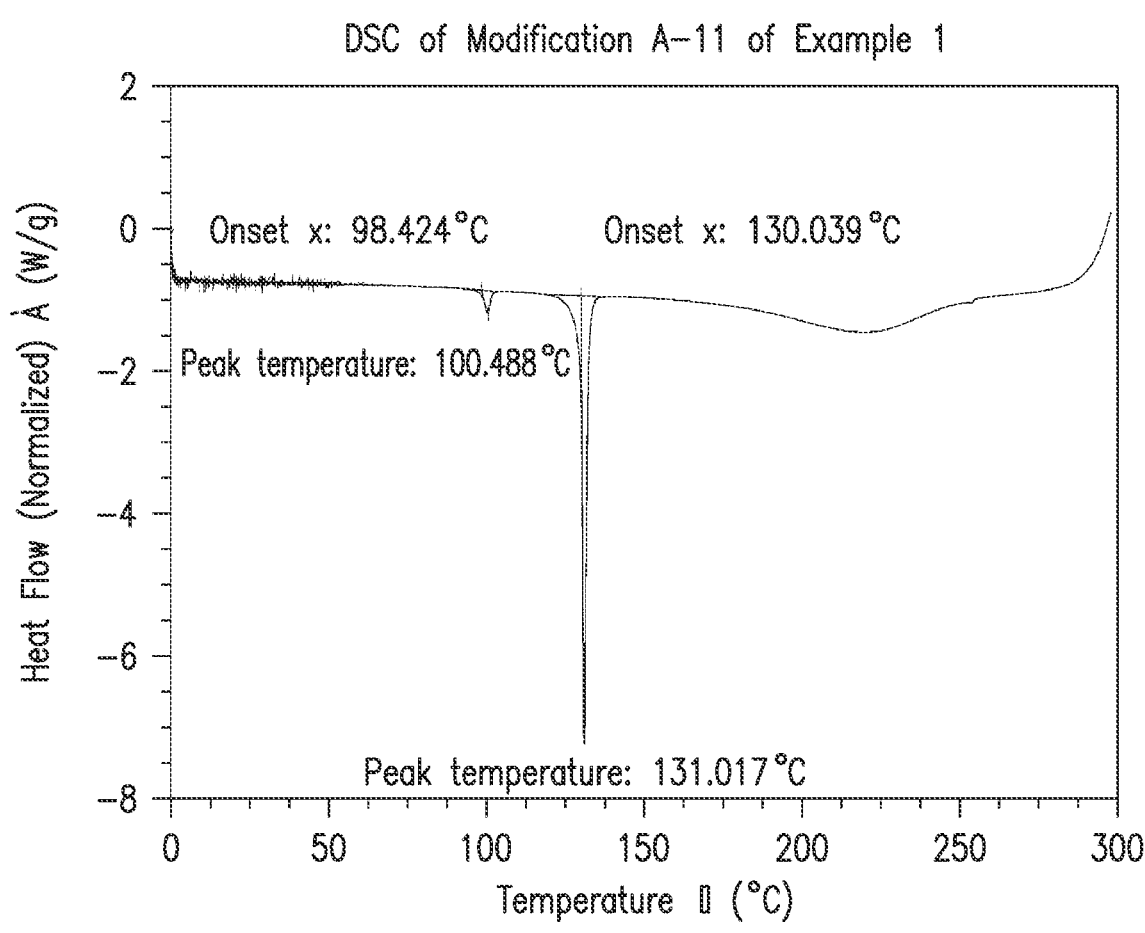
Figure A11-2

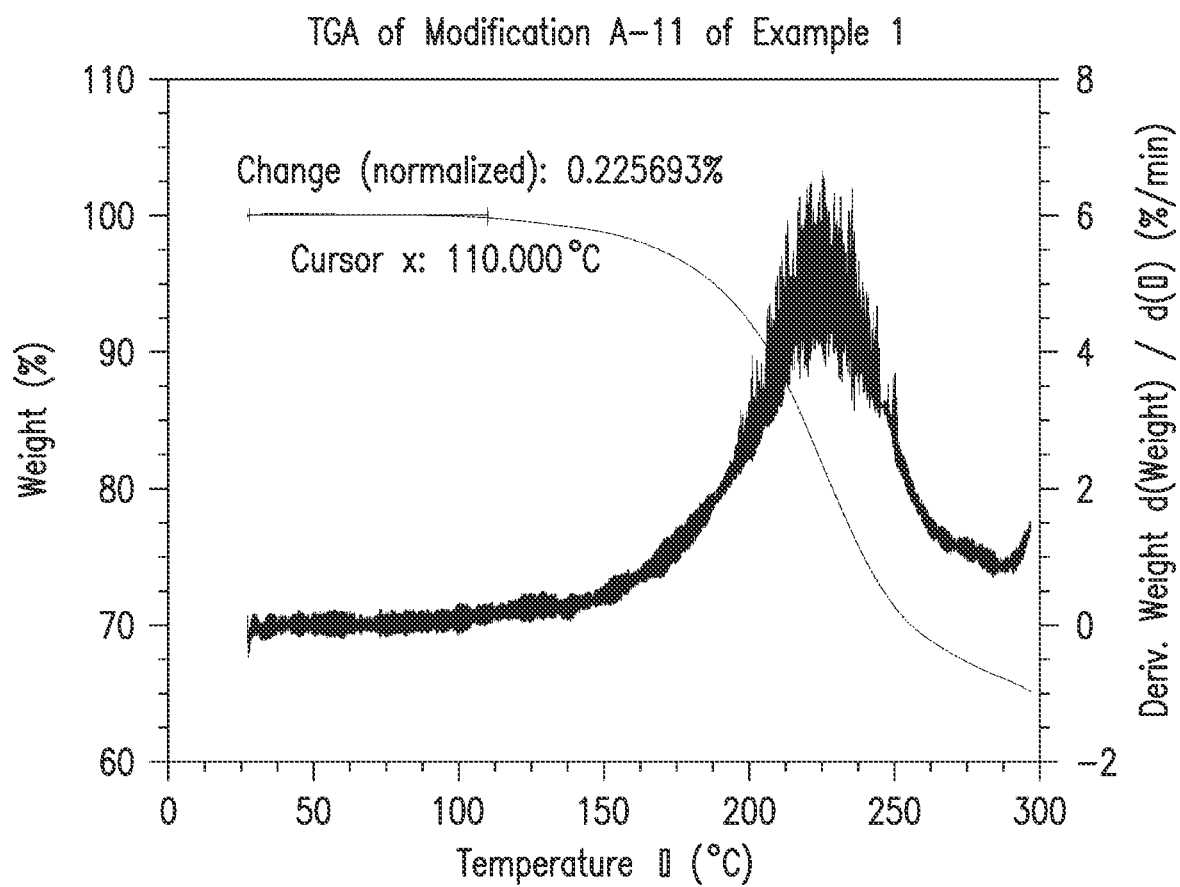
Figure A11-3

Figure A11-3. TGA of Modification A-11 of Example 1
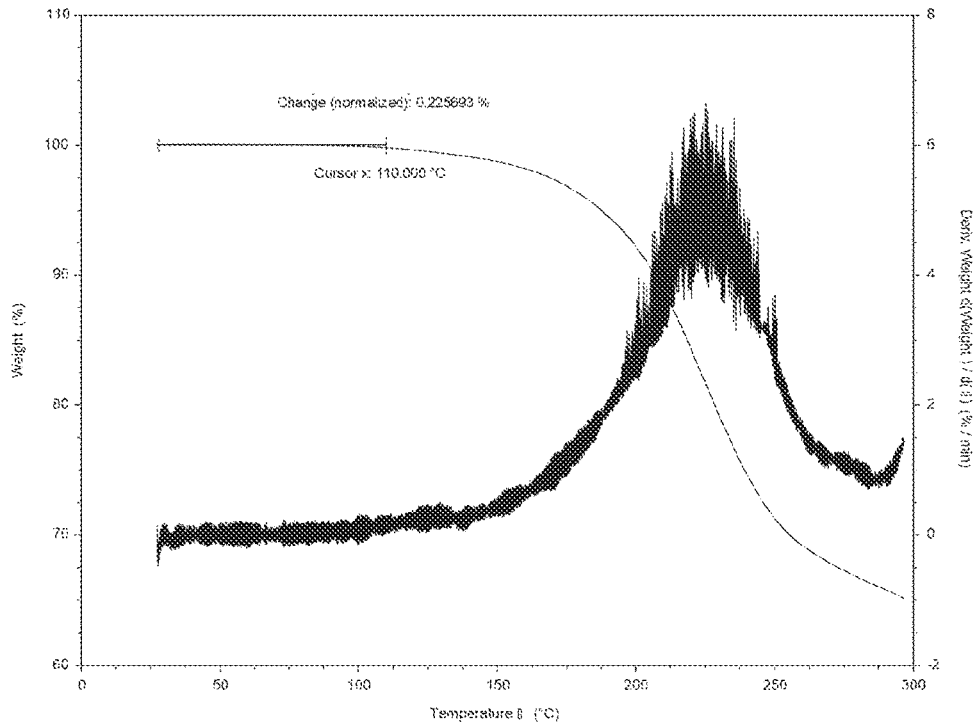
Figure A12-1. XRPD of Modification A-12 of Example 1
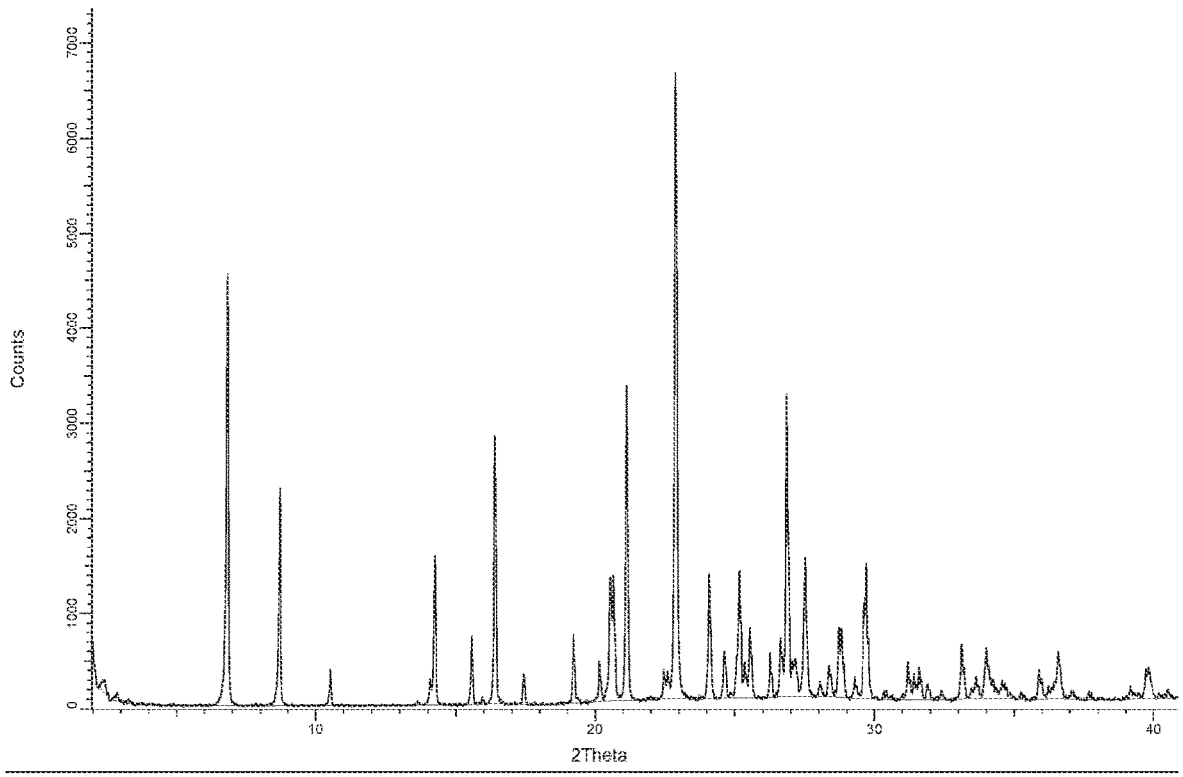

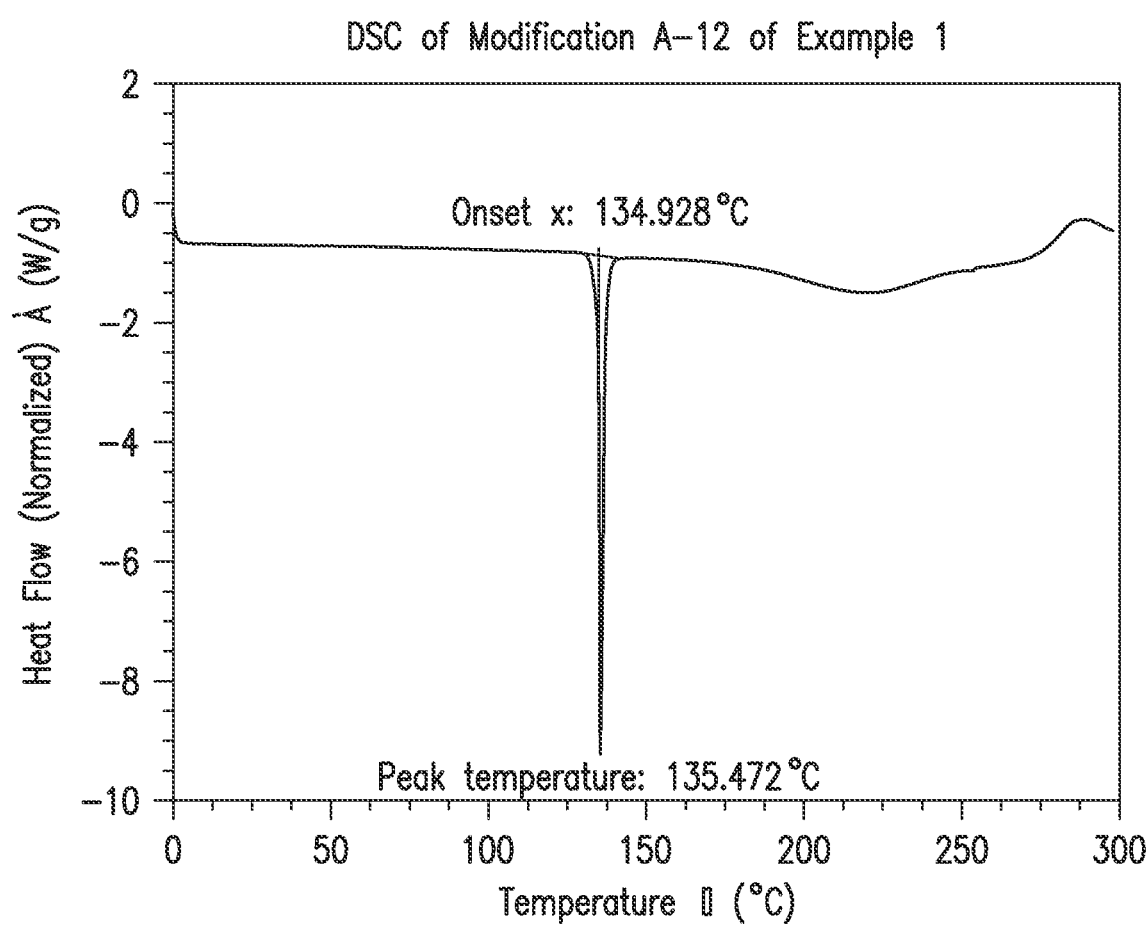
Figure A12-2

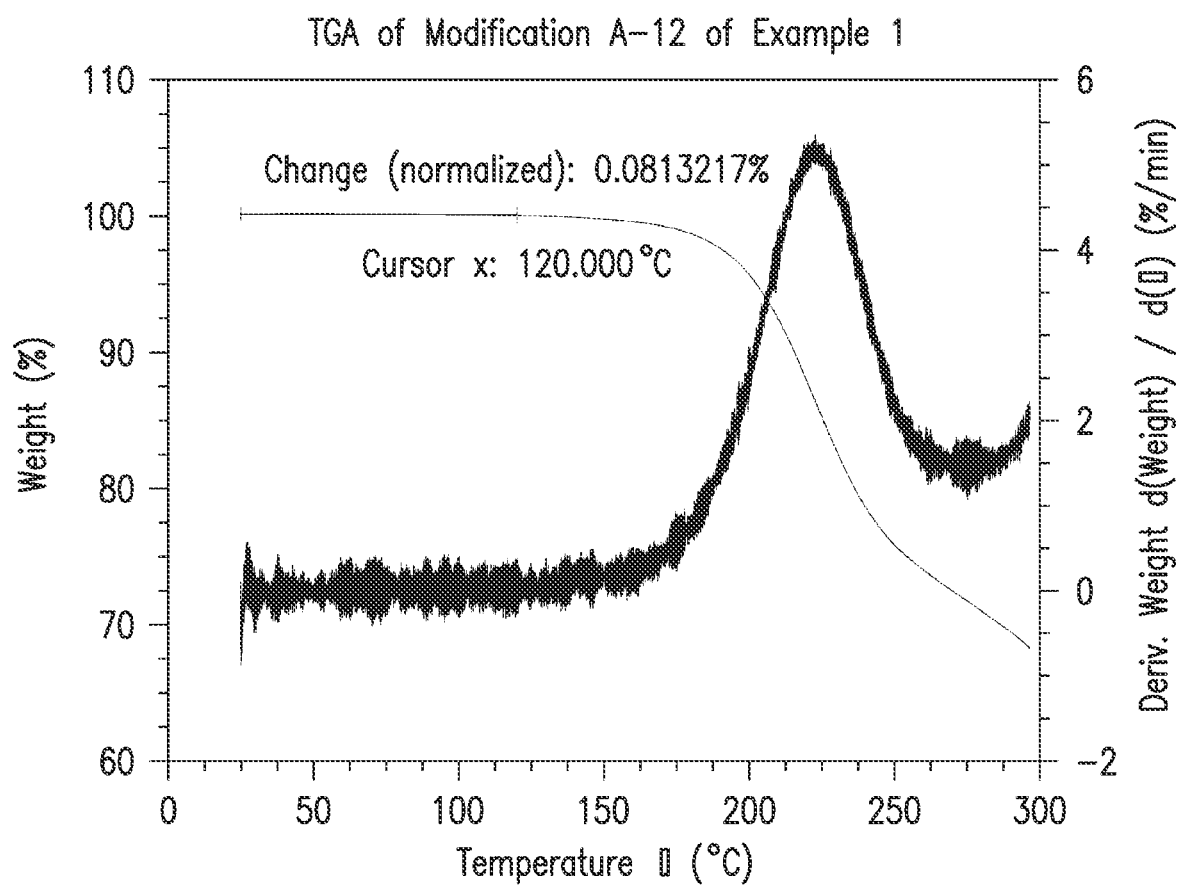
Figure A12-3

Figure A13-1. XRPD of Modification A-13 of Example 1
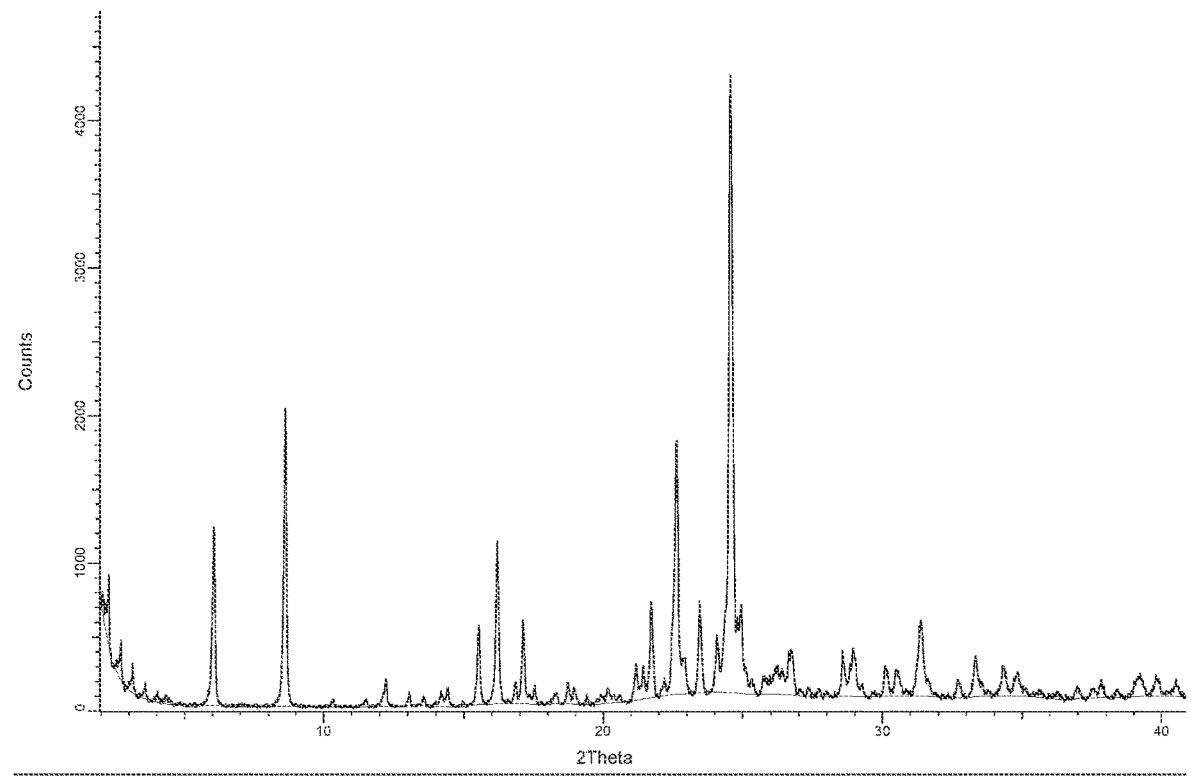
Figure A13-2. DSC of Modification A-13 of Example 1
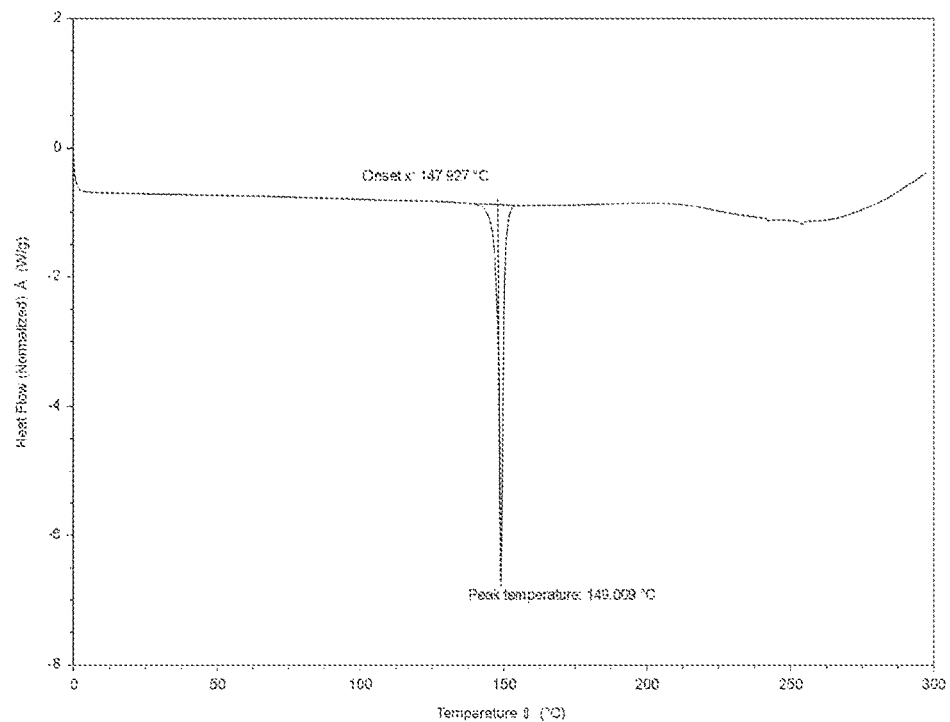

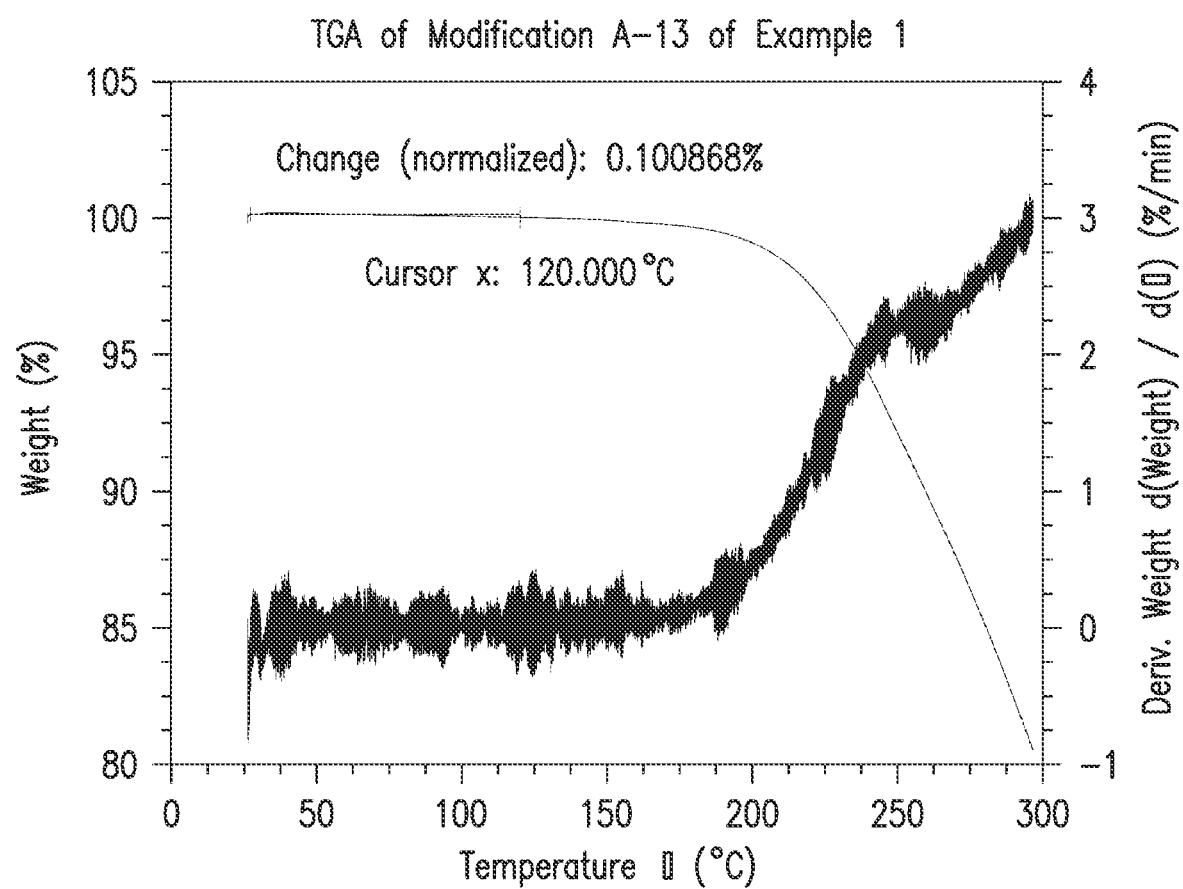
Figure A13-3

NAPHTHYRIDINONE DERIVATIVES FOR THE TREATMENT OF A DISEASE OR DISORDER

RELATED APPLICATIONS

This application claims the benefit of and priority to International Application No. PCT/CN2022/128601, filed Oct. 31, 2022 and U.S. Provisional Application No. 63/282,492, filed Nov. 23, 2021, the entire contents of each of which are hereby incorporated by reference in their entireties.

TECHNICAL FIELD

The present invention is directed naphthyridinone compounds, the use thereof for inhibiting the GIRK1/4 channel and methods of treating a disease or disorder using the same.

BACKGROUND

A normal cardiac cycle begins in the sino-atrial node, which produces an excitatory electrical stimulus that propagates in an orderly fashion throughout the atrial and ventricular myocardium to induce a contraction (systole). At the cellular level, the excitatory electrical impulse triggers the cardiac action potential. This is characterized by an initial, rapid membrane depolarization followed by a plateau phase and subsequent repolarization to return to resting membrane potential. The cardiac action potential governs signal propagation throughout the heart. For example, the rate of initial cellular depolarization determines the velocity at which excitatory stimuli propagate. The duration of the repolarization phase determines the action potential duration (APD) and the refractory period, or time in which a cardiomyocyte cannot respond to another electrical stimulus.

Abnormalities in the cardiac action potential are associated with arrhythmia. For example, excessive reduction of action potential duration and the associated refractory period can provide a substrate for so-called re-entrant tachyarrhythmia. In this condition, instead of propagating normally, a cardiac impulse feeds back upon itself via excitable tissue to form a re-entrant circuit (Waldo et al., Lancet 341, 1189-1193). Existing class III anti-arrhythmic drugs are thought to work by lengthening the APD and associated effective refractory period (ERP), thereby minimizing the risk of re-excitation and subsequent formation of fibrillatory re-entry circuits (Singh et al., British Journal of pharmacology 39, 675-687).

Certain class III anti-arrhythmic drugs (e.g., sotalol) are used in the treatment of atrial fibrillation (AF). AF is the most common form of sustained cardiac arrhythmia in humans and is characterized by fibrillatory contractions that compromise atrial function. AF is associated with adverse cardiovascular events. In particular, the presence of AF is an independent risk factor for thromboembolic stroke, heart failure and all-cause mortality (Estes et al., (2008). Journal of the American College of Cardiology 51, 865-884) (Fang et al., 2008. Journal of the American College of Cardiology 51, 810-815). AF can also reduce quality of life in some patients by inducing palpitations and reducing exercise tolerance (Thrall et al., 2006. The American journal of medicine 119, 448.e441-419). The goal of anti-arrhythmic therapy for AF is to avoid these adverse effects and outcomes.

A drawback of existing Class III anti-arrhythmic drugs is that they act to prolong effective refractory period in both atria and ventricles. Excessive prolongation in ventricular tissue lengthens QTc interval and can be pro-arrhythmic, and certain drugs with this mechanism of action (e.g., dofetilide) are known to induce potentially life-threatening ventricular arrhythmias such as Torsades de Pointes (Redfern et al., 2003. Cardiovascular Research 58, 32-45). There is thus a need for a novel anti-arrhythmic therapy for AF that targets atrial, and not ventricular, tissue selectively.

The configuration and duration of the cardiac action potential is controlled at the cellular level by the action of multiple different transmembrane ion channels. For example, the initial depolarization phase is mediated by influx of sodium ions via the cardiac-specific $Na_v1.5$ channel. Potassium channels are responsible for the latter phase of repolarization, and thus help regulate the overall duration of the action potential. Indeed, class III anti-arrhythmic drugs that target potassium channels (e.g., dofetilide) prolong both action potential duration and effective refractory period. There are several different varieties of transmembrane potassium channel (Schmitt et al., 2014. Physiological reviews 94, 609-653; Tamargo et al., 2004. Cardiovascular research 62, 9-33), including:

Voltage-gated channels (Kv1-9)
Calcium-activated channels (KCal-2)
Tandem pore domain channels (e.g., TASK)
Inwardly rectifying channels (Kirl-6)

While most cardiac potassium channels contribute to repolarization in both atrial and ventricular tissues in humans, two—$K_v1.5$ and GIRK1/4 (i.e., G-protein regulated inwardly rectifying potassium channel 1/4)—are thought to be expressed solely in atria (Gaborit et al., 2007. The Journal of physiology 582, 675-693). This atrial-specific pattern of expression makes these particularly attractive targets for novel anti-arrhythmic therapies for AF, as they should not have the adverse ventricular effects of existing Class III drugs such as dofetilide.

Mammals express four different GIRK channels (GIRK 1, 2, 3 and 4; encoded by KCNJ3, KCNJ6, KCNJ9 and KCNJ5, respectively). These transmembrane spanning proteins are arranged as tetramers (either homo or heterotetramers) to form a functional potassium channel (Krapivinsky et al., 1995. Nature 374, 135-141). These channels are ligand-gated (i.e., regulated by binding of ligands to Gi-protein coupled receptors present in the same cell membrane). For example, the GIRK1/4 channel is a heterotetramer (two subunits each of GIRK1 and GIRK4) expressed strongly in sino-atrial and atrioventricular nodes as well as the atrial myocardium (Wickman et al., 1999. Annals of the New York Academy of Sciences 868, 386-398). One function of this channel is to mediate autonomic regulation of heart rate. Acetylcholine released upon parasympathetic stimulation of cardiac vagal efferent neurons binds to Gi-coupled M2 muscarinic receptors in heart. This liberates Gβγ subunits, which in turn open GIRK1/4 channels to permit efflux of potassium from cardiomyocytes and so promote membrane repolarization. In the spontaneously depolarizing pacemaking cells of the sino-atrial node, the magnitude of this repolarization dictates the timing between depolarizations, and hence heart rate. Because it is regulated by acetylcholine, the current mediated by GIRK1/4 channels is called $I_{KAch}$ (Wickman et al., 1999).

Several lines of evidence point toward GIRK1/4 as a desirable anti-arrhythmia target for AF. In animals, vagal nerve stimulation promotes acetylcholine release from vagal afferents and an increase in $I_{KAch}$. This in turn shortens atrial (but not ventricular) action potential duration and effective refractory period and can induce AF via a re-entry mechanism (Hashimoto et al., 2006. Pharmacological research: the official journal of the Italian Pharmacological Society 54, 136-141). In atrial tissues from humans with persistent AF as well as from animals subjected to atrial rapid pacing (an accepted model for promoting electrical remodeling and susceptibility to AF), $I_{KAch}$ has been shown to be dysregulated. Specifically, the channel tends to be constitutively open, even in the absence of acetylcholine (Cha et al., 2006. Circulation 113, 1730-1737; Voigt et al., 2014. Advances in pharmacology (San Diego, Calif) 70, 393-409). In these studies, it is observed in patients and animals that atrial APD/ERP is short.

Thus, the development of GIRK1/4 blockers would be beneficial in the treatment of a range of cardiac-related diseases. For these reasons, there remains a need for small molecule inhibitors of GIRK1/4.

SUMMARY

In a first aspect, the present invention relates to a compound of formula (I):

(I)

or a pharmaceutically acceptable salt thereof, wherein
$R^1$ is ($C_1$-$C_6$)alkyl substituted with one or more substituents independently selected from —OH, —C(O)NHR$^a$ and a 4- to 6-membered heterocycle which is optionally substituted with one or more —OH; A is —OR$^2$ or ($C_1$-$C_6$)alkyl optionally substituted with one or more substituents independently selected from —SO$_2$($C_1$-$C_4$)alkyl, —NHC(O) R$^b$, and —C(O)NHR$^c$;
$R^2$ is ($C_1$-$C_6$)alkyl substituted with one or more substituents independently selected from —NHC(O)R$^d$ and —C(O) NHR$^e$, wherein the ($C_1$-$C_6$)alkyl is further optionally substituted with one or more substituents independently selected from halo, —OH and —CN;
$R^a$, $R^b$, $R^c$, $R^d$, and $R^e$ are each independently selected from H and ($C_1$-$C_6$)alkyl optionally substituted with one or more —OH; and
$R^3$ is ($C_1$-$C_4$)alkyl.

In another aspect, the present invention relates to a crystalline form of a compound of formula (I) or a pharmaceutically acceptable salt thereof as defined herein.

In another aspect, the present invention relates to a pharmaceutical composition comprising a compound of formula (I) or a pharmaceutically acceptable salt thereof as defined herein and one or more pharmaceutically acceptable carriers.

In another aspect, the present invention relates to a combination comprising a compound of formula (I) or a pharmaceutically acceptable salt thereof as defined herein and one or more pharmaceutical agents.

In another aspect, the present invention relates to a method for treating a disease or disorder comprising administering to a patient in need thereof a therapeutically effective amount of a compound of formula (I) or a pharmaceutically acceptable salt thereof as defined herein.

In some embodiments, the disease or disorder is selected from cardiac arrhythmia, atrial fibrillation, bradyarrhythmia, bradycardia, heart block, sick sinus syndrome, parasympathetic hyperactivation, primary hyperaldosteronism, hypotension, and vasovagal syncope. In some embodiments, the disease or disorder is responsive to the inhibition of the GIRK1/4 receptor.

In another aspect, the present invention relates to a method for treating a disease or disorder comprising administering to a patient in need thereof a therapeutically effective amount of a compound of formula (I) or a pharmaceutically acceptable salt thereof as defined herein.

In yet another aspect, the present invention relates to a method for maintaining a sinus rhythm after cardioversion in a patient with persistent or recent onset of atrial fibrillation or preventing a recurrence in a patient with paroxysmal atrial fibrillation comprising administering to a patient in need thereof a compound of formula (I) or a pharmaceutically acceptable salt thereof as defined herein.

In another aspect, the present invention relates to a compound of formula (I) or a pharmaceutically acceptable salt thereof as defined herein for use as a medicament.

In another aspect, the present invention relates to a compound of formula (I) or a pharmaceutically acceptable salt thereof as defined herein for use in the treatment of a disease or disorder.

In yet another aspect, the present invention relates to a compound of formula (I) as defined herein for use in the manufacture of a medicament for treating a disease or disorder.

In still another aspect, the present invention relates to use of a compound of formula (I) or a pharmaceutically acceptable salt thereof as defined herein in the treatment of a disease or disorder.

Other features and advantages of the invention will be apparent from the following detailed description and claims.

BRIEF DESCRIPTION OF DRAWINGS

FIG. A1-1 shows the X-ray powder diffraction pattern of Modification A-1 of Example 1.

FIG. A1-2 shows the Differential Scanning Calorimetry thermogram of Modification A-1 of Example 1.

FIG. A1-3 shows the Thermogravimetric Analysis of Modification A-1 of Example 1.

FIG. A2-1 shows the X-ray powder diffraction pattern of Modification A-2 of Example 1.

FIG. A2-2 shows the Differential Scanning Calorimetry thermogram of Modification A-2 of Example 1.

FIG. A2-3 shows the Thermogravimetric Analysis of Modification A-2 of Example 1.

FIG. A3-1 shows the X-ray powder diffraction pattern of Modification A-3 of Example 1.

FIG. A3-2 shows the Differential Scanning Calorimetry thermogram of Modification A-3 of Example 1.

FIG. A3-3 shows the Thermogravimetric Analysis of Modification A-3 of Example 1.

FIG. A4-1 shows the X-ray powder diffraction pattern of Modification A-4 of Example 1.

FIG. A4-2 shows the Differential Scanning Calorimetry thermogram of Modification A-4 of Example 1.

FIG. A4-3 shows the Thermogravimetric Analysis of Modification A-4 of Example 1.

FIG. A5-1 shows the X-ray powder diffraction pattern of Modification A-5 of Example 1.

FIG. A5-2 shows the Differential Scanning Calorimetry thermogram of Modification A-5 of Example 1.

FIG. A5-3 shows the Thermogravimetric Analysis of Modification A-5 of Example 1.

FIG. A6-1 shows the X-ray powder diffraction pattern of Modification A-6 of Example 1.

FIG. A7-1 shows the X-ray powder diffraction pattern of Modification A-7 of Example 1.

FIG. A8-1 shows the X-ray powder diffraction pattern of Modification A-8 of Example 1.

FIG. A9-1 shows the X-ray powder diffraction pattern of Modification A-9 of Example 1.

FIG. A9-2 shows the Differential Scanning Calorimetry thermogram of Modification A-9 of Example 1.

FIG. A9-3 shows the Thermogravimetric Analysis of Modification A-9 of Example 1.

FIG. A10-1 shows the X-ray powder diffraction pattern of Modification A-10 of Example 1.

FIG. A10-2 shows the Differential Scanning Calorimetry thermogram of Modification A-10 of Example 1.

FIG. A10-3 shows the Thermogravimetric Analysis of Modification A-10 of Example 1.

FIG. A11-1 shows the X-ray powder diffraction pattern of Modification A-11 of Example 1.

FIG. A11-2 shows the Differential Scanning Calorimetry thermogram of Modification A-11 of Example 1.

FIG. A11-3 shows the Thermogravimetric Analysis of Modification A-11 of Example 1.

FIG. A12-1 shows the X-ray powder diffraction pattern of Modification A-12 of Example 1.

FIG. A12-2 shows the Differential Scanning Calorimetry thermogram of Modification A-12 of Example 1.

FIG. A12-3 shows the Thermogravimetric Analysis of Modification A-12 of Example 1.

FIG. A13-1 shows the X-ray powder diffraction pattern of Modification A-13 of Example 1.

FIG. A13-2 shows the Differential Scanning Calorimetry thermogram of Modification A-13 of Example 1.

FIG. A13-3 shows the Thermogravimetric Analysis of Modification A-13 of Example 1.

DETAILED DESCRIPTION

In certain aspects, the present invention provides substituted naphthyridinone compounds, and pharmaceutical compositions thereof. In particular, such substituted compounds are useful as inhibitors of the GIRK1/4 receptor and have good oral bioavailability and thus can be used to treat or prevent a disease or condition.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Compounds

In one aspect, the present invention therefore provides a compound of formula (I):

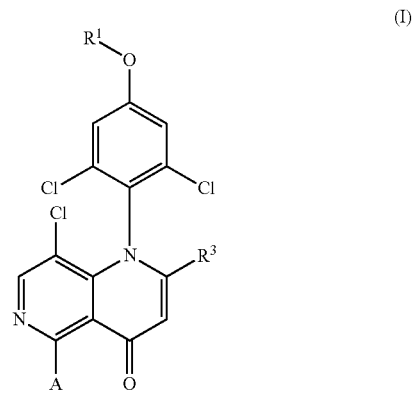

or a pharmaceutically acceptable salt thereof, wherein
$R^1$ is $(C_1$-$C_6)$alkyl substituted with one or more substituents independently selected from —OH, —C(O)NHR$^a$ and a 4 to 6 membered heterocycle which is optionally substituted with one or more —OH; A is —OR$^2$ or $(C_1$-$C_6)$alkyl optionally substituted with one or more substituents independently selected from —SO$_2$($C_1$-$C_4$)alkyl, —NHC(O)R$^b$, and —C(O)NHR$^c$;
$R^2$ is $(C_1$-$C_6)$alkyl substituted with one or more substituents independently selected from —NHC(O)R$^d$ and —C(O)NHR$^e$, wherein the $(C_1$-$C_6)$alkyl is further optionally substituted with one or more substituents independently selected from halo, —OH and —CN;
$R^a$, $R^b$, $R^c$, $R^d$, and $R^e$ are each independently selected from H and $(C_1$-$C_6)$alkyl optionally substituted with one or more —OH; and
$R^3$ is $(C_1$-$C_4)$alkyl.

Unless specified otherwise, the term "compounds of the present invention" or "compound of the present invention" refers to compounds of formula (I) thereof, and exemplified compounds, or pharmaceutically acceptable salts thereof, as well as all stereoisomers (including diastereoisomers and enantiomers), rotamers, tautomers, hydrates, solvates, polymorphs, co-crystals, and isotopically labeled compounds (including deuterium substitutions), as well as inherently formed moieties.

Various embodiments of the invention are described herein. It will be recognized that features specified in each embodiment may be combined with other specified features of other embodiments to provide further embodiments.

In some embodiments, $R^1$ is $(C_1$-$C_6)$alkyl substituted with one or more substituents independently selected from —OH, —C(O)NHR$^a$ and a 4- to 6-membered heterocycle containing at least one O which is optionally substituted with one or more —OH. In some embodiments, $R^1$ is $(C_1$-$C_6)$alkyl substituted with one or more substituents independently selected from —OH, —C(O)NHR$^a$ and a 4- to 6-membered heterocycle containing at least one O which is optionally substituted with one —OH. In some embodiments, $R^1$ is $(C_1$-$C_6)$alkyl substituted with one or more substituents independently selected from —OH, —C(O)NHR$^a$ and a 4-membered heterocycle containing at least one O which is optionally substituted with one or more —OH. In some embodiments, $R^1$ is $(C_1-C_6)$alkyl substituted with one or more substituents independently selected from —OH, —C(O)NHR$^a$ and a 4-membered heterocycle containing at least one O which is substituted with one —OH.

In some embodiments, $R^1$ is $(C_1-C_6)$alkyl substituted with one or more substituents independently selected from —OH, —C(O)NHCH$_3$, and

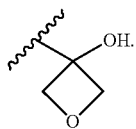 [SMILES: *C1(O)COC1]

In some embodiments, $R^1$ is $(C_1-C_4)$alkyl substituted with one or more substituents independently selected from —OH, —C(O)NHCH$_3$, and

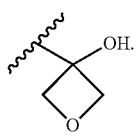 [SMILES: *C1(O)COC1]

In certain embodiments, $R^1$ is selected from

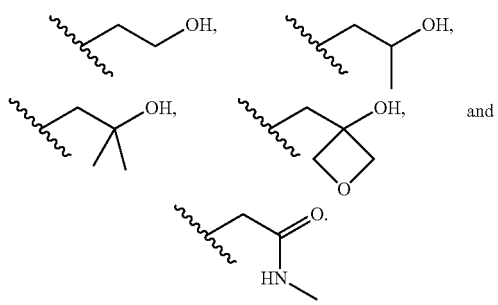

In some embodiments, $R^1$ is selected from

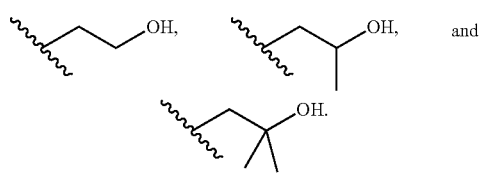

In some embodiments, $R^1$ is selected from

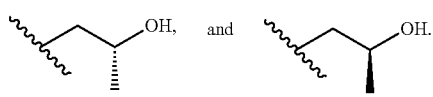

In some embodiments, $R^1$ is

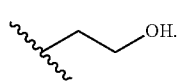

In some embodiments, $R^a$ is selected from H and $(C_1-C_6)$alkyl.

In some embodiments, A is —OR$^2$.

In some embodiments, $R^2$ is $(C_1-C_6)$alkyl substituted with one or more substituents independently selected from —NHC(O)CH$_3$, —C(O)NHCH$_3$, —C(O)NHCH$_2$CH$_2$OH, and —C(O)NH$_2$, and wherein the $(C_1-C_6)$alkyl is further optionally substituted with one or more substituents independently selected from halo, —OH and —CN. In some embodiments, $R^2$ is $(C_1-C_4)$alkyl substituted with one or more substituents independently selected from —NHC(O)CH$_3$, —C(O)NHCH$_3$, —C(O)NHCH$_2$CH$_2$OH, and —C(O)NH$_2$, and wherein the $(C_1-C_4)$alkyl is further optionally substituted with one or more substituents independently selected from halo, —OH and —CN. In some embodiments, $R^2$ is $(C_1-C_4)$alkyl substituted with one or more substituents independently selected from —NHC(O)CH$_3$, —C(O)NHCH$_3$, —C(O)NHCH$_2$CH$_2$OH, and —C(O)NH$_2$, and wherein the $(C_1-C_4)$alkyl is further optionally substituted with one or more substituents independently selected from halo and —OH. In some embodiments, $R^2$ is $(C_1-C_4)$alkyl substituted with one or more substituents independently selected from —NHC(O)CH$_3$, —C(O)NHCH$_3$, —C(O)NHCH$_2$CH$_2$OH, and —C(O)NH$_2$, wherein the $(C_1-C_4)$alkyl is further optionally substituted with one or more substituents independently selected from fluoro and —OH.

In certain embodiments, $R^2$ is selected from

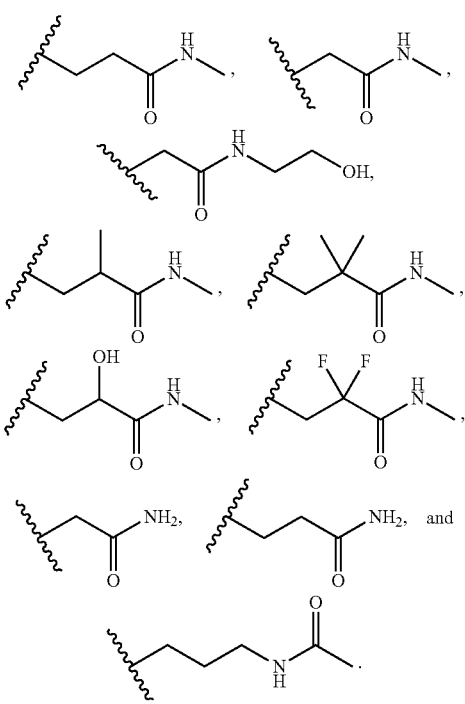

In some embodiments, $R^2$ is selected from

-continued

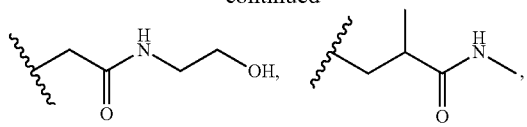

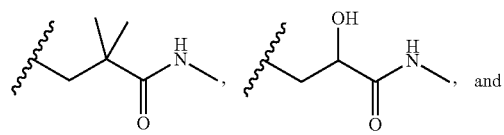

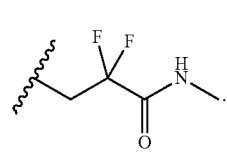

In some embodiments, R² is selected from

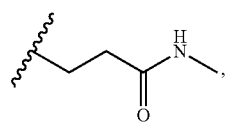 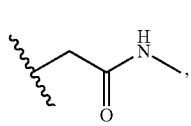

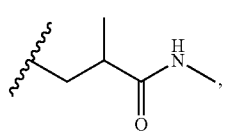 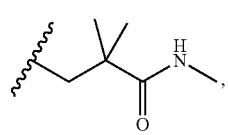

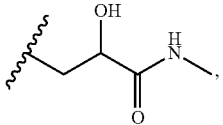 and 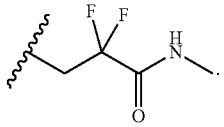.

In some embodiments, R² is selected from

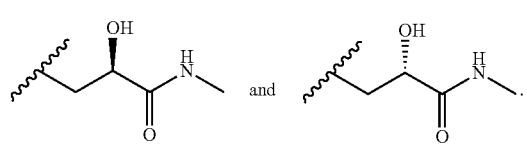

In some embodiments, R² is selected from

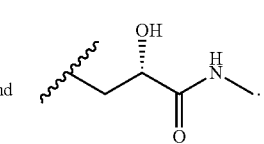

In some embodiments, A is (C₁-C₆)alkyl optionally substituted with one or more substituents independently selected from —SO₂CH₃ and —NHC(O)CH₃. In some embodiments, A is (C₁-C₄)alkyl optionally substituted with one or more substituents independently selected from —SO₂CH₃ and —NHC(O)CH₃.

In certain embodiments, A is selected from

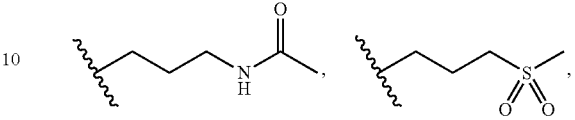

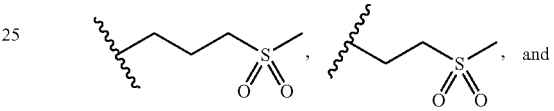

In certain embodiments, A is selected from

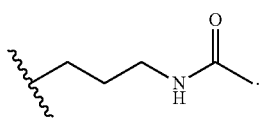

In certain embodiments, A is

In some embodiments, R³ is selected from —CH₃ and —CH₂CH₃. In some embodiments, R³ is —CH₃.

In some embodiments, Rᵃ is selected from H and (C₁-C₆)alkyl. In some embodiments, R is selected from H and (C₁-C₆)alkyl. In some embodiments, Rᶜ is selected from H and (C₁-C₆)alkyl. In some embodiments, Rᵈ is selected from H and (C₁-C₆)alkyl. In some embodiments, R³ is selected from H and (C₁-C₆)alkyl. In some embodiments, Rᵃ is selected from H and (C₁-C₄)alkyl. In some embodiments, R is selected from H and (C₁-C₄)alkyl. In some embodiments, Rᶜ is selected from H and (C₁-C₄)alkyl. In some embodiments, Rᵈ is selected from H and (C₁-C₄)alkyl. In some embodiments, R³ is selected from H and (C₁-C₄)alkyl. In some embodiments, Rᶜ is selected from H and (C₁-C₄)alkyl optionally substituted with one or more —OH.

In certain embodiments, the compound of formula (I) according to the invention is a compound or a pharmaceutically acceptable salt thereof selected from the group consisting of:

| Compound | Structure | Chemical Name |
|---|---|---|
| C-1 | 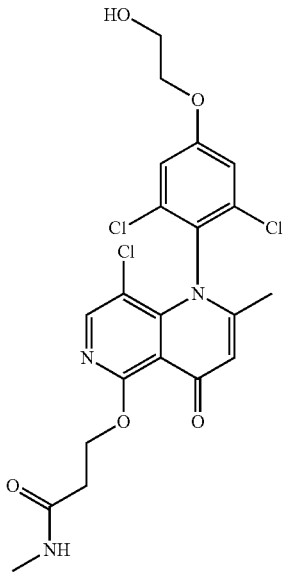 | 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide |
| C-2 | 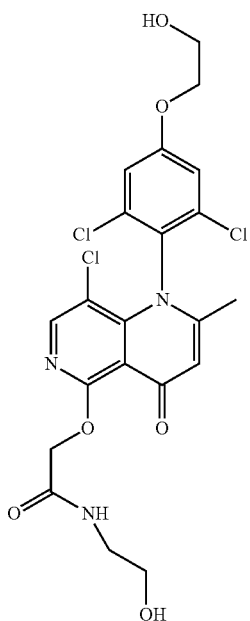 [SMILES: Cc1cc(=O)c2c(OCC(=O)NCCO)ncc(Cl)c2n1-c1c(Cl)cc(OCCO)cc1Cl] | 2-((8-chloro-1-(2,6-dichloro-4-(2-hydroxyethoxy)phenyl)-2-methyl-4-oxo-1,4-dihydro-1,6-naphthyridin-5-yl)oxy)-N-(2-hydroxyethyl)acetamide |

-continued

| Compound | Structure | Chemical Name |
|---|---|---|
| C-3 | 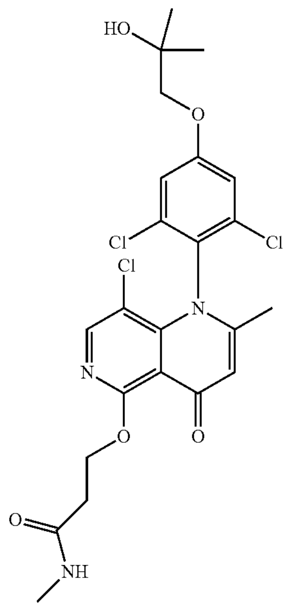 [SMILES: CNC(=O)CCOc1ncc(Cl)c2c1c(=O)cc(C)n2-c1c(Cl)cc(OCC(C)(C)O)cc1Cl] | 3-((8-chloro-1-(2,6-dichloro-4-(2-hydroxy-2-methylpropoxy)phenyl)-2-methyl-4-oxo-1,4-dihydro-1,6-naphthyridin-5-yl)oxy)-N-methylpropanamide |
| C-4 | 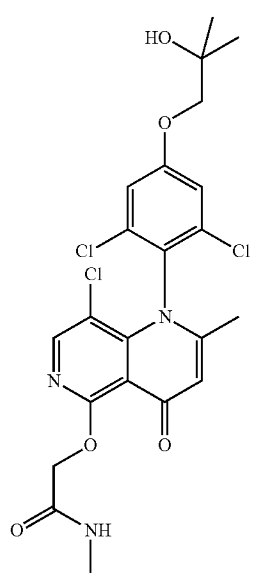 [SMILES: CNC(=O)COc1ncc(Cl)c2c1c(=O)cc(C)n2-c1c(Cl)cc(OCC(C)(C)O)cc1Cl] | 2-((8-chloro-1-(2,6-dichloro-4-(2-hydroxy-2-methylpropoxy)phenyl)-2-methyl-4-oxo-1,4-dihydro-1,6-naphthyridin-5-yl)oxy)-N-methylacetamide |

| Compound | Structure | Chemical Name |
|---|---|---|
| C-5 | 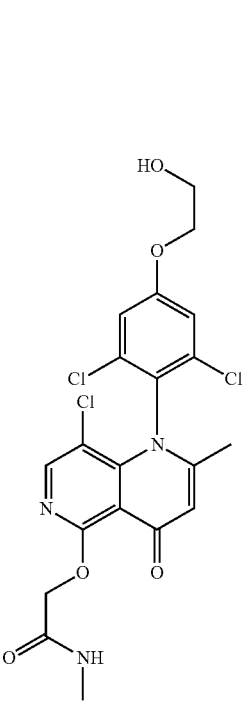 [SMILES: CNC(=O)COc1ncc(Cl)c2c1c(=O)cc(C)n2-c1c(Cl)cc(OCCO)cc1Cl] | 2-((8-chloro-1-(2,6-dichloro-4-(2-hydroxyethoxy)phenyl)-2-methyl-4-oxo-1,4-dihydro-1,6-naphthyridin-5-yl)oxy)-N-methylacetamide |
| C-6 | 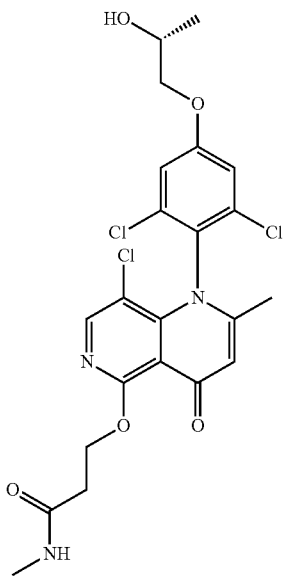 | (R)-3-((8-chloro-1-(2,6-dichloro-4-(2-hydroxypropoxy)phenyl)-2-methyl-4-oxo-1,4-dihydro-1,6-naphthyridin-5-yl)oxy)-N-methylpropanamide |

| Compound | Structure | Chemical Name |
|---|---|---|
| C-7 | 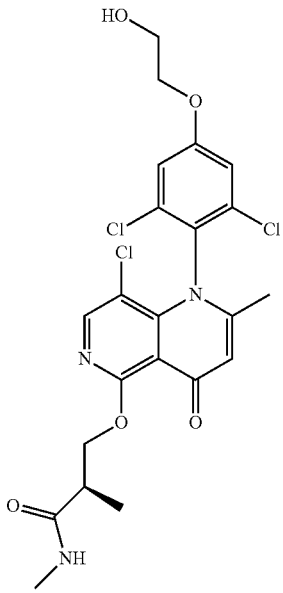 [SMILES: CNC(=O)[C@H](C)COc1ncc(Cl)c2c1c(=O)cc(C)n2-c1c(Cl)cc(OCCO)cc1Cl] | (R)-3-((8-chloro-1-(2,6-dichloro-4-(2-hydroxyethoxy)phenyl)-2-methyl-4-oxo-1,4-dihydro-1,6-naphthyridin-5-yl)oxy)-N,2-dimethylpropanamide |
| C-8 | 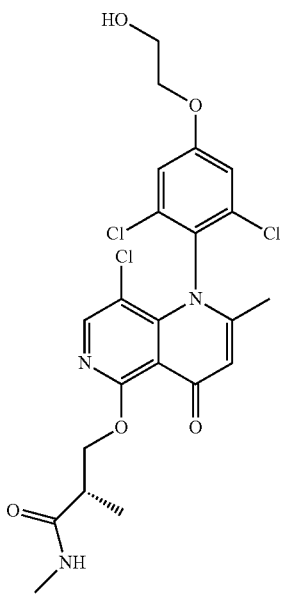 [SMILES: CNC(=O)[C@@H](C)COc1ncc(Cl)c2c1c(=O)cc(C)n2-c1c(Cl)cc(OCCO)cc1Cl] | (S)-3-((8-chloro-1-(2,6-dichloro-4-(2-hydroxyethoxy)phenyl)-2-methyl-4-oxo-1,4-dihydro-1,6-naphthyridin-5-yl)oxy)-N,2-dimethylpropanamide |

| Compound | Structure | Chemical Name |
|---|---|---|
| C-9 | 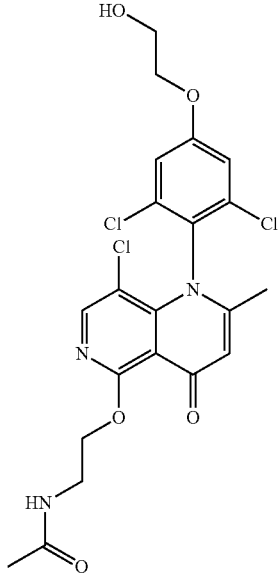 [SMILES: CC(=O)NCCOc1ncc(Cl)c2c1c(=O)cc(C)n2-c1c(Cl)cc(OCCO)cc1Cl] | N-(2-((8-chloro-1-(2,6-dichloro-4-(2-hydroxyethoxy)phenyl)-2-methyl-4-oxo-1,4-dihydro-1,6-naphthyridin-5-yl)oxy)ethyl)acetamide |
| C-10 | 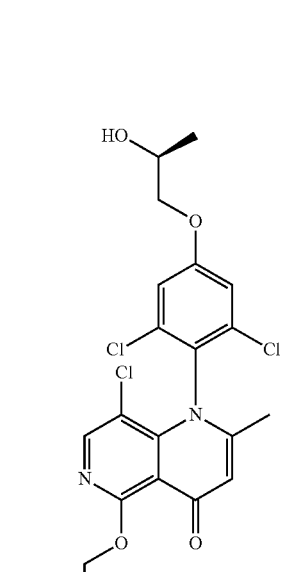 | (S)-3-((8-chloro-1-(2,6-dichloro-4-(2-hydroxypropoxy)phenyl)-2-methyl-4-oxo-1,4-dihydro-1,6-naphthyridin-5-yl)oxy)-N-methylpropanamide |

| Compound | Structure | Chemical Name |
|---|---|---|
| C-11 | 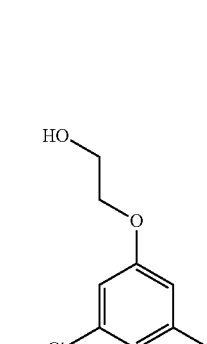 | 3-((8-chloro-1-(2,6-dichloro-4-(2-hydroxyethoxy)phenyl)-2-methyl-4-oxo-1,4-dihydro-1,6-naphthyridin-5-yl)oxy)-N,2,2-trimethylpropanamide |
| C-12 | 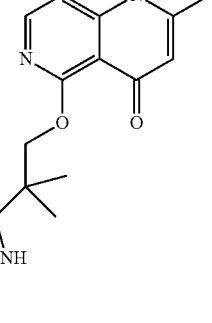 | (R)-3-((8-chloro-1-(2,6-dichloro-4-(2-hydroxyethoxy)phenyl)-2-methyl-4-oxo-1,4-dihydro-1,6-naphthyridin-5-yl)oxy)-2-hydroxy-N-methylpropanamide |

-continued
| Compound | Structure | Chemical Name |
|---|---|---|
| C-13 | 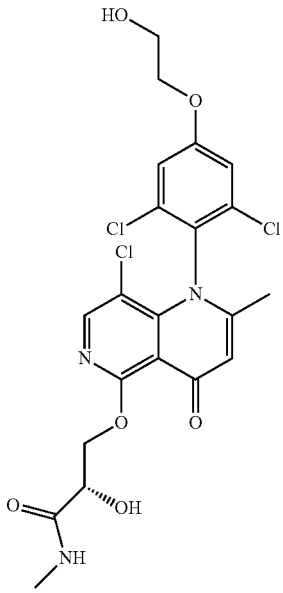 [SMILES: CNC(=O)[C@@H](O)COc1ncc(Cl)c2c1c(=O)cc(C)n2-c1c(Cl)cc(OCCO)cc1Cl] | (S)-3-((8-chloro-1-(2,6-dichloro-4-(2-hydroxyethoxy)phenyl)-2-methyl-4-oxo-1,4-dihydro-1,6-naphthyridin-5-yl)oxy)-2-hydroxy-N-methylpropanamide |
| C-14 | 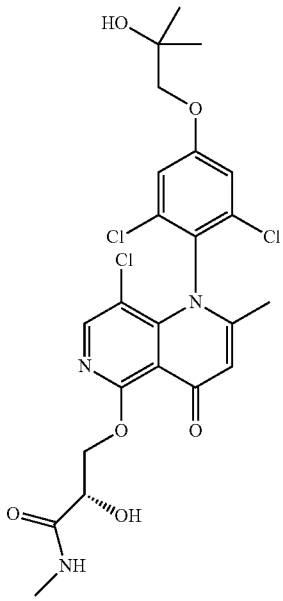 [SMILES: CNC(=O)[C@@H](O)COc1ncc(Cl)c2c1c(=O)cc(C)n2-c1c(Cl)cc(OCC(C)(C)O)cc1Cl] | (S)-3-((8-chloro-1-(2,6-dichloro-4-(2-hydroxy-2-methylpropoxy)phenyl)-2-methyl-4-oxo-1,4-dihydro-1,6-naphthyridin-5-yl)oxy)-2-hydroxy-N-methylpropanamide |

-continued
| Compound | Structure | Chemical Name |
|---|---|---|
| C-15 | 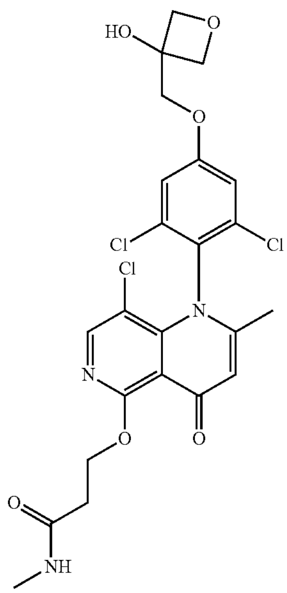 | 3-((8-chloro-1-(2,6-dichloro-4-((3-hydroxyoxetan-3-yl)methoxy)phenyl)-2-methyl-4-oxo-1,4-dihydro-1,6-naphthyridin-5-yl)oxy)-N-methylpropanamide |
| C-16 | 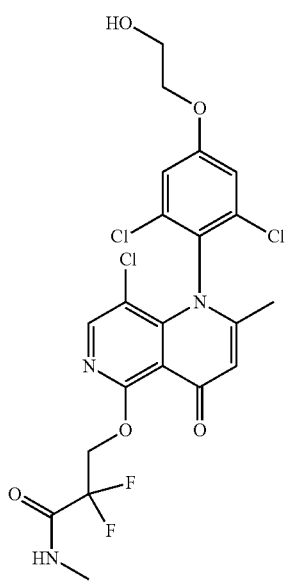 [SMILES: CNC(=O)C(F)(F)COc1ncc(Cl)c2c1c(=O)cc(C)n2-c1c(Cl)cc(OCCO)cc1Cl] | 3-((8-chloro-1-(2,6-dichloro-4-(2-hydroxyethoxy)phenyl)-2-methyl-4-oxo-1,4-dihydro-1,6-naphthyridin-5-yl)oxy)-2,2-difluoro-N-methylpropanamide |

| Compound | Structure | Chemical Name |
|---|---|---|
| C-17 | 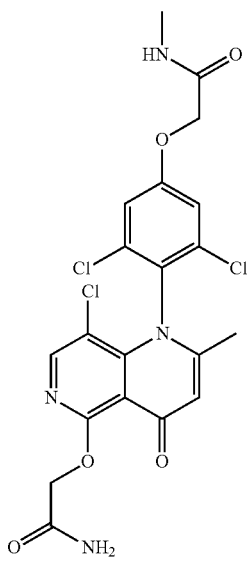 [SMILES: CNC(=O)COc1cc(Cl)c(-n2c(C)cc(=O)c3c(OCC(N)=O)ncc(Cl)c32)c(Cl)c1] | 2-(4-(5-(2-amino-2-oxoethoxy)-8-chloro-2-methyl-4-oxo-1,6-naphthyridin-1(4H)-yl)-3,5-dichlorophenoxy)-N-methylacetamide |
| C-18 | 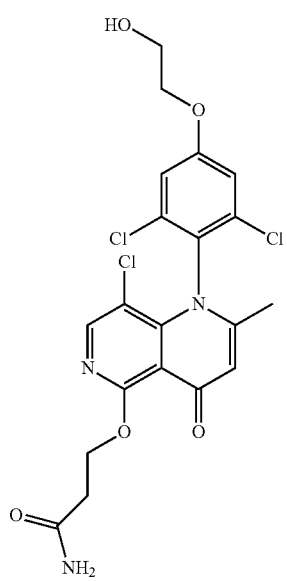 [SMILES: Cc1cc(=O)c2c(OCCC(N)=O)ncc(Cl)c2n1-c1c(Cl)cc(OCCO)cc1Cl] | 3-((8-chloro-1-(2,6-dichloro-4-(2-hydroxyethoxy)phenyl)-2-methyl-4-oxo-1,4-dihydro-1,6-naphthyridin-5-yl)oxy)propanamide |

-continued

| Compound | Structure | Chemical Name |
|---|---|---|
| C-19 | 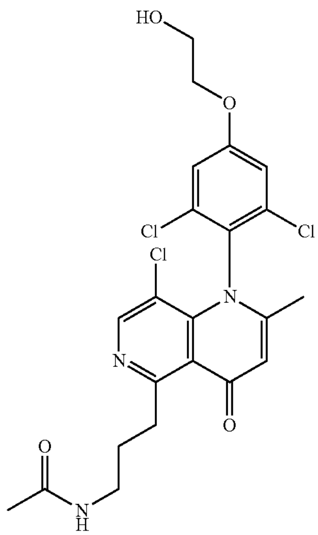 [SMILES: CC(=O)NCCCc1ncc(Cl)c2c1c(=O)cc(C)n2-c1c(Cl)cc(OCCO)cc1Cl] | N-(3-(8-chloro-1-(2,6-dichloro-4-(2-hydroxyethoxy)phenyl)-2-methyl-4-oxo-1,4-dihydro-1,6-naphthyridin-5-yl)propyl)acetamide |
| C-20 | 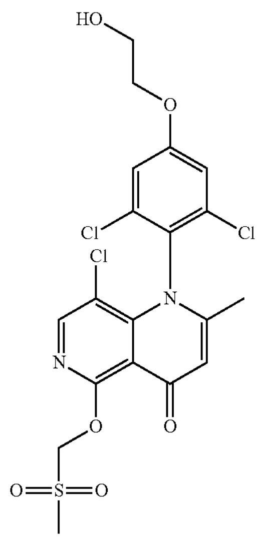 [SMILES: Cc1cc(=O)c2c(OCS(C)(=O)=O)ncc(Cl)c2n1-c1c(Cl)cc(OCCO)cc1Cl] | 8-chloro-1-(2,6-dichloro-4-(2-hydroxyethoxy)phenyl)-2-methyl-5-(2-(methylsulfonyl)ethyl)-1,6-naphthyridin-4(1H)-one |
| C-21 | 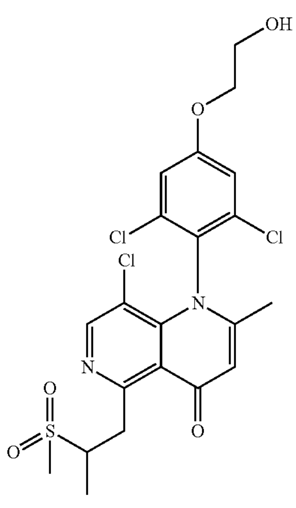 [SMILES: Cc1cc(=O)c2c(CC(C)S(C)(=O)=O)ncc(Cl)c2n1-c1c(Cl)cc(OCCO)cc1Cl] | 8-chloro-1-(2,6-dichloro-4-(2-hydroxyethoxy)phenyl)-2-methyl-5-(2-(methylsulfonyl)propyl)-1,6-naphthyridin-4(1H)-one |

| Compound | Structure | Chemical Name |
|---|---|---|
| C-22 | 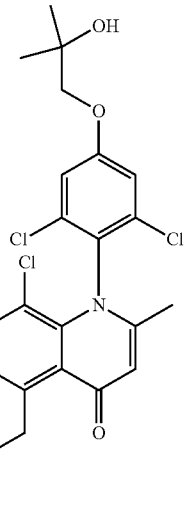 | 8-chloro-1-(2,6-dichloro-4-(2-hydroxy-2-methylpropoxy)phenyl)-2-methyl-5-(3-(methylsulfonyl)propyl)-1,6-naphthyridin-4(1H)-one |

As used herein, the terms "salt" or "salts" refers to an acid addition or base addition salt of a compound of the present invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto. When both a basic group and an acid group are present in the same molecule, the compounds of the present invention may also form internal salts, e.g., zwitterionic molecules.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present invention. The concentration of deuterium may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F $^{31}$P, $^{32}$P, $^{35}$S, $^{36}$Cl, $^{123}$I, $^{124}$I, $^{125}$I respectively. Accordingly, it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of the present invention can generally be prepared by conventional techniques known to those skilled in the art or by processes analogous to those described in the accompanying Examples and General Synthetic Schemes using an appropriate isotopically-labeled reagents in place of the non-labeled reagent previously employed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the present invention or racemic intermediates can also be resolved by chiral chromatography, e.g., high pressure liquid chromatography (HPLC) using a chiral adsorbent.

The compounds of formula (I) of the present invention, including free forms, pharmaceutically acceptable salts, hydrates and solvates thereof, may under the appropriate conditions be isolated in one or more crystalline forms.

The term "crystalline form" as used herein include reference to anhydrous crystalline forms, hydrate crystalline forms, solvate crystalline forms and mixtures of crystalline forms.

In one embodiment, a crystalline form of the compound of formula (I) or a pharmaceutically acceptable salt thereof according to the invention is selected from a free form, a hydrate, a solvate, a polymorph and a co-crystal thereof.

The term "free form" as used herein refers to the compound of formula (I) per se without salt formation or association with a solvent (e.g., solvate).

The term "hydrate" as used herein refers to a crystalline form containing one or more water molecules in a three-dimensional periodic arrangement. It can include non-stoichiometric hydrates or stoichiometric hydrates, such as hemihydrates, monohydrates, dihydrates and trihydrates.

The term "solvate" as used herein refers to a crystalline form containing one or more solvent molecules other than water in a three-dimensional periodic arrangement. The solvate may comprise either a stoichiometric or non-stoichiometric amount of the solvent molecules.

In one embodiment, the compounds of formula (I) or pharmaceutically acceptable salts thereof according to the present invention may inherently or by design form hydrates or solvates with pharmaceutically acceptable solvents.

The term "polymorph" as used herein refers to crystalline forms having the same chemical composition but different spatial arrangements of the molecules, atoms, and/or ions forming the crystal.

In one embodiment, compounds of formula (I) or pharmaceutically acceptable salts thereof according to the invention that contain groups capable of acting as donors and/or acceptors for hydrogen bonds may be capable of forming co-crystalline forms with suitable co-crystal formers.

The terms "co-crystalline" and "co-crystal" are used herein interchangeably to mean a co-crystal comprising a compound of formula (I) or a pharmaceutically acceptable salt thereof as defined herein and a suitable co-crystal former.

These co-crystals may be prepared from compounds of formula (I) or pharmaceutically acceptable salts thereof by known co-crystal forming procedures such as, e.g., grinding, heating, co-subliming, co-melting, or contacting in solution compounds of formula (I) or pharmaceutically acceptable salts thereof with a co-crystal former under crystallization conditions and isolating co-crystals thereby formed. Suitable co-crystal formers include, for instance, those described in WO 2004/078163.

In one embodiment, the present invention relates to a free crystalline form of a compound of formula (I) as defined herein.

In another embodiment, the present invention relates to a hydrate crystalline form of a compound of formula (I) or a pharmaceutically acceptable salt thereof as defined herein. In an aspect of this embodiment, the hydrate crystalline form of the compound of formula (I) or a pharmaceutically acceptable salt thereof as defined herein is a hemihydrate, monohydrate, dihydrate or trihydrate crystalline form.

In one embodiment, the present invention relates to a hydrate crystalline form of a compound of formula (I) as defined herein. In an aspect of this embodiment, the hydrate crystalline form of the compound of formula (I) as defined herein is a hemihydrate, monohydrate, dihydrate or trihydrate crystalline form.

In another embodiment, the present invention relates to a solvate crystalline form of a compound of formula (I) or a pharmaceutically acceptable salt thereof as defined herein.

In one embodiment, the present invention relates to a solvate crystalline form of a compound of formula (I) as defined herein with cyclopentanone.

In another embodiment, the present invention relates to a solvate crystalline form of a compound of formula (I) as defined herein with methanol.

In another embodiment, the present invention relates to a solvate crystalline form of a compound of formula (I) as defined herein with pyridine.

In another embodiment, the present invention relates to a co-crystal of a compound of formula (I) or a pharmaceutically acceptable salt thereof as defined herein.

In one embodiment, the present invention relates to a co-crystal comprising a compound of formula (I) or a pharmaceutically acceptable salt thereof as defined herein and a co-crystal former.

Preferably, the co-crystal former is selected from the group consisting of phosphoric acid, benzoic acid, succininc acid, saccharin and salts thereof.

In one embodiment of the present invention, there is provided a co-crystal comprising a compound of formula (I) or a pharmaceutically acceptable salt thereof as defined herein and phosphoric acid.

In another embodiment of the present invention, there is provided a co-crystal comprising a compound of formula (I) or a pharmaceutically acceptable salt thereof as defined herein and benzoic acid.

In another embodiment of the present invention, there is provided a co-crystal comprising a compound of formula (I) or a pharmaceutically acceptable salt thereof as defined herein and succinic acid.

In another embodiment of the present invention, there is provided a co-crystal comprising a compound of formula (I) or a pharmaceutically acceptable salt thereof as defined herein and saccharin.

The molar ratio of the compound of formula (I) or a pharmaceutically acceptable salt thereof to the co-crystal former in the co-crystals according to the invention may be stoichiometric or non-stoichiometric. For example, suitable molar ratios of the compound of formula (I) or a pharmaceutically acceptable salt thereof to the co-crystal former in the co-crystals according to the invention are from 1:2 to 2:1, preferably from 1.5:1 to 1:1.5, more preferably from 1:1.1 to 1.1:1.

In one embodiment, a crystalline form of the compound of formula (I) or a pharmaceutically acceptable salt thereof according to the invention is provided in substantially pure form. As used herein, "substantially pure," when used in reference to a crystalline form, means a compound having a purity greater than 90% by weight, including greater than 90, 91, 92, 93, 94, 95, 96, 97, 98, and 99% by weight, and also including equal to about 100% by weight of a compound of formula (I) or a pharmaceutically acceptable salt thereof, based on the weight of the compound. The remaining material comprises other form(s) of the compound of formula (I), and/or reaction impurities and/or processing impurities arising from its preparation. For example, a crystalline form of a compound of formula (I) or a pharmaceutically acceptable salt thereof according to the invention may be deemed substantially pure in that it has a purity greater than 90% by weight, as measured by means that are at this time known and generally accepted in the art, where the remaining less than 10% by weight of material comprises other form(s) of compound of formula (I) and/or reaction impurities and/or processing impurities.

A particular crystalline form of the compound of formula (I) or a pharmaceutically acceptable salt thereof according to the invention may be referred to as "crystalline form X", "crystal form X", "co-crystal form", "polymorph form X", "modification X", or "Hx" where 'X' is the letter which is assigned to that particular crystalline form. The names used herein to characterize a specific crystalline form, e.g. "A-1" etc., should not be considered limiting with respect to any other substance possessing similar or identical physical and chemical characteristics, but rather it should be understood that these designations are mere identifiers that should be interpreted according to the characterization information also presented herein.

In one embodiment, the present invention relates to a crystalline form of a compound of formula (I) or a pharmaceutically acceptable salt thereof as defined herein, wherein the crystalline form is selected from the various modifications detailed herein, preferably Modifications A-1, A-2, A-3, A-4, A-5, A-6, A-7, A-8, A-9, A-10, A-11, A-12 and A-13.

Each modification is characterized by its X-ray powder diffraction pattern with peaks as essentially depicted in the Figures. Thus, there is provided a crystalline form selected from the various modifications detailed herein, characterized in that said crystalline form has an X-ray powder diffraction pattern substantially in accordance with that shown in the corresponding FIG.

In further embodiments, the present invention provides any of the crystalline forms of the compound of formula (I) or a pharmaceutically acceptable salt thereof, as described in the Examples, in the form of a specific modification, characterized in that said crystalline form has at least one of the following characteristics:
  (a) an X-ray powder diffraction pattern substantially in accordance with that shown in the FIG. associated with that particular Modification; and/or
  (b) a melting point, as set out for each Modification in the Examples section; and/or
  (c) a differential scanning calorimetry thermogram, as set out for each Modification in the Examples section.

In one embodiment of the present invention, there is provided a free crystalline form of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) named Modification A-1, characterized in that said crystalline form has an X-ray powder diffraction pattern substantially in accordance with that shown in FIG. A1-1, or comprises four or more 2θ values (±0.1 degree), when measured using a CuKα radiation with a wavelength of 1.5418 Å at a temperature of about 22° C., selected from the 2θ values as set forth in the following table:

| No. | Angle 2θ | d value Å | Relative Intensity % |
|---|---|---|---|
| 1 | 7.7 | 11.47 | 99 |
| 2 | 11.3 | 7.86 | 5 |
| 3 | 15.4 | 5.74 | 10 |
| 4 | 16.4 | 5.40 | 32 |

-continued

| No. | Angle 2θ | d value Å | Relative Intensity % |
|---|---|---|---|
| 5 | 17.7 | 5.00 | 9 |
| 6 | 21.2 | 4.19 | 19 |
| 7 | 22.7 | 3.91 | 9 |
| 8 | 23.3 | 3.81 | 43 |
| 9 | 24.0 | 3.70 | 100 |
| 10 | 26.4 | 3.37 | 12 |
| 11 | 27.2 | 3.28 | 23 |

In another embodiment of the present invention, there is provided a hydrate crystalline form of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) named Modification A-2, characterized in that said crystalline form has an X-ray powder diffraction pattern substantially in accordance with that shown in FIG. A2-1, or comprises four or more 2θ values (+0.1 degree), when measured using a CuKα radiation with a wavelength of 1.5418 Å at a temperature of about 22° C., selected from the 2θ values as set forth in the following table:

| No. | Angle 2θ | d value Å | Relative Intensity % |
|---|---|---|---|
| 1 | 7.6 | 11.62 | 17 |
| 2 | 10.7 | 8.30 | 3 |
| 3 | 15.2 | 5.81 | 4 |
| 4 | 16.9 | 5.24 | 27 |
| 5 | 21.4 | 4.15 | 17 |
| 6 | 24.0 | 3.70 | 100 |
| 7 | 25.8 | 3.45 | 3 |
| 8 | 27.4 | 3.26 | 17 |
| 9 | 30.7 | 2.91 | 2 |

In another embodiment of the present invention, there is provided a hydrate crystalline form of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) named Modification A-3, characterized in that said crystalline form has an X-ray powder diffraction pattern substantially in accordance with that shown in FIG. A3-1, or comprises four or more 2θ values (+0.1 degree), when measured using a CuKα radiation with a wavelength of 1.5418 Å at a temperature of about 22° C., selected from the 2θ values as set forth in the following table:

| No. | Angle 2θ | d value Å | Relative Intensity % |
|---|---|---|---|
| 1 | 7.6 | 11.55 | 23 |
| 2 | 15.3 | 5.78 | 9 |
| 3 | 17.0 | 5.22 | 18 |
| 4 | 20.7 | 4.29 | 5 |
| 5 | 21.4 | 4.14 | 8 |
| 6 | 22.2 | 3.99 | 33 |
| 7 | 25.9 | 3.44 | 20 |
| 8 | 29.1 | 3.07 | 10 |
| 9 | 32.3 | 2.77 | 12 |

In another embodiment of the present invention, there is provided a hydrate crystalline form of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) named Modification A-4, characterized in that said crystalline form has an X-ray powder diffraction pattern substantially in accordance with that shown in FIG. A4-1, or comprises four or more 2θ values (±0.1 degree), when measured using a CuKα radiation with a wavelength of 1.5418 Å at a temperature of about 22° C., selected from the 2θ values as set forth in the following table:

| No. | Angle 2θ | d value Å | Relative Intensity % |
|---|---|---|---|
| 1 | 7.3 | 12.11 | 29 |
| 2 | 10.3 | 8.59 | 3 |
| 3 | 15.5 | 5.73 | 10 |
| 4 | 22.1 | 4.02 | 3 |
| 5 | 23.1 | 3.84 | 100 |
| 6 | 23.9 | 3.73 | 19 |
| 7 | 25.5 | 3.49 | 7 |
| 8 | 25.9 | 3.44 | 6 |
| 9 | 26.4 | 3.37 | 50 |
| 10 | 31.2 | 2.86 | 8 |

In another embodiment of the present invention, there is provided a hydrate crystalline form of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) named Modification A-5, characterized in that said crystalline form has an X-ray powder diffraction pattern substantially in accordance with that shown in FIG. A5-1, or comprises four or more 2θ values (±0.1 degree), when measured using a CuKα radiation with a wavelength of 1.5418 Å at a temperature of about 22° C., selected from the 2θ values as set forth in the following table:

| No. | Angle 2θ | d value Å | Relative Intensity % |
|---|---|---|---|
| 1 | 5.0 | 17.84 | 47 |
| 2 | 9.9 | 8.93 | 14 |
| 3 | 14.9 | 5.96 | 21 |
| 4 | 15.9 | 5.58 | 39 |
| 5 | 17.7 | 5.01 | 14 |
| 6 | 19.8 | 4.47 | 87 |
| 7 | 24.0 | 3.71 | 84 |
| 8 | 25.5 | 3.49 | 68 |
| 9 | 27.2 | 3.28 | 23 |

Pharmaceutical Compositions

In another aspect, the present invention provides a pharmaceutical composition comprising a compound of the present invention, or a pharmaceutically acceptable salt thereof, and one or more pharmaceutically acceptable carriers. In a further embodiment, the composition comprises at least two pharmaceutically acceptable carriers, such as those described herein.

In some embodiments, a pharmaceutical composition further comprises at least one additional pharmaceutically active agent. In some embodiments, the additional pharmaceutically active agent is selected from Class I antiarrhythmic agents, Class II antiarrhythmic agents, Class III antiarrhythmic agents, Class IV antiarrhythmic agents, Class V antiarrhythmic agents, cardiac glycosides and other drugs affecting atrial refractoriness; haemostasis modulators, antithrombotics; thrombin inhibitors; factor VIIa inhibitors; anticoagulants, factor Xa inhibitors, and direct thrombin inhibitors; antiplatelet agents, cyclooxygenase inhibitors, adenosine diphosphate (ADP) receptor inhibitors, phosphodiesterase inhibitors, glycoprotein IIB/IIA, adenosine reuptake inhibitors; anti-dyslipidemia agents, HMG-CoA reductase inhibitors, other cholesterol-lowering agents; bile acid sequestrants; cholesterol absorption inhibitors; cholesteryl ester transfer protein (CETP) inhibitors; inhibitors of the ileal bile acid transport system (IBAT inhibitors); bile acid binding resins; nicotinic acid and analogues thereof, anti-oxidants; omega-3 fatty acids; antihypertensive agents, including adrenergic receptor antagonists, beta blockers, alpha blockers, mixed alpha/beta blockers; adrenergic receptor agonists, alpha-2 agonists; angiotensin converting enzyme (ACE) inhibitors, calcium channel blockers; angiotensin II receptor antagonists; aldosterone receptor antagonists; centrally acting adrenergic drugs, central alpha agonists; and diuretic agents; anti-obesity agents, pancreatic lipase inhibitors, microsomal transfer protein (MTP) modulators, diacyl glycerolacyltransferase (DGAT) inhibitors, cannabinoid (CBI) receptor antagonists; insulin and insulin analogues; insulin secretagogues; agents that improve incretin action, dipeptidyl peptidase IV (DPP-4) inhibitors, glucagon-like peptide-I (GLP-1) agonists; insulin sensitizing agents, peroxisome proliferator activated receptor gamma (PPARγ) agonists, agents that modulate hepatic glucose balance, fructose 1,6-bisphosphatase inhibitors, glycogen phosphorylase inhibitors, glycogen synthase kinase inhibitors, glucokinase activators; agents designed to reduce/slow the absorption of glucose from the intestine, alpha-glucosidase inhibitors; agents which antagonize the actions of or reduce secretion of glucagon, amylin analogues; agents that prevent the reabsorption of glucose by the kidney, and sodium-dependent glucose transporter 2 (SGLT-2) inhibitors and combinations thereof.

The pharmaceutical composition can be formulated for particular routes of administration such as oral administration, parenteral administration (e.g., by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and
  e) absorbents, colorants, flavors and sweeteners.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions, using polyalkylene glycols such as propylene glycol, as the carrier.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

The pharmaceutical composition or combination of the present invention may, for example, be in unit dosage of about 1-1000 mg of active ingredient(s) for a subject of about 50-70 kg. In one embodiment, the compositions are in the form of a tablet that can be scored. The therapeutically effective dosage of a compound, the pharmaceutical composition, or the combinations thereof, is dependent on the species of the subject, the body weight, age and individual condition, the disorder or disease or the severity thereof being treated.

Methods of Use

In yet another aspect, the present invention is directed to a method of treating or preventing a disease or disorder comprising administering to a patient in need thereof an effective amount of a compound of formula (I), or a pharmaceutically acceptable salt thereof or a pharmaceutical composition comprising a compound of formula (I), or a pharmaceutically acceptable salt thereof, and a pharmaceutically acceptable carrier.

In another aspect, the present invention relates to a method for treating a disease or disorder comprising administering to a patient in need thereof an effective amount of a compound of formula (I), or a pharmaceutically acceptable salt thereof, or a pharmaceutical composition comprising a compound of formula (I), or a pharmaceutically acceptable salt thereof, and a pharmaceutically acceptable carrier, wherein the disease or disorder is selected from cardiac arrhythmia, atrial fibrillation, bradyarrhythmia, bradycardia, heart block, sick sinus syndrome, parasympathetic hyperactivation, primary hyperaldosteronism, hypotension, and vasovagal syncope.

In another aspect, the present invention relates to a method for maintaining a sinus rhythm after cardioversion in a patient with persistent or recent onset of atrial fibrillation or preventing a recurrence in a patient with paroxysmal atrial fibrillation, the method comprising administering to a patient in need thereof a therapeutically effective amount of a compound of formula (I), or a pharmaceutically acceptable salt thereof or a pharmaceutical composition comprising a compound of formula (I), or a pharmaceutically acceptable salt thereof, and a pharmaceutically acceptable carrier.

In another aspect, the present invention relates to a compound of formula (I), or a pharmaceutically acceptable salt thereof for use a medicament.

Another aspect of the present invention relates to a compound of formula (I), or a pharmaceutically acceptable salt thereof, or a pharmaceutical composition comprising a compound of formula (I), or a pharmaceutically acceptable salt thereof, and a pharmaceutically acceptable carrier for use in the in the treatment of a disease or disorder responsive to the inhibition of the GIRK1/4 receptor.

In another aspect, the present invention relates to a compound of formula (I), or a pharmaceutically acceptable salt thereof, or a pharmaceutical composition comprising a compound of formula (I), or a pharmaceutically acceptable salt, thereof, and a pharmaceutically acceptable carrier for use in the treatment, prevention, inhibition, or elimination of a disease or disorder, wherein the disease or disorder is selected from cardiac arrhythmia, atrial fibrillation, bradyarrhythmia, bradycardia, heart block, sick sinus syndrome, parasympathetic hyperactivation, primary hyperaldosteronism, hypotension, and vasovagal syncope.

In another aspect, the present invention relates to a compound of formula (I), or a pharmaceutically acceptable salt thereof, or a pharmaceutical composition comprising a compound of formula (I), or a pharmaceutically acceptable salt, thereof, and a pharmaceutically acceptable carrier for use in maintaining a sinus rhythm after cardioversion in a patient with persistent or recent onset of atrial fibrillation or preventing a recurrence in a patient with paroxysmal atrial fibrillation.

Another aspect of the present invention relates to the use of a compound of formula (I), or a pharmaceutically acceptable salt thereof, or a pharmaceutical composition comprising a compound of formula (I), or a pharmaceutically acceptable salt thereof, and a pharmaceutically acceptable carrier in the manufacture of a medicament treating a disease or disorder responsive to the inhibition of the GIRK1/4 receptor.

In another aspect, the present invention relates to the use of a compound of formula (I), or a pharmaceutically acceptable salt thereof, or a pharmaceutical composition comprising a compound of formula (I), or a pharmaceutically acceptable salt thereof, and a pharmaceutically acceptable carrier in the treatment of a disease or disorder, wherein the disease or disorder is selected from cardiac arrhythmia, atrial fibrillation, bradyarrhythmia, bradycardia, heart block, sick sinus syndrome, parasympathetic hyperactivation, primary hyperaldosteronism, hypotension, and vasovagal syncope.

In another aspect, the present invention relates to the use of a compound of formula (I), or a pharmaceutically acceptable salt thereof, or a pharmaceutical composition comprising a compound of formula (I), or a pharmaceutically acceptable salt thereof, and a pharmaceutically acceptable carrier in maintaining a sinus rhythm after cardioversion in a patient with persistent or recent onset of atrial fibrillation or preventing a recurrence in a patient with paroxysmal atrial fibrillation.

In certain embodiments, the disease or disorder is a disease or disorder responsive to the inhibition of the GIRK1/4 receptor. In some embodiments, the disease or disorder responsive to the inhibition of the GIRK1/4 receptor is selected from cardiac arrhythmia, atrial fibrillation, bradyarrhythmia, bradycardia, heart block, sick sinus syndrome, parasympathetic hyperactivation, primary hyperaldosteronism, hypotension, and vasovagal syncope.

In some embodiments, the disease or disorder is selected from cardiac arrhythmia, atrial fibrillation, bradyarrhythmia, bradycardia, heart block, sick sinus syndrome, parasympathetic hyperactivation, primary hyperaldosteronism, hypotension, and vasovagal syncope.

The disclosed compounds of the invention can be administered in effective amounts to treat or prevent a disorder and/or prevent the development thereof in subjects.

In some embodiments, administering the compound is orally.

Combination Therapy

The compounds of the invention can be administered in therapeutically effective amounts in a combinational therapy with one or more pharmaceutically active agents (pharmaceutical combinations) or modalities, e.g., non-drug therapies. For example, synergistic effects can occur with other cardiovascular agents, antihypertensive agents, coronary vasodilators, and diuretic substances. Where the compounds of the application are administered in conjunction with other therapies, dosages of the co-administered compounds will of course vary depending on the type of co-drug employed, on the specific drug employed, on the condition being treated and so forth.

The compounds of the present invention may be administered either simultaneously with, or before or after, one or more other pharmaceutically active agent. The compound of the present invention may be administered separately, by the same or different route of administration, or together in the same pharmaceutical composition as the other agents. A pharmaceutically active agent is, for example, a chemical compound, peptide, antibody, antibody fragment or nucleic acid, which is therapeutically active or enhances the therapeutic activity when administered to a patient in combination with a compound of the present invention.

In one embodiment, the invention provides a product comprising a compound of the present invention and at least one other pharmaceutically active agent as a combined preparation for simultaneous, separate or sequential use in therapy. In one embodiment, the therapy is the treatment of is a disease or disorder responsive to the inhibition of the GIRK1/4 receptor. Products provided as a combined preparation include a composition comprising the compound of the present invention and the other pharmaceutically active agent(s) together in the same pharmaceutical composition as described herein, or the compound of the present invention and the other pharmaceutically active agent (s) in separate form, e.g., in the form of a kit.

In another aspect, the invention includes a compound of formula (I) or a pharmaceutically acceptable salt thereof, for use in a combination therapy.

Another aspect of the invention is directed to pharmaceutical compositions comprising a compound of formula (I), or a pharmaceutically acceptable salt thereof, a pharmaceutically acceptable carrier, and one or more pharmaceutically active agent. The pharmaceutical acceptable carrier may further include an excipient, diluent, or surfactant.

Combination therapy includes the administration of the subject compounds in further combination with other biologically active ingredients. For instance, the compounds of the application can be used in combination with other pharmaceutically active agents, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

Exemplary additional pharmaceutically active agents that may be used in combination with the compounds of the invention, include, but are not limited to, any other antiarrhythmic agent, such as Class I antiarrhythmic agents (e.g., quinidine, lidocaine, and propafenone), Class II antiarrhythmic agents (e.g., propranolol), Class III antiarrhythmic agents (e.g., sotalol, dofetilide, amiodarone, dronedarone, budiodarone, azimilide and ibutilide), Class IV antiarrhythmic agents (e.g., diltiazem and verapamil), Class V antiarrhythmic agents (e.g., adenosine), cardiac glycosides (e.g., *digitalis* and ouabain) and other drugs affecting atrial refractoriness (e.g., $I_{Na,Late}$ blockers such as described in WO 2013/112932); haemostasis modulators, including antithrombotics such as activators of fibrinolysis; thrombin inhibitors; factor VIIa inhibitors; anticoagulants, such as vitamin K antagonists (e.g., warfarin), heparin and low molecular weight analogues thereof (e.g., dalteparin), factor Xa inhibitors (e.g., rivaroxaban and apixaban), and direct thrombin inhibitors (e.g., argatroban); antiplatelet agents, such as cyclooxygenase inhibitors (e.g., aspirin and NSAIDs), adenosine diphosphate (ADP) receptor inhibitors (e.g., clopidogrel), phosphodiesterase inhibitors (e.g., cilostazol), glycoprotein IIB/IIA inhibitors (e.g., tirofiban), and adenosine reuptake inhibitors (e.g., dipyridamole); anti-dyslipidemia agents, such as HMG-CoA reductase inhibitors (statins) and other cholesterol-lowering agents; PPARα agonists (fibrates, e.g., gemfibrozil and fenofibrate); bile acid sequestrants (e.g., cholestyramine); cholesterol absorption inhibitors (e.g., plant sterols (i.e., phytosterols), synthetic inhibitors); cholesteryl ester transfer protein (CETP) inhibitors; inhibitors of the ileal bile acid transport system (IBAT inhibitors); bile acid binding resins; nicotinic acid (niacin) and analogues thereof, anti-oxidants; and omega-3 fatty acids; antihypertensive agents, including adrenergic receptor antagonists, such as beta blockers (e.g., atenolol), alpha blockers (e.g., doxazosin), and mixed alpha/beta blockers (e.g., labetalol); adrenergic receptor agonists, including alpha-2 agonists (e.g., clonidine); angiotensin converting enzyme (ACE) inhibitors (e.g., lisinopril), calcium channel blockers, such as dihydropyridines (e.g., nifedipine), phenylalkylamines (e.g., verapamil), and benzothiazepines (e.g., diltiazem); angiotensin II receptor antagonists (e.g., losartan); aldosterone receptor antagonists (e.g., eplerenone); centrally acting adrenergic drugs, such as central alpha agonists (e.g., clonidine); and diuretic agents (e.g., furosemide); anti-obesity agents, such as appetite suppressant (e.g., ephedrine), including noradrenergic agents (e.g., phentermine) and serotonergic agents (e.g., sibutramine), pancreatic lipase inhibitors (e.g., orlistat), microsomal transfer protein (MTP) modulators, diacyl glycerolacyltransferase (DGAT) inhibitors, and cannabinoid (CBI) receptor antagonists (e.g., rimonabant); insulin and insulin analogues; insulin secretagogues, including sulphonylureas (e.g., glipizide) and prandial glucose regulators (sometimes called "short-acting secretagogues"), such as meglitinides (e.g., repaglinide and nateglinide); agents that improve incretin action, for example dipeptidyl peptidase IV (DPP-4) inhibitors (e.g., vildagliptin, sitagliptin, LAF237, MK-431), and glucagon-like peptide-I (GLP-1) agonists (e.g., exenatide); insulin sensitising agents including peroxisome proliferator activated receptor gamma (PPARγ) agonists, such as thiazolidinediones (e.g., pioglitazone and rosiglitazone), and agents with any combination of PPAR alpha, gamma and delta activity; agents that modulate hepatic glucose balance, for example biguanides (e.g., metformin), fructose 1,6-bisphosphatase inhibitors, glycogen phopsphorylase inhibitors, glycogen synthase kinase inhibitors, and glucokinase activators; agents designed to reduce/slow the absorption of glucose from the intestine, such as alpha-glucosidase inhibitors (e.g., miglitol and acarbose); agents which antagonise the actions of or reduce secretion of glucagon, such as amylin analogues (e.g., pramlintide); agents that prevent the reabsorption of glucose by the kidney, such as sodium-dependent glucose transporter 2 (SGLT-2) inhibitors.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, pharmaceutically acceptables salt thereof.

An angiotensin II receptor antagonist or a pharmaceutically acceptable salt thereof is understood to be an active ingredient which bind to the AT1-receptor subtype of angiotensin II receptor but do not result in activation of the receptor. As a consequence of the inhibition of the $AT_1$ receptor, these antagonists can, for example, be employed as antihypertensives or for treating congestive heart failure.

The term "diuretic" includes thiazide derivatives (e.g., chlorothiazide, hydrochlorothiazide, methylclothiazide, and chlorothalidon).

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal. The DPP-IV inhibitor can be peptidic or, preferably, non-peptidic. DPP-IV inhibitors include but are not limited to sitagliptin, linagliptin, saxagliptin, and alogliptin. DPP-IV inhibitors are also generically and specifically disclosed e.g., in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in Diabetologia, 28, 1985, 704-707 and in U.S. Pat. No. 5,705,483. The term "GLP-1 agonists" includes variants and analogs of GLP-1(7-36)NH$_2$ which are disclosed in particular in U.S. Pat. Nos. 5,120,712, 5,118,666, 5,512,549, WO 91/11457 and by C. Orskov et al in J. Biol. Chem. 264 (1989) 12826. Further examples include GLP-1(7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP-1(7-37), GLY$^8$-GLP-1(7-37), THR-GLP-1(7-37), MET$^8$-GLP-1(7-37) and 4-imidazopropionyl-GLP-1. GLP-1 receptor agonists include, but are not limited to, semaglutide, exenatide, and liraglutide.

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the latter being most preferred.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole.

A preferred steroidal aldosterone antagonist is eplerenone or Spironolactone; or, in each case, if appropriable, a pharmaceutically acceptable salt thereof.

Aldosterone synthase inhibitors useful in said combination are compounds and analogs generically and specifically disclosed e.g., in US 2007/0049616, in particular in the compound claims and the final products of the working examples, the subject-matter of the final products, the pharmaceutical preparations and the claims are hereby incorporated into the present application by reference to this publication.

The term aldosterone synthase inhibitors also include compounds and analogs disclosed in WO 2008/076860, WO 2008/076336, WO 2008/076862, WO 2008/027284, WO 2004/046145, WO 2004/014914, WO 2001/076574.

Furthermore, aldosterone synthase inhibitors also include compounds and analogs disclosed in U.S. patent applications US 2007/0225232, US 2007/0208035, US 2008/0318978, US 2008/0076794, US 2009/0012068, US 2009/0048241 and in PCT applications WO 2006/005726, WO 2006/128853, WO 2006/128851, WO 2006/128852, WO 2007/065942, WO 2007/116099, WO 2007/116908, WO 2008/119744 and in European patent application EP 1886695.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. Nos. 6,140,343 and 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett.*; 6:1951-1954 (1996), respectively. Furthermore, the CETP inhibitors also include those disclosed in WO 2000/017165, WO 2005/095409 and WO 2005/097806.

In another embodiment, the other therapeutic agent is selected from any other antiarrhythmic agent, such as Class I antiarrhythmic agents (e.g., quinidine, lidocaine, and propafenone), Class II antiarrhythmic agents (e.g., propranolol), Class III antiarrhythmic agents (e.g., sotalol, dofetilide, amiodarone, dronedarone, budiodarone, azimilide and ibutilide), Class IV antiarrhythmic agents (e.g., diltiazem and verapamil), Class V antiarrhythmic agents (e.g., adenosine), cardiac glycosides (e.g., *digitalis* and ouabain) and other drugs affecting atrial refractoriness (e.g., $I_{Na,Late}$ blockers such as described in WO 2013/112932).

"Combination therapy" is intended to embrace administration of these therapeutic agents in a sequential manner, wherein each therapeutic agent is administered at a different time and in any order, or in alternation and in any order, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

Methods for the Preparation of Compounds of Formula (I)

The compounds of formula (I) of the present invention may be made by a variety of methods, including standard chemistry. Suitable synthetic routes are depicted in the Schemes given below.

The compounds of formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formula (I).

Those skilled in the art will recognize if a stereocenter exists in the compounds of formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Definitions

Terms not specifically defined herein should be given the meanings that would be given to them by one of skill in the art in light of the invention and the context. For purposes of interpreting this specification, the following definitions will apply unless specified otherwise and whenever appropriate, terms used in the singular will also include the plural and vice versa.

It must be noted that as used herein and in the appended claims, the singular forms "a", "an" and "the" include plural referents unless the context clearly dictates otherwise. Thus, for example, reference to "the pharmaceutical formulation" includes reference to one or more pharmaceutical formulations; and so forth.

The term "acyl", as used herein, refers to a group represented by the general formula hydrocarbylC(O)—, preferably alkylC(O)—.

The term "acyloxy", as used herein, refers to a group represented by the general formula hydrocarbylC(O)O—, preferably alkylC(O)O—.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. Examples of alkenyl groups include ethenyl, propenyl, n-butenyl, iso-butenyl, pentenyl, or hexenyl.

The term "alkoxy", as used herein, refers to an alkyl group, preferably a lower alkyl group, having an oxygen attached thereto, e.g., —O(alkyl). Representative alkoxy groups include, but are not limited to, methoxy, ethoxy, propoxy, tert-butoxy and the like. Representative substituted alkoxy groups include, but are not limited to, —OCF$_3$ and the like.

An "alkyl" group or "alkane" is a straight chained or branched, non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl tert-butyl, pentyl, hexyl, pentyl and octyl. A $C_1$-$C_6$ straight chained, or branched alkyl group is also referred to as a "lower alkyl" group.

The term "alkynyl", as used herein, refers to an aliphatic group containing at least one triple bond. Examples of alkynyl groups include ethynyl, propargyl, n-butynyl, iso-butynyl, pentynyl, or hexynyl.

The term "aryl", as used herein, include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. Co alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described herein, but that contain at least one double or triple bond respectively.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring.

Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings.

The terms "halo" and "halogen", as used herein, means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, but are not limited to, furyl, thienyl, pyrrolyl, pyridyl, pyridyl N-oxide, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1A2-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4 d]thiazolyl, imidazo[2,1-b][1,3,4]thiadiazolyl, thieno[2,3-b]pyrrolyl, 3H-indolyl, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

"Haloalkyl", as used herein, refers to an alkyl group substituted with one or more halogens. Examples of haloalkyl groups include, but are not limited to, trifluoromethyl, difluoromethyl, pentafluoroethyl, trichloromethyl, etc.

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The term "optionally substituted" means that a given chemical moiety (e.g., an alky 1 group) can (but is not required to) be bonded to other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen, wherein the substituents are as defined herein. "Optionally substituted" as used herein also refers to substituted or unsubstituted whose meaning is described below.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

The term "unsubstituted" means that the specified group bears no substituents.

A "patient" or "subject" is a mammal, e.g., a human, mouse, rat, guinea pig, dog, cat, horse, cow, pig, or nonhuman primate, such as a monkey, chimpanzee, baboon or, rhesus. In certain embodiments, the subject is a primate. In yet other embodiments, the subject is a human.

The terms "pharmaceutically effective amount" or "therapeutically effective amount" or "effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this invention.

As used herein, the term "pharmaceutical composition" refers to a compound of the invention, or a pharmaceutically acceptable salt, hydrate, solvate, stereoisomer, or tautomer thereof, together with at least one pharmaceutically acceptable carrier, in a form suitable for oral or parenteral administration.

"Carrier" encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

"Combination" refers to either a fixed combination in one dosage unit form, or a combined administration where a compound of the present invention and at least one combination partner (e.g., another drug as explained below, also referred to as "therapeutic agent" or "co-agent") may be administered independently at the same time or separately within time intervals, especially where these time intervals allow that the combination partners show a beneficial effect from the co-action of these therapeutic agents. The beneficial effect of the combination includes, but is not limited to, a cooperative, e.g., synergistic, effect and/or a pharmacokinetic or pharmacodynamic co-action, or any combination thereof, resulting from the combination of therapeutic agents. In one embodiment, administration of these therapeutic agents in combination is carried out over a defined time period (e.g., minutes, hours, days or weeks depending upon the combination selected).

The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time.

The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g., a compound of the present invention and a combination partner, are both administered to a patient simultaneously in the form of a single entity or dosage. The term "non-fixed combination" means that the therapeutic agents, e.g., a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more therapeutic agents.

A subject is "in need of" a treatment if such subject would benefit biologically, medically, or in quality of life from such treatment (preferably, a human).

As used herein, the term "inhibit", "inhibition", or "inhibiting" refers to the reduction or suppression of a given condition, symptom, or disorder, or disease, or a significant decrease in the baseline activity of a biological activity or process.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder.

"Pharmaceutically acceptable" means that the substance or composition must be compatible chemically and/or toxicologically, with the other ingredients comprising a formulation, and/or the mammal being treated therewith.

"Disorder" means, and is used interchangeably with, the terms disease, condition, or illness, unless otherwise indicated.

"Administer", "administering", or "administration" means to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

"Compounds of the present invention", "Compounds of formula (I)", "compounds of the invention", and equivalent expressions (unless specifically identified otherwise) refer to compounds of formulae (I) and (Ia) as herein described including the salts particularly the pharmaceutically acceptable salts thereof, where the context so permits thereof, as well as all stereoisomers (including diastereoisomers and enantiomers), rotamers, tautomers, and isotopically labelled compounds (including deuterium ("D") substitutions).

In a specific embodiment, the term "about" or "approximately" means within 20%, preferably within 10%, and more preferably within 5% of a given value or range.

As used herein, "disorders or diseases responsive to the inhibition of the GIRK1/4 receptor" and "disorders responsive to the inhibition of the GIRK1/4 receptor," and like terms include, but are not limited to, cardiac arrhythmia, atrial fibrillation, bradyarrhythmia, bradycardia, heart block, sick sinus syndrome, parasympathetic hyperactivation, primary hyperaldosteronism, hypotension, and vasovagal syncope.

EXAMPLES

The invention is further illustrated by the following examples and synthesis schemes, which are not to be construed as limiting this invention in scope or spirit to the specific procedures herein described. It is to be understood that the examples are provided to illustrate certain embodiments and that no limitation to the scope of the invention is intended thereby. It is to be further understood that resort may be had to various other embodiments, modifications, and equivalents thereof which may suggest themselves to those skilled in the art without departing from the spirit of the present invention and/or scope of the appended claims.

Compounds of the present invention may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3rd edition, John Wiley & Sons). These groups are removed at a convenient stage of the compound synthesis using methods that are readily apparent to those skilled in the art.

Unless otherwise noted, reagents and solvents were used as received from commercial suppliers. Proton nuclear magnetic resonance (NMR) spectra were obtained on either Bruker Avance spectrometer or Varian Oxford 400 MHz spectrometer unless otherwise noted. NMR spectra are given in ppm (δ) and coupling constants, J, are reported in Hertz. Tetramethylsilane (TMS) was used as an internal standard. Chemical shifts are reported in ppm relative to dimethyl sulfoxide (δ2.50), methanol (δ3.31), chloroform (δ7.26) or other solvent as indicated in NMR spectral data. A small amount of dry sample (2-5 mg) is dissolved in an appropriate deuterated solvent (1 mL). Mass spectra (ESI-MS) were collected using a Waters System (Acquity UPLC and a Micromass ZQ mass spectrometer) or Agilent-1260 Infinity (6120 Quadrupole); all masses reported are the m/z of the protonated parent ions unless recorded otherwise. The chemical names were generated using ChemBioDraw Ultra v14 from CambridgeSoft.

Temperatures are given in degrees Celsius. As used herein, unless specified otherwise, the term "room temperature" or "ambient temperature" means a temperature of from 15 degrees centigrade to 30 degrees centigrade, such as of from 20 degrees centigrade to 30 degrees centigrade, such as of from 20 degrees centigrade to 25 degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art.

TABLE 1

Abbreviations used in the following examples and elsewhere herein are:

| | | | |
|---|---|---|---|
| ACN | acetonitrile | aq. | aqueous |
| 9-BBN | 9-borabicyclo[3.3.1]nonane | BOC | tert-butyloxycarbonyl |
| br | broad | bs | broad singlet |
| ° C. | degrees celsius | conc. | concentrated |
| δ | NMR chemical shift in ppm downfield from tetramethylsilane | d | doublet |
| DCE | 1,2-dichloroethane | DCM | dichloromethane |
| DEA | diethylamine | DIPEA | N,N-diisopropylethylamine |
| DMA | dimethylacetamide | DMAP | 4-(dimethylamino)pyridine |
| DME | dimethoxyethane | DMF | N,N-dimethylformamide |
| DMSO | dimethylsulfoxide | DPPF | 1,1'-bis(diphenylphosphino)ferrocene |
| Et | ethyl | EtOAc | ethyl acetate |
| g | gram | h(r) | hour |
| HEPES | (4-(2-hydroxyethyl)-1-piperazineethanesulfonic acid | HATU | O-(7-azabenzotriazol-1-yl)-N,N,N',N'-tetramethyluronium hexafluorophosphate |
| HRMS | high-resolution mass spectrometry | i-Pr | isopropyl |
| L | liter | LDA | lithium diethylamide |
| LC/MS | liquid chromatography-mass spectrometry | M | molarity |
| m | multiplet | Me | methyl |
| mg | milligram | MHz | megahertz |
| min | minute | mL | milliliter |
| μL | microliter | mmol | millimole |
| N | normal | NBS | N-bromosuccinimide |
| NCS | N-chlorosuccinimide | n-Bu | normal butyl |
| n-BuLi | n-butyllithium | NMM | N-methylmorpholine |
| NMR | nuclear magnetic resonance | NMP | N-methyl-2-pyrrolidone |
| NMO | N-methylmorpholine-N-oxide | o/n | overnight |
| Ph | phenyl | pH | $-\log_{10}H^+$ concentration |
| ppm | parts per million | q | quartet |
| Rt | retention time | RP-HPLC | reverse-phase high performance liquid chromatography |
| s | singlet | SFC | supercritical fluid chromatography |
| sat. | saturated | t | triplet |
| t-Bu | tert-butyl | TBAF | tert.butylammonium fluoride |
| Tf | trifluoromethanesulfonyl | TFA | trifluoroacetic acid |
| TFAA | trifluoroacetic anhydride | TBS | tert-butyldimethylsilyl |
| TEA | triethylamine | temp. | temperature |
| THF | tetrahydrofuran | TLC | thin layer chromatography |

General Synthetic Schemes

Examples of compounds of formula (I) can be prepared as described in the Schemes B, C and D below. The required intermediates F for schemes B, C and D are prepared as described below in Scheme A.

As shown in Scheme A, pyridine A is chlorinated and formylated in a one-pot reaction with $POCl_3$ in a suitable solvent such as DMF at a suitable temperature, generally from 0° C. to 90° C. (e.g., room temperature), to yield the aromatic aldehyde B. The aldehyde B can be reacted with a deprotonated alkyne (e.g a Grignard reagent), wherein $R^3$ is as defined herein, in a suitable solvent such as THF, at a suitable temperature (e.g., −70° C.) to furnish the benzyl alcohol C. The benzyl alcohol C, wherein $R^3$ is as defined herein, is oxidized to the corresponding ketone under appropriate oxidizing conditions such as the Dess-Martin periodinane reagent in a suitable solvent such as DCM at a suitable temperature, generally from 0° C. to room temperature. Reaction of aniline AX, wherein X is F, Br or I, under Lewis acid-catalysis (e.g. $AlCl_3$) in a suitable solvent such as DCM at a suitable temperature, generally from 0° C. to room temperature, provides intermediates E, wherein X is F, Br or I and $R^3$ is as defined herein. The intermediates E can be cyclized to the annealated 4-pyridones F, wherein X is F, Br or I and $R^3$ is as defined herein, under basic conditions (e.g. with triethylamine in DMF for intermediates E, wherein X is F or I and $R^3$ is as defined herein, or with NaOH in DCM for intermediates E, wherein X is Br and $R^3$ is as defined herein) at a suitable temperature, generally from room temperature to 60° C.

Scheme A

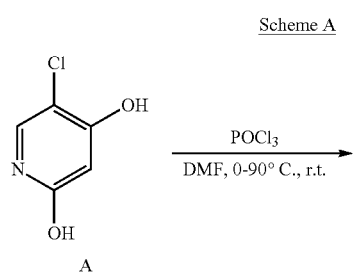

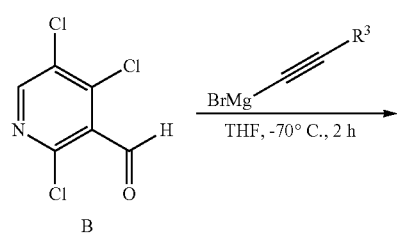

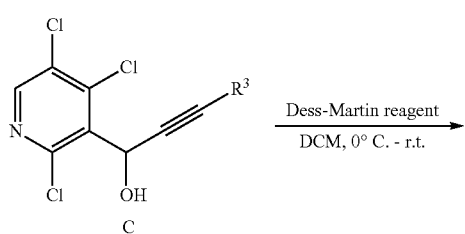

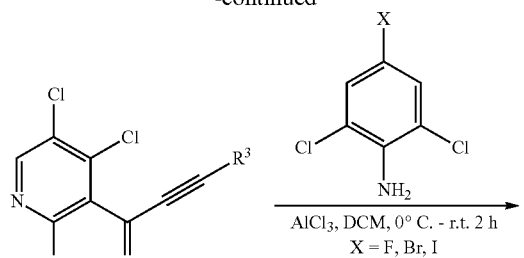

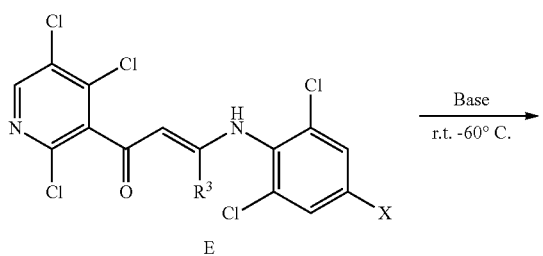

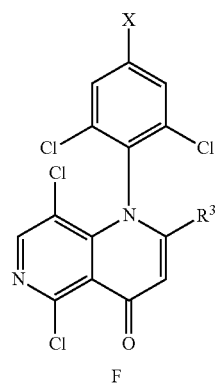

Examples of compounds of the general formula (Ia) can be prepared as described below in Scheme B.

Scheme B

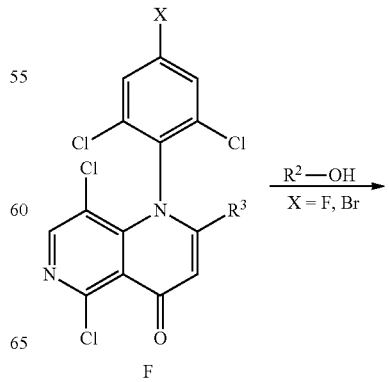

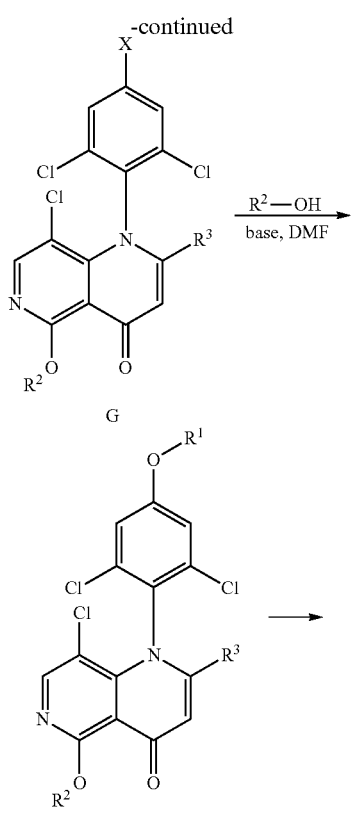

As shown in Scheme B, intermediates F, wherein X is F or Br and $R^3$ is as defined herein, can be converted to intermediates G by nucleophilic aromatic substitution with $R^2$—OH, wherein $R^2$ is as defined herein. The substituent —$OR^1$ can be introduced by a second nucleophilic aromatic substitution with $R^1$—OH, wherein $R^1$ is as defined herein, using intermediates G, wherein X is F or Br and $R^2$ and $R^3$ are as defined herein, yielding compounds of formula (Ia), wherein $R^1$, $R^2$ and R are as defined herein. The required $R^1$—OH and $R^2$—OH alcohols are either commercially available or can be prepared according to literature or in an analogous manner. Additional transformations can be performed, e.g. protecting group manipulations or amide formation anywhere in the synthetic sequence, to yield further compounds of the general formula (Ia), wherein $R^1$ and $R^3$ are as defined herein, and $R'^2$ is ($C_1$-$C_6$)alkyl substituted with one or more substituents independently selected from —NHC(O)$R^d$ and —C(O)NHR$^e$, wherein the ($C_1$-$C_6$)alkyl is further optionally substituted with one or more substituents independently selected from halo, —OH and —CN, and wherein $R^2$ is different from $R'^2$.

Alternatively, as shown in Scheme C, intermediates G, wherein X is Br or I and $R^2$ and $R^3$ are as defined herein, can be converted to boronate esters H in the presence of a suitable catalyst such as PdCl$_2$(dppf). The boronate ester H can be oxidized to phenol J, wherein $R^2$ and $R^3$ are as defined herein, with hydrogen peroxide in the presence of a suitable catalyst. Intermediates J can be converted via nucleophilic substitution with bromides or triflates in the presence of a suitable base to yield compounds of the general formula (Ia), wherein $R^1$, $R^2$ and R are as defined herein. As shown in Scheme B, additional transformations can be performed e.g. protecting group manipulations or amide formation anywhere in the synthetic sequence to yield further compounds of the general formula (Ia), wherein $R^1$ and R are as defined herein, and $R'^2$ is ($C_1$-$C_6$)alkyl substituted with one or more substituents independently selected from —NHC(O)$R^d$ and —C(O)NHR$^e$, wherein the ($C_1$-$C_6$)alkyl is further optionally substituted with one or more substituents independently selected from halo, —OH and —CN, and wherein $R^2$ is different from $R'^2$.

Scheme C

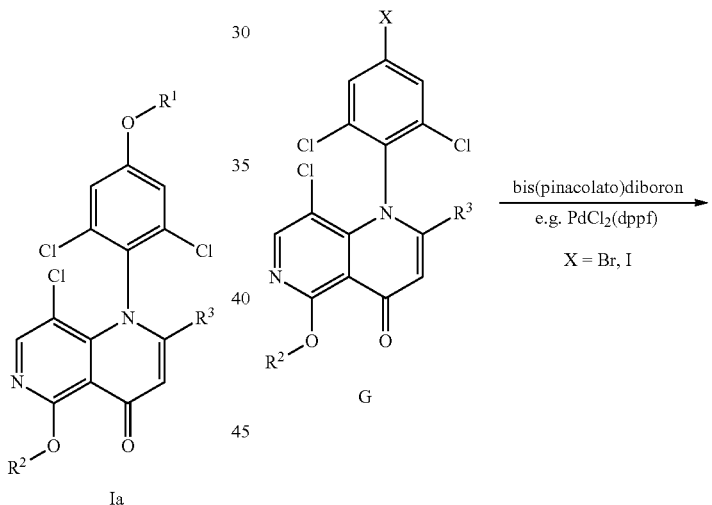

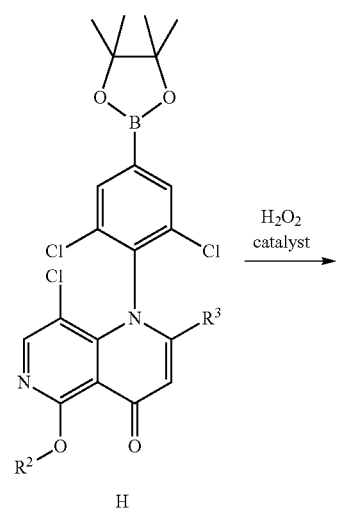

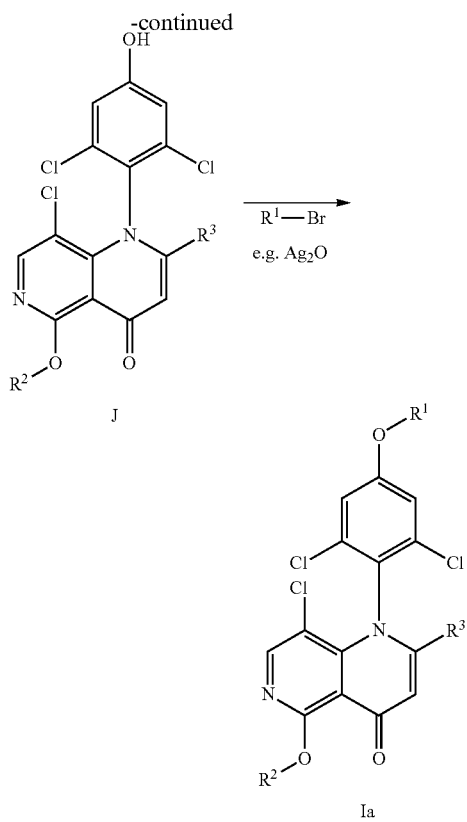

According to Scheme D, intermediates F, wherein X is F, can be also reacted via a Stille coupling with stannanes (e.g., vinyl- or allyl-tributyl stannane) in the presence of a suitable Pd catalyst such as $Pd_2(dba)_3$ with a suitable base such as trifurylphosphine to yield compounds K, wherein $R_A$ is vinyl or allyl and $R^3$ is as defined herein. Nucleophilic aromatic substitution with $R^1$—OH, wherein $R^1$ is as defined herein, leads to intermediates L which can be subjected to addition of sodium alkyl sulfonates $R_A'SO_2Na$, wherein $R_A'$ is ($C_1$-$C_6$)alkyl substituted with —$SO_2(C_1$-$C_4)$alkyl, in a suitable solvent such as EtOH or AcOH to provide compounds of the general formula (Ib), wherein $R_A'$ is ($C_1$-$C_6$)alkyl substituted with —$SO_2(C_1$-$C_4)$alkyl and $R^1$ and $R^3$ are as defined herein. Alternatively, alkenes can be employed to form in situ terminal boranes with 9-BBN which undergo Pd-catalyzed coupling in the presence of a suitable Pd catalyst such as $Pd(PPh_3)_4$ with intermediates F, wherein X is F, to form intermediates M, wherein $R_B$ is ($C_1$-$C_6$)alkyl substituted with —$S(C_1$-$C_4)$alkyl or —$C(O)NHR^c$, and $R^3$ and R are as defined herein. In the case of sulfides side chains, oxidation (e.g., with $H_2O_2$) provides sulfones in a subsequent step. Additional nucleophilic aromatic substitution with $R^1$—OH, wherein $R^1$ is as defined herein, provides compounds of the general formula (Ic), wherein $R_B'$ is ($C_1$-$C_6$)alkyl substituted with —$SO_2(C_1$-$C_4)$alkyl or —$C(O)NHR^c$, and $R^1$, $R^3$ and R are as defined herein.

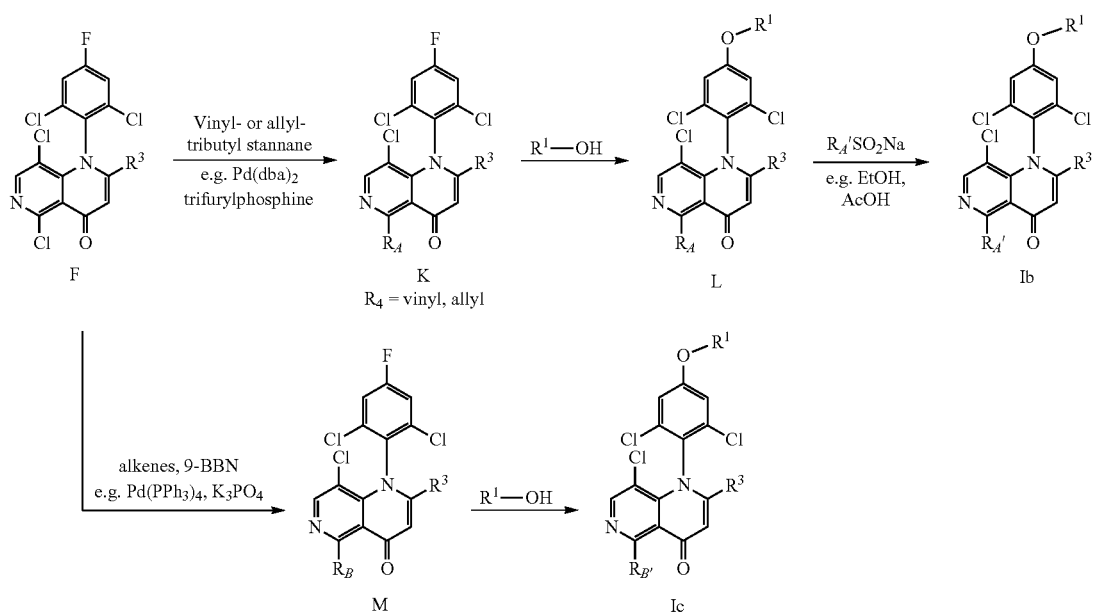

Scheme D

The following LC-MS methods were used for characterization of the examples and intermediates:

LCMS Method 1
　System: Shimadzu LCMS 2020
　Column: Synergi 2.5 µMAX-RP100 A Mercury
　Column temperature: 40° C.
　Gradient (Time/% B): 0.1/5, 0.5/5, 1.0/95, 1.5/95, 2.0/5, 3.0/5
　Eluent A: 0.10% HCO$_2$H in water
　Eluent B: CH$_3$CN
　Flow: 2.0 mL/min
　Ion Source: DUIS-ESI & APCI
　Nebulizing Gas Flow: 1.5 L/min
　DL Temperature: 250° C.
　Heat Block Temperature: 400° C.

LCMS Method 2
　System: Shimadzu LCMS 2020
　Column: Kinetex 2.6 µm, C18 100 A, 30×3 mm.
　Column temperature: 40° C.
　Gradient (Time/% B): 0.1/20, 0.25/20, 0.75/95, 1.75/95, 2/20, 2.5/20
　Eluent A: 0.10% HCO$_2$H in water
　Eluent B: CH$_3$CN
　Flow: 1.0 mL/min
　Ion Source: DUIS-ESI & APCI
　Nebulizing Gas Flow: 1.5 L/min
　DL Temperature: 250° C.
　Heat Block Temperature: 400° C.

LCMS Method 3
　System: Shimadzu LCMS 2020
　Column: Synergi 2.5µ MAX-RP100 A Mercury
　Column temperature: 40° C.
　Gradient (Time/% B): 0.1/5, 0.5/5, 1.0/95, 1.5/95, 2.0/5, 3.0/5
　Eluent A: 0.10% HCO$_2$H in water
　Eluent B: CH$_3$CN
　Flow: 1.0 mL/min
　Ion Source: DUIS-ESI & APCI
　Nebulizing Gas Flow: 1.5 L/min
　DL Temperature: 250° C.
　Heat Block Temperature: 400° C.

LCMS Method 4
　System: SCI EX API 3200
　Column: Kinetex EVO C18 100 A, 2.6 µm, 50×4.6 mm,
　Column temperature: 30° C.
　Gradient: (Time/% B): 0/30, 0.2/30, 0.7/95, 2.0/95, 2.5/30, 3.5/30
　Eluent A: 0.10% HCO$_2$H in water
　Eluent B: 0.1% HCO$_2$H in CH$_3$CN
　Flow: 1.5 mL/min
　Ion Source: Turbo Spray
　Heat Block Temperature: 450° C.

LCMS Method 5
　System: SCI EX API 2000
　Column: Synergi 2.5µ MAX-RP100 A Mercury
　Column temperature: 30° C.
　Gradient: (Time/% B): 0/30, 0.5/30, 1.0/95, 1.5/95, 2.5/30, 3.0/30
　Eluent A: 0.10% HCO$_2$H in water
　Eluent B: 0.1% HCO$_2$H in CH$_3$CN
　Flow: 2 mL/min
　Ion Source: Turbo Spray
　Heat Block Temperature: 450° C.

LCMS Method 6
　System: Shimadzu LCMS 2020
　Column: Synergi 2.5µ MAX-RP100 A Mercury
　Column temperature: 40° C.
　Gradient (Time/% B): 0.1/5, 0.5/5, 1.0/95, 1.5/95, 2.0/5, 3.0/5
　Eluent A: 0.10% HCO$_2$H in water
　Eluent B: CH$_3$CN
　Flow: 2.0 mL/min
　Ion Source: DUIS-ESI & APCI
　Nebulizing Gas Flow: 1.5 L/min
　DL Temperature: 250° C.
　Heat Block Temperature: 400° C.

LCMS Method 7
　System: Agilent 1100
　Column: Acquity UPLC BEH C18 Column, 2.1×30 mm, 1.7 µm column
　Oven temperature: 50° C.
　Gradient: (Time/% B): 0min/2 for 0.1 min, 0.1 min/2 to 1.5 min/98, 1.8 min/98, 1.8 min/98 to 1.9 min/2, 2.0 min/2
　Eluent A: 0.10% formic acid in water
　Eluent B: 0.1% formic acid in CH$_3$CN
　Flow: 1 mL/min Chiral HPLC Method 1
　Column: Chiral PAL-IH (150×4.6 mm×5 µM)
　Mobile Phase: A; n-Hexane, B: 0.1% HCOOH in ethanol:methanol (80:20)
　Isocratic: 70:30 (A:B)
　Flow: 1 mL/min
　Diluent: Ethanol
　Column Temp. 25° C.

Chiral HPLC Method 2
　Column: Lux Cellulose (150×4.6 mm×5 µM)
　Mobile Phase: A; n-Hexane, B: 0.1% HCOOH in ethanol:methanol (80:20)
　Isocratic: 70:30 (A:B)
　Flow: 1 mL/min
　Diluent: Ethanol
　Column Temp. 25° C.

Synthesis of Intermediates F (F1, F2 and F3)

Synthesis of 5,8-dichloro-1-(2,6-dichloro-4-fluorophenyl)-2-methyl-1,6-naphthyridin-4(1H)-one (Intermediate F1)

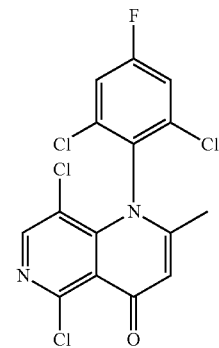 [SMILES: Cc1cc(=O)c2c(Cl)ncc(Cl)c2n1-c1c(Cl)cc(F)cc1Cl]

Step 1: 2,4,5-Trichloronicotinaldehyde

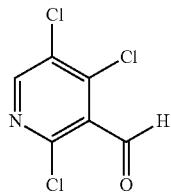 [SMILES: O=Cc1c(Cl)ncc(Cl)c1Cl]

Under nitrogen, phosphoryl trichloride (475 mL) was added dropwise to DMF (750 mL) at 0° C. The resulting mixture was stirred for 1 h at 0° C. Then 5-chloropyridine-2,4-diol (150 g, 1.03 mol) was added. The mixture was stirred for 12 h at 90° C. LCMS showed reaction was completed. The reaction mixture was cooled to 0° C., was poured into 2000 mL of ice water and extracted with 3×1000 mL of DCM. The organic layers were combined, washed with brine, dried over anhydrous sodium sulfate and concentrated. The residue was applied onto a silica gel column with ethyl acetate/petroleum ether (1:9). This resulted in 131 g (48%) of 2,4,5-trichloronicotinaldehyde as a yellow solid. ESI-MS m/z: 210.0 [M+H]$^+$; $^1$H NMR (400 MHz, DCM-d$_2$) δ ppm=10.43 (s, 1H), 8.61 (s, 1H).

Step 2: 1-(2,4,5-Trichloropyridin-3-yl)but-2-yn-1-ol

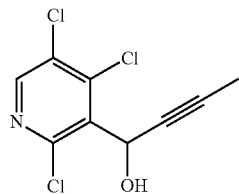

To a solution of 2,4,5-trichloronicotinaldehyde (117 g, 0.56 mol) in THF (1000 mL) was added dropwise prop-1-yn-1-yl magnesium bromide (1.2 L, 0.62 mol) at −60° C. and stirring continued for 1 h at −60° C. LCMS showed reaction was completed. The reaction mixture was quenched with ammonium chloride solution (1000 mL) under −20° C. The resulting solution was extracted with ethyl acetate. The mixture was washed with H$_2$O and brine, dried over anhydrous sodium sulfate and concentrated. This resulted in 120 g (86%) of 1-(2,4,5-trichloropyridin-3-yl)but-2-yn-1-ol as a yellow solid. ESI-MS m/z: 250.0 [M+H]$^+$; $^1$H NMR (400 MHz, DCM-d$_2$) δ ppm=8.42 (s, 1H), 6.13 (s, 1H), 3.11 (bs, 1H), 1.90 (s, 3H).

Step 3: 1-(2,4,5-Trichloropyridin-3-yl)but-2-yn-1-one

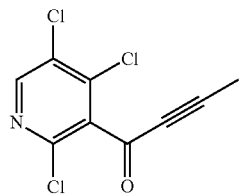

To a solution of 1-(2,4,5-trichloropyridin-3-yl)but-2-yn-1-ol (150 g, 0.60 mol) in DCM 1000 mL) was added Dess-Martin reagent (280 g, 0.66 mol) at 0° C. The mixture was stirred for 2 h at room temperature. LCMS showed reaction was completed. Solids were filtered out. The filtrate solution was washed with sodium sulfite solution and sodium carbonate solution. The organic layer was dried over anhydrous sodium sulfate and concentrated under vacuum. This resulted in 1-(2,4,5-trichloropyridin-3-yl)but-2-yn-1-one (160 g crude) as a brown solid. ESI-MS m/z: 248.0 [M+H]$^+$; $^1$H NMR (400 MHz, DCM-d$_2$) δ ppm=8.51 (s, 1H), 2.16 (s, 3H).

Step 4: (E)-3-((2,6-Dichloro-4-fluorophenyl)amino)-1-(2,4,5-trichloropyridin-3-yl)but-2-en-1-one

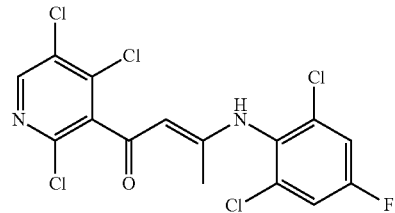 [SMILES: C/C(=C\C(=O)c1c(Cl)ncc(Cl)c1Cl)Nc1c(Cl)cc(F)cc1Cl]

To a solution of 1-(2,4,5-trichloropyridin-3-yl)but-2-yn-1-one (160 g, 0.64 mol), 4-fluoro-2,6-dichloroaniline (115 g, 0.64 mol) in DCM (1200 mL) was added AlCl$_3$ (102 g, 0.76 mol) at 5° C. Stirring was continued for 2 h at room temperature. LCMS showed reaction was completed. The solution was quenched with water at 5° C. The resulting solution was extracted with ethyl acetate (2×1000 mL) and the organic layers were combined. The organic layer was dried over anhydrous sodium sulfate and concentrated. This resulted in 340 g (crude) (E)-3-((2,6-dichloro-4-fluorophenyl)amino)-1-(2,4,5-trichloropyridin-3-yl)but-2-en-1-one as a brown solid. The crude material was used directly in the next step. ESI-MS m/z: 427 [M+H]$^+$.

Step 5: 5,8-Dichloro-1-(2,6-dichloro-4-fluorophenyl)-2-methyl-1,6-naphthyridin-4(1H)-one

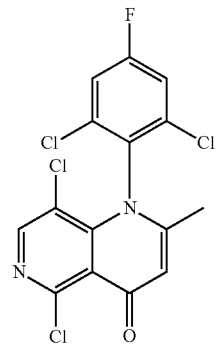 [SMILES: Cc1cc(=O)c2c(Cl)ncc(Cl)c2n1-c1c(Cl)cc(F)cc1Cl]

To a solution of (E)-3-((2,6-dichloro-4-fluorophenyl)amino)-1-(2,4,5-trichloropyridin-3-yl)but-2-en-1-one (340 g crude) in DMF (1000 mL) was added TEA (252 g, 2.5 mol) at room temperature. The mixture was stirred for 1 h at 60° C. LCMS showed reaction was completed. The solution was quenched with 2 L water and extracted with ethyl acetate (3×1000 mL). The combined organic layers were washed with water and brine, dried over anhydrous sodium sulfate and concentrated. The residue was applied onto a silica gel column with ethyl acetate/petroleum ether (3:7) as eluent. This resulted in 162.6 g (64% over two steps) 5,8-dichloro-1-(2,6-dichloro-4-fluorophenyl)-2-methyl-1,6-naphthyridin-4(1H)-one as a light brown solid. ESI-MS m/z: 391.0 [M+H]$^+$; $^1$H NMR (300 MHz, CHLOROFORM-d$_3$) δ ppm=8.31 (s, 1H), 7.26 (d, J=12.3 Hz, 2H), 6.47 (s, 1H), 1.99 (m, 3H).

Synthesis of 1-(4-bromo-2,6-dichlorophenyl)-5,8-dichloro-2-methyl-1,6-naphthyridin-4(1H)-one (intermediate F2)

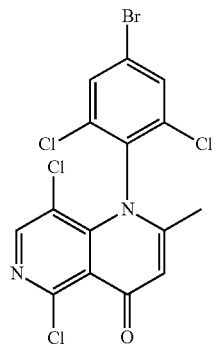 [SMILES: Cc1cc(=O)c2c(Cl)ncc(Cl)c2n1-c1c(Cl)cc(Br)cc1Cl]

Steps 1 to 3: See synthesis of intermediate F1

Step 4: (E)-3-((4-Bromo-2,6-dichlorophenyl)amino)-1-(2,4,5-trichloropyridin-3-yl)but-2-en-1-one

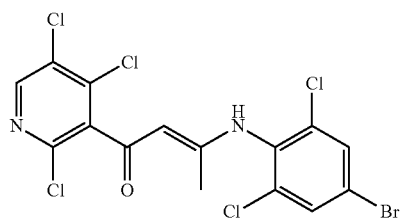 [SMILES: C/C(=C\C(=O)c1c(Cl)ncc(Cl)c1Cl)Nc1c(Cl)cc(Br)cc1Cl]

To a solution of 1-(2,4,5-trichloropyridin-3-yl)but-2-yn-1-one (120 g, 0.49 mol), 4-bromo-2,6-dichloroaniline (118 g, 0.49 mol) in DCM (800 mL) was added AlCl$_3$ (78 g, 0.58 mol) at 5° C. Stirring was continued for 2 h at room temperature. LCMS showed reaction was completed. The solution was quenched with water at 5° C. The resulting solution was extracted with ethyl acetate (2×1000 mL) and the organic layers were combined. The organic layer was dried over anhydrous sodium sulfate and concentrated. This resulted in 240 g (crude) (E)-3-((4-bromo-2,6-dichlorophenyl)amino)-1-(2,4,5-trichloropyridin-3-yl)but-2-en-1-one as a brown solid. The crude was used directly in the next step. ESI-MS m/z: 487 [M+H]$^+$.

Step 5: 1-(4-Bromo-2,6-dichlorophenyl)-5,8-dichloro-2-methyl-1,6-naphthyridin-4(1H)-one

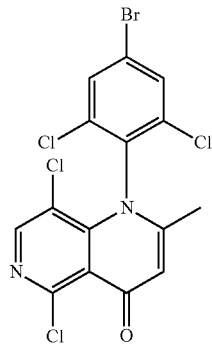 [SMILES: Cc1cc(=O)c2c(Cl)ncc(Cl)c2n1-c1c(Cl)cc(Br)cc1Cl]

To a solution of (E)-3-((4-bromo-2,6-dichlorophenyl)amino)-1-(2,4,5-trichloropyridin-3-yl)but-2-en-1-one (240 g crude) in DCM (270 mL) was added NaOH (2.83 g, 1.2 equiv). The reaction mixture was stirred at 15~25° C. for 8~12 hours. After reaction completed, the mixture was concentrated to 50-60 g. Toluene (143 mL) was charged. The mixture was concentrated to 50~60 g. Toluene (289 mL) was charged. The organic layer was washed with water (3×289 mL). The aqueous layer was combined and extracted with toluene (289 mL). The combined toluene layer was stirred with activated carbon (1.45 g, 50~60° C., 2~3 hours), filtered and concentrated. After crystallization in toluene/heptane (v/v=1/1), 1-(4-bromo-2,6-dichlorophenyl)-5,8-dichloro-2-methyl-1,6-naphthyridin-4(1H)-one was obtained as a light brown solid in 69% yield. ESI-MS m/z: 452 [M+H]$^+$; $^1$H NMR (300 MHz, CHLOROFORM-d$_3$) δ ppm=8.33 (s, 1H), 7.67 (s, 2H), 6.49 (d, J=0.6 Hz, 1H), 1.99 (m, 3H).

Synthesis of 5,8-dichloro-1-(2,6-dichloro-4-iodophenyl)-2-methyl-1,6-naphthyridin-4(1H)-one (intermediate F3)

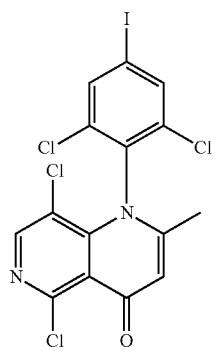 [SMILES: Cc1cc(=O)c2c(Cl)ncc(Cl)c2n1-c1c(Cl)cc(I)cc1Cl]

Intermediate F3 was prepared in an analogous manner to intermediates F1 and F2 but using 2,6-dichloro-4-iodoaniline. ESI-MS m/z: 498.8 [M+H]$^+$; $^1$H NMR (300 MHz, DMSO-d6) δ ppm=8.52 (s, 1H), 8.22 (s, 2H), 6.61 (s, 1H), 1.94 (s, 3H).

Synthesis of Compounds of Formula (I)

The following examples of compounds of either formula (Ia) or formula (Ib) or formula (Ic) have been prepared from intermediates F1 and F2 as described below.

Example 1: 3-((8-Chloro-1-(2,6-dichloro-4-(2-hydroxyethoxy)phenyl)-2-methyl-4-oxo-1,4-dihydro-1,6-naphthyridin-5-yl)oxy)-N-methylpropanamide (Compound C-1)

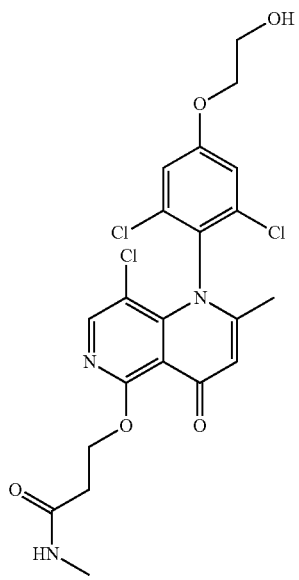 [SMILES: CNC(=O)CCOc1ncc(Cl)c2c1c(=O)cc(C)n2-c1c(Cl)cc(OCCO)cc1Cl]

Step 1: 3-((8-Chloro-1-(2,6-dichloro-4-fluorophenyl)-2-methyl-4-oxo-1,4-dihydro-1,6-naphthyridin-5-yl)oxy)-N-methylpropanamide To 5,8-dichloro-1-(2,6-dichloro-4-fluorophenyl)-2-methyl-1,6-naphthyridin-4(1H)-one (intermediate F1, 3.5 g, 8.927 mmol) and 3-hydroxy-N-methylpropanamide (1.38 g, 13.39 mmol) in acetonitrile (40 mL) was added potassium carbonate (3.08 g, 22.31 mmol), DMAP (327.1 mg, 2.678 mmol) and the mixture was heated at 80° C. for 16 h. Progress of the reaction was monitored by TLC until complete consumption of starting material. The color of the reaction mixture changed from pale brown to dark brown. The mixture was quenched with cold water and extracted with ethyl acetate (3×25 mL), dried and concentrated. The crude material was purified by flash chromatography using 1% MeOH in dichloromethane as eluent to get the desired product as an off-white solid (2.8 g, 69%).

Step 2: 3-((8-Chloro-1-(2,6-dichloro-4-(2-hydroxyethoxy)phenyl)-2-methyl-4-oxo-1,4-dihydro-1,6-naphthyridin-5-yl)oxy)-N-methylpropanamide To 3-((8-chloro-1-(2,6-dichloro-4-fluorophenyl)-2-methyl-4-oxo-1,4-dihydro-1,6-naphthyridin-5-yl)oxy)-N-methylpropanamide (2.8 g; 6.126 mmol) and anhydrous ethylene glycol (1.521 g; 24.506 mmol) in DMF (30 mL) was added caesium carbonate (4.99 g, 15.315 mmol) and the mixture was stirred at room temperature for 4 h. Progress of the reaction was monitored by TLC. The color of the reaction mixture changed from a pale brown color to a dark brown color. The reaction mixture was quenched with ice cold water and extracted with ethyl acetate (3×25 mL). The organic layers were dried and concentrated to give crude product. The crude material was purified by flash chromatography using 3% MeOH in dichloromethane as an eluent to get the desired product as an off-white solid (1.4 g, 46%) and additional 20% of starting material was recovered. A second chromatographic step with the same eluent was required to get 99% pure material as a white powder. C-1: HRMS m/z: calc. 500.05413 [M+H]$^+$, found 500.05482. $^1$H NMR (600 MHz, DMSO-d6) δ ppm=8.24 (s, 1H), 8.23 (q, 1H), 7.36 (s, 2H), 6.48 (s, 1H), 4.96 (s, 1H), 4.53 (t, 2H), 4.15 (t, 2H), 3.72 (t, 2H), 2.78 (s, 3H), 2.62 (d, 3H), 2.60 (t, 2H), 1.91 (m, 3H). $^{13}$C NMR (150 MHz, DMSO-d6) δ ppm=175.0, 170.1161.8, 150.9, 149.8, 145.0, 135.8, 126.8, 117.0, 115.0110.4, 109.8, 71.1, 63.3, 59.2, 35.2, 25.6, 20.0.

Crystalline forms of the compound C-1 have been isolated as shown in Modifications A-1, A-2, A-3, A-4, A-5, A-6, A-7, A-8, A-9, A-10, A-11, A-12 and A-13 as set forth below. The crystalline forms have been characterized by X-Ray Powder Diffraction (XRPD), Differential Scanning Calorimetry (DSC), Thermogravimetric Analysis (TGA), Ultra Performance Liquid Chromatography (UPLC) and NMR using the analytical methods as shown in Table 2 below.

The XRPD profiles for the respective crystalline forms are shown in the Figures. Lists of characteristic XRPD peaks are given herein in the tables below and described in the Figures. The peaks listed herein are given in degrees two theta (+0.1 degree). As will be appreciated by the skilled person, the relative intensities of the various peaks within the tables given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined in given tables. The skilled person will also appreciate that measurements using a different wavelength will result in different shifts according to the Bragg equation—$n\lambda=2d \sin \theta$. Such alternative XRPD patterns generated by use of alternative wavelengths are nevertheless representations of the same material.

TABLE 2

| Analytical methods | |
|---|---|
| Analytical method | Details |
| TGA method | |
| Instrument | TA Discovery |
| Temperature range | Room temperature to 300° C. |
| Scan rate | 10 K/min |
| Nitrogen flow | 20 mL/min |
| Sample mass | Approximately 2-10 mg |

TABLE 2-continued

Analytical methods

DSC method

| | |
|---|---|
| Instrument | TA Discovery |
| Temperature range | 0° C. to 250° C. or 300° C. |
| Scan rate | 10 K/min |
| Nitrogen flow | 50 mL/min |
| Sample mass | Approximately 2 mg |

XRPD method 1 & 2

| | |
|---|---|
| Instrument | Bruker D8 Advance |
| Detector | LynxEye (1D mode), open angle: 2.948° |
| Radiation | $CuK_\alpha$ (wavelength = 0.15418 nm) |
| Monochromator | Ni-filter |
| X-ray generator power | 40 kV, 40 mA |
| Step size | 0.0164° or 0.0410° (2theta) |
| Time per step | 0.3 s |
| Scan range | 2°-40° 2theta |
| Scan time | 768 s or 279 s |
| Slits | Primary fixed illuminated sample size: 10 mm, secondary: open angle: 2.2°, axial soller: 2.5° |

NMR

| | |
|---|---|
| Instrument | Bruker ASCEND 400 MHZ |
| Probe | 5 mm PABBO BB-1H/D Z-GRD Z108618/0226 |
| Temperature | 295.7K |
| Relaxation delay | 1 second |

UPLC Method

| | |
|---|---|
| Instrument | Waters Acquity UPLC |
| Column | ACQUITY BEH C18 |
| Particle size (μm) | 1.7 |
| Dimensions (mm) | 2.1 × 100 |
| Temperature (° C.) | 45 |
| Flow rate (mL/min) | 0.5 |
| Injection volume (μl) | 1 |
| Sample solvent | Acetonitrile/water (80:20) |
| Sample concentration (μg/mL) | 100 |
| Detection wavelength (nm) | 210 |
| Mobile Phase A | 95% 10 mM Ammonium acetate buffer/5% ACN |
| Mobile Phase B | 95% Acetonitrile/5% Water |
| Run time (min) | 14 |

| | Minutes | % B |
|---|---|---|
| Gradient | 0 | Initial |
| | 0 | 2.0 |
| | 50 | 8.0 |
| | 95 | 11.0 |
| | 95 | 12.0 |
| | 0 | 12.1 |
| | 0 | 14.0 |

Modification A-1: Free crystalline form of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1)

Compound C-1 of Example 1 (2.0 g) was dissolved into a water/ethanol solution at a temperature below 35° C. The resulting solution was filtered to remove undissolved impurities. After adding a first portion of water into the reactor at a temperature of 25° C. under stirring, a seed was obtained. A second portion of water was added, and the solid so obtained was filtered, washed and dried at 50° C. under vacuum at 0-100 mbar. The solid residue (1.77 g) was recovered with a purity of 99.52% (UPLC) and analyzed by XRPD, DSC, TGA and NMR. The physicochemical properties are represented in Table 3.

TABLE 3

Physicochemical properties of Modifications A-1, A-2, A-3, A-4 and A-5

| Parameter | A-1 | A-2 | A-3 | A-4 | A-5 |
|---|---|---|---|---|---|
| $T_{onset}$ melting point (DSC, ° C.) | 159.0 | 157.5 | 156.6 | 121.5 157.4 | 110.8 157.4 |
| LOD (TGA, % at ° C.) | 0.17% (120° C.) | 3.4% (80° C.) | 3.0% (70° C.) | 3.6% (110° C.) | 1.4% (110° C.) |
| Water content (Karl Fischer, % m/m) | 0.4 | 4.0 | 3.6 | 4.1 | 2.0 |

The DSC thermogram of Modification A-1 of Example 1 is shown in FIGURE A1-2. The TGA of Modification A-1 of Example 1 is shown in FIGURE A1-3. DSC data showing the melting transitions of Modification A-1 and the total water loss (Loss on Drying—LOD) as measured by TGA are represented in Table 3.

The XRPD pattern of Modification A-1 of Example 1 is shown in FIGURE A1-1. The XRPD peaks, when measured using a CuKα radiation with a wavelength of 1.5418 Å at a temperature of about 22° C., are as set forth in the following table:

| No. | Angle 2θ | d value Å | Relative Intensity % |
|---|---|---|---|
| 1 | 7.7 | 11.47 | 99 |
| 2 | 11.3 | 7.86 | 5 |
| 3 | 15.4 | 5.74 | 10 |
| 4 | 16.4 | 5.40 | 32 |
| 5 | 17.7 | 5.00 | 9 |
| 6 | 21.2 | 4.19 | 19 |
| 7 | 22.7 | 3.91 | 9 |
| 8 | 23.3 | 3.81 | 43 |
| 9 | 24.0 | 3.70 | 100 |
| 10 | 26.4 | 3.37 | 12 |
| 11 | 27.2 | 3.28 | 23 |

Modification A-2: Hydrate crystalline form of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1)

Compound C-1 of Example 1 (2.0 g) was dissolved into a water/ethanol solution at a temperature below 35° C. The resulting solution was filtered to remove undissolved impurities. After adding a first portion of water into the reactor at a temperature of 25° C. under stirring, a seed was obtained. A second portion of water was added to the suspension dropwise at a temperature of 16° C. over 10 h, and the resulting suspension was hold at 16° C. for 13 h. The solid so obtained was then filtered, washed and dried at 45° C. under vacuum at 40 mbar. The solid residue (1.94 g) was recovered with a purity of 99.59% (UPLC) and analyzed by XRPD, DSC, TGA and NMR. The physicochemical properties are represented in Table 3.

The DSC thermogram of Modification A-2 of Example 1 is shown in FIG. A2-2. The TGA of Modification A-2 of Example 1 is shown in FIG. A2-3. DSC data showing the melting transitions of Modification A-2 and the total water loss (Loss on Drying—LOD) as measured by TGA are represented in Table 3.

The XRPD pattern of Modification A-2 of Example 1 is shown in FIG. A2-1. The XRPD peaks, when measured using a CuKα radiation with a wavelength of 1.5418 Å at a temperature of about 22° C., are as set forth in the following table:

| No. | Angle 2θ | d value Å | Relative Intensity % |
|---|---|---|---|
| 1 | 7.6 | 11.62 | 17 |
| 2 | 10.7 | 8.30 | 3 |
| 3 | 15.2 | 5.81 | 4 |
| 4 | 16.9 | 5.24 | 27 |
| 5 | 21.4 | 4.15 | 17 |
| 6 | 24.0 | 3.70 | 100 |
| 7 | 25.8 | 3.45 | 3 |
| 8 | 27.4 | 3.26 | 17 |
| 9 | 30.7 | 2.91 | 2 |

Modification A-3: Hydrate crystalline form of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1)

Compound C-1 of Example 1 was transferred into a 75% relative humidity chamber and hold for about 24 hours to get a solid residue (5.1 g). It was recovered with a purity of 99.09% (UPLC) and analyzed by XRPD, DSC, TGA and NMR. The physicochemical properties are represented in Table 3.

The DSC thermogram of Modification A-3 of Example 1 is shown in FIG. A3-2. The TGA of Modification A-3 of Example 1 is shown in FIG. A3-3. DSC data showing the melting transitions of Modification A-3 and the total water loss (Loss on Drying—LOD) as measured by TGA are represented in Table 3.

The XRPD pattern of Modification A-3 of Example 1 is shown in FIG. A3-1. The XRPD peaks, when measured using a CuKα radiation with a wavelength of 1.5418 Å at a temperature of about 22° C., are as set forth in the following table:

| No. | Angle 2θ | d value Å | Relative Intensity % |
|---|---|---|---|
| 1 | 7.6 | 11.55 | 23 |
| 2 | 15.3 | 5.78 | 9 |
| 3 | 17.0 | 5.22 | 18 |
| 4 | 20.7 | 4.29 | 5 |
| 5 | 21.4 | 4.14 | 8 |
| 6 | 22.2 | 3.99 | 33 |
| 7 | 25.9 | 3.44 | 20 |
| 8 | 29.1 | 3.07 | 10 |
| 9 | 32.3 | 2.77 | 12 |

Modification A-4: Hydrate crystalline form of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1)

Compound C-1 of Example 1 (10.0 g) was suspended into 60 mL of methanol/water mixture at a temperature of 40° C. The resulting suspension was stirred at 60° C. to obtain a clear solution. The solution was cooled to 50° C. and stirred for 1 hour. The solution was then cooled to 40° C. for 10 hours. The solid so obtained was filtered, washed and dried under vacuum at room temperature. The solid residue was recovered with a purity of 99.57% (UPLC) and analyzed by XRPD, DSC, TGA and NMR. The physicochemical properties are represented in Table 3.

The DSC thermogram of Modification A-4 of Example 1 is shown in FIG. A4-2. The TGA of Modification A-4 of Example 1 is shown in FIG. A4-3. DSC data showing the melting transitions of Modification A-4 and the total water loss (Loss on Drying—LOD) by TGA are represented in Table 3.

The XRPD pattern of Modification A-4 of Example 1 is shown in FIG. A4-1. The XRPD peaks, when measured using a CuKα radiation with a wavelength of 1.5418 Å at a temperature of about 22° C., are as set forth in the following table:

| No. | Angle 2θ | d value Å | Relative Intensity % |
|---|---|---|---|
| 1 | 7.3 | 12.11 | 29 |
| 2 | 10.3 | 8.59 | 3 |
| 3 | 15.5 | 5.73 | 10 |
| 4 | 22.1 | 4.02 | 3 |
| 5 | 23.1 | 3.84 | 100 |
| 6 | 23.9 | 3.73 | 19 |
| 7 | 25.5 | 3.49 | 7 |
| 8 | 25.9 | 3.44 | 6 |
| 9 | 26.4 | 3.37 | 50 |
| 10 | 31.2 | 2.86 | 8 |

Modification A-5: Hydrate crystalline form of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1)

The hydrate crystalline form of Modification A-4 of Example 1 was kept at 80° C. under 11% relative humidity for 1 week. The solid residue was analyzed by XRPD, DSC, TGA and NMR. The physicochemical properties are represented in Table 3.

The DSC thermogram of Modification A-5 of Example 1 is shown in FIG. A5-2. The TGA of Modification A-5 of Example 1 is shown in FIG. A5-3. DSC data showing the melting transitions of Modification A-5 and the total water loss (Loss on Drying—LOD) by TGA are represented in Table 3.

The XRPD pattern of Modification A-5 of Example 1 is shown in FIG. A5-1. The XRPD peaks, when measured using a CuKα radiation with a wavelength of 1.5418 Å at a temperature of about 22° C., are as set forth in the following table:

| No. | Angle 2θ | d value Å | Relative Intensity % |
|---|---|---|---|
| 1 | 5.0 | 17.84 | 47 |
| 2 | 9.9 | 8.93 | 14 |
| 3 | 14.9 | 5.96 | 21 |
| 4 | 15.9 | 5.58 | 39 |
| 5 | 17.7 | 5.01 | 14 |
| 6 | 19.8 | 4.47 | 87 |
| 7 | 24.0 | 3.71 | 84 |
| 8 | 25.5 | 3.49 | 68 |
| 9 | 27.2 | 3.28 | 23 |

Modification A-6: Solvate of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) with cyclopentanone Compound C-1 of Example 1 was equilibrated with cyclopentanone at 4° C. for 14 days. The solid residue was recovered and analyzed by XRPD, DSC, TGA, UPLC and NMR.

Modification A-6 is a highly crystalline form with a melting point of approximately 157° C. The desolvation temperature is around 102° C. It shows 4.6% weight loss by TGA at 150° C. The XRPD pattern is shown in FIG. A6-1, when measured using a CuKα radiation with a wavelength of 1.5418 Å at a temperature of about 22° C.

Modification A-7: Solvate of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) with methanol Compound C-1 of Example 1 was equilibrated with methanol or methanol/water (97:3 v/v) at 4° C. for 14 days. The solid residue was recovered and analyzed by XRPD, DSC, TGA, UPLC and NMR.

Modification A-7 is a highly crystalline form with a melting point of approximately 157° C. The desolvation temperature is around 79° C. It shows 3.7% weight loss by TGA at 105° C. The XRPD pattern is shown in FIG. A7-1, when measured using a CuKα radiation with a wavelength of 1.5418 Å at a temperature of about 22° C.

Modification A-8: Solvate of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) with pyridine Compound C-1 of Example 1 was equilibrated with pyridine at 4° C. for 7 days. The solid residue was recovered and analyzed by XRPD, DSC, TGA, UPLC and NMR. The XRPD pattern is shown in FIG. A8-1, when measured using a CuKα radiation with a wavelength of 1.5418 Å at a temperature of about 22° C.

Co-Crystals of the Compound C-1 (Modifications A-9, A-10, A-11, A-12 and A-13)

The compound C-1 of Example 1 was mixed with the appropriate amount of co-crystal former. The resulting mixtures were dissolved/slurred in individual solvents at 50° C. and cooled to room temperature until precipitation occurred. Solutions obtained after cooling were evaporated to dryness to obtain a solid. Solid residues were recovered and analyzed by XRPD, DSC, TGA, UPLC and NMR. The physicochemical properties of the co-crystals of the compound C-1 are represented in Table 4.

TABLE 4

Physicochemical properties of Modifications A-9, A-10, A-11, A-12 and A-13

| Parameter | A-9 | A-10 | A-11 | A-12 | A-13 |
|---|---|---|---|---|---|
| Purity (UPLC, %) | 99.83 | 99.73 | 99.86 | 99.39 | 99.44 |
| C-1/co-former (NMR, molar ratio) | 1/0.76 | 1/0.97 | 1/1.01 | 1/1.02 | 1/0.50 |
| $T_{onset}$ melting point (DSC, ° C.) | 161.8 | 167.2 | 98.4 130.0 | 134.9 | 147.9 |
| LOD (TGA, % at ° C.) | 1.5% (105° C.) | 0.3% (120° C.) | 0.2% (110° C.) | <0.1% (120° C.) | 0.1% (120° C.) |
| Residual solvent (NMR) | 0.24% acetonitrile | 0.12% acetone | 0.20% isopropanol | 0.11% isopropanol | <0.1% isopropanol |

Modification A-9: Co-crystal of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) with phosphoric acid (1:0.76 molar ratio)

Compound C-1 of Example 1 (0.2 g) and 1.0 equiv. phosphoric acid were dissolved in 4.0 mL acetonitrile:$H_2O$ (95:5 v/v). The resulting mixture was dissolved at 50° C. and cooled to room temperature to yield a 1:0.76 molar ratio co-crystal of compound C-1 with phosphoric acid.

The DSC thermogram of Modification A-9 of Example 1 is shown in FIG. A9-2. The TGA of Modification A-9 of Example 1 is shown in FIG. A9-3. DSC data showing the melting transitions of Modification A-9 and the total water loss (Loss on Drying—LOD) as measured by TGA are represented in Table 4.

The XRPD pattern of Modification A-9 of Example 1 is shown in FIG. A9-1. The XRPD peaks, when measured using a CuKα radiation with a wavelength of 1.5418 Å at a temperature of about 22° C., are as set forth in the following table:

| No. | Angle 2θ | d value Å | Relative Intensity % |
|---|---|---|---|
| 1 | 7.5 | 11.85 | 11 |
| 2 | 9.5 | 9.27 | 17 |
| 3 | 11.1 | 7.94 | 18 |
| 4 | 17.9 | 4.95 | 21 |
| 5 | 18.4 | 4.82 | 28 |
| 6 | 23.6 | 3.77 | 35 |
| 7 | 30.7 | 2.91 | 11 |
| 8 | 32.4 | 2.76 | 8 |

Modification A-10: Co-crystal of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) with phosphoric acid (1:0.97 molar ratio)

Compound C-1 of Example 1 (30 mg) and 1.5 equiv. phosphoric acid were dissolved in 0.6 mL acetone. The resulting mixture was dissolved at 50° C. and cooled to room temperature to yield a 1:0.97 molar ratio co-crystal of compound C-1 with phosphoric acid.

The DSC thermogram of Modification A-10 of Example 1 is shown in FIG. A10-2. The TGA of Modification A-10 of Example 1 is shown in FIG. A10-3. DSC data showing the melting transitions of Modification A-10 and the total water loss (Loss on Drying—LOD) as measured by TGA are represented in Table 4.

The XRPD pattern of Modification A-10 of Example 1 is shown in FIG. A10-1. The XRPD peaks, when measured using a CuKα radiation with a wavelength of 1.5418 Å at a temperature of about 22° C., are as set forth in the following table:

| No. | Angle 2θ | d value Å | Relative Intensity % |
|---|---|---|---|
| 1 | 7.5 | 11.82 | 5 |
| 2 | 9.5 | 9.35 | 27 |
| 3 | 11.1 | 7.97 | 17 |
| 4 | 13.2 | 6.69 | 6 |
| 5 | 13.6 | 6.48 | 5 |
| 6 | 15.0 | 5.91 | 11 |
| 7 | 18.1 | 4.90 | 25 |
| 8 | 18.4 | 4.82 | 28 |
| 9 | 19.0 | 4.67 | 6 |
| 10 | 23.8 | 3.73 | 36 |
| 11 | 25.9 | 3.44 | 11 |
| 12 | 27.5 | 3.24 | 10 |

Modification A-11: Co-crystal of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) with benzoic acid (1:1.01 molar ratio)

Compound C-1 (60 mg) and 28 mg (2 equiv.) benzoic acid were dissolved in 0.30 mL isopropanol. The resulting mixture was dissolved at 50° C. and cooled to room temperature to yield a 1:1.01 molar ratio co-crystal of compound C-1 with benzoic acid.

The DSC thermogram of Modification A-11 of Example 1 is shown in FIG. A11-2. The TGA of Modification A-11 of Example 1 is shown in FIG. A11-3. DSC data showing the melting transitions of Modification A-11 and the total water loss (Loss on Drying—LOD) as measured by TGA are represented in Table 4.

The XRPD pattern of Modification A-11 of Example 1 is shown in FIG. A11-1. The XRPD peaks, when measured using a CuKα radiation with a wavelength of 1.5418 Å at a temperature of about 22° C., are as set forth in the following table:

| No. | Angle 2θ | d value Å | Relative Intensity % |
|---|---|---|---|
| 1 | 6.1 | 14.42 | 15 |
| 2 | 9.1 | 9.72 | 9 |
| 3 | 10.3 | 8.54 | 25 |
| 4 | 11.3 | 7.82 | 14 |
| 5 | 12.3 | 7.21 | 58 |
| 6 | 12.7 | 6.95 | 12 |
| 7 | 14.9 | 5.92 | 8 |
| 8 | 15.3 | 5.79 | 7 |
| 9 | 16.8 | 5.29 | 19 |
| 10 | 17.1 | 5.17 | 9 |
| 11 | 20.8 | 4.26 | 11 |
| 12 | 24.7 | 3.60 | 40 |

Modification A-12: Co-crystal of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) with succinic acid (1:1.02 molar ratio)

Compound C-1 (1.0 g) and 2 equiv. succinic acid were dissolved in 5.2 mL isopropanol. The resulting mixture was dissolved at 50° C. and cooled to room temperature to yield a 1:1.02 molar ratio co-crystal of compound C-1 with succinic acid.

The DSC thermogram of Modification A-12 of Example 1 is shown in FIG. A12-2. The TGA of Modification A-12 of Example 1 is shown in FIG. A12-3. DSC data showing the melting transitions of Modification A-12 and the total water loss (Loss on Drying—LOD) as measured by TGA are represented in Table 4.

The XRPD pattern of Modification A-12 of Example 1 is shown in FIG. A12-1. The XRPD peaks, when measured using a CuKα radiation with a wavelength of 1.5418 Å at a temperature of about 22° C., are as set forth in the following table:

| No. | Angle 2θ | d value Å | Relative Intensity % |
|---|---|---|---|
| 1 | 6.8 | 12.96 | 58 |
| 2 | 8.7 | 10.16 | 32 |
| 3 | 10.5 | 8.40 | 6 |
| 4 | 15.6 | 5.68 | 11 |
| 5 | 16.4 | 5.40 | 45 |
| 6 | 17.4 | 5.08 | 5 |
| 7 | 19.2 | 4.61 | 10 |
| 8 | 21.1 | 4.20 | 48 |
| 9 | 24.1 | 3.69 | 18 |
| 10 | 24.6 | 3.61 | 7 |
| 11 | 27.5 | 3.24 | 23 |
| 12 | 28.4 | 3.14 | 4 |

Modification A-13: Co-crystal of 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide (compound C-1) with saccharin (1:0.50 molar ratio)

Compound C-1 (1.0 g) and 1.5 equiv. saccharin were dissolved in 20.0 mL isopropanol. The resulting mixture was dissolved at 50° C. and cooled to room temperature to yield a 1:0.50 molar ratio co-crystal of compound C-1 with saccharin.

The DSC thermogram of Modification A-13 of Example 1 is shown in FIG. A13-2. The TGA of Modification A-13 of Example 1 is shown in FIG. A13-3. DSC data showing the melting transitions of Modification A-13 and the total water loss (Loss on Drying—LOD) as measured by TGA are represented in Table 4.

The XRPD pattern of Modification A-13 of Example 1 is shown in FIG. A13-1. The XRPD peaks, when measured using a CuKα radiation with a wavelength of 1.5418 Å at a temperature of about 22° C., are as set forth in the following table:

| No. | Angle 2θ | d value Å | Relative Intensity % |
|---|---|---|---|
| 1 | 6.0 | 14.61 | 26 |
| 2 | 8.6 | 10.27 | 46 |
| 3 | 12.2 | 7.24 | 4 |
| 4 | 13.0 | 6.78 | 2 |
| 5 | 15.5 | 5.70 | 14 |
| 6 | 16.2 | 5.47 | 28 |
| 7 | 21.7 | 4.09 | 16 |
| 8 | 23.5 | 3.79 | 15 |
| 9 | 30.1 | 2.96 | 5 |
| 10 | 31.4 | 2.85 | 12 |

Example 2: 2-((8-Chloro-1-(2,6-dichloro-4-(2-hydroxyethoxy)phenyl)-2-methyl-4-oxo-1,4-dihydro-1,6-naphthyridin-5-yl)oxy)-N-(2-hydroxyethyl)acetamide (Compound C-2)

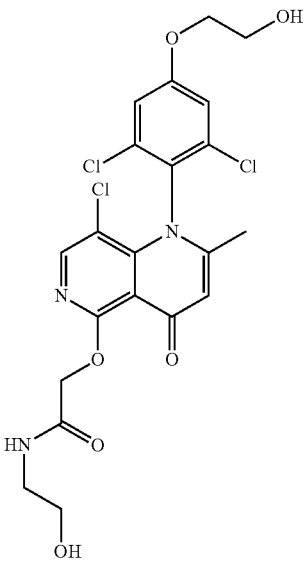 [SMILES: Cc1cc(=O)c2c(OCC(=O)NCCO)ncc(Cl)c2n1-c1c(Cl)cc(OCCO)cc1Cl]

Step 1: Methyl 2-((1-(4-bromo-2,6-dichlorophenyl)-8-chloro-2-methyl-4-oxo-1,4-dihydro-1,6-naphthyridin-5-yl)oxy)acetate To a stirred solution of 1-(4-bromo-2,6-dichlorophenyl)-5,8-dichloro-2-methyl-1,6-naphthyridin-4(1H)-one (intermediate F2, 2.5 g, 2.21 mmol) in $CH_3CN$ (25 mL), was added methyl glycolate (0.24 g, 2.65 mmol), potassium carbonate (0.92 g, 6.62 mmol) and DMAP (0.09 g, 0.66 mmol). The resulting reaction mixture was stirred at 80° C. for 12 h. The reaction mixture was filtered off and rinsed with $CH_3CN$. The organic layer was concentrated in vacuo. The residue was purified by MPLC using a 40 g silica-gel column and 10-65% EtOAc in hexane to get the title product as off white solid (2.4 g, 82% yield). ESI-MS m/z: 504.8 [M+H]$^+$ (Rt=1.55 min, LC-method 6).

Step 2: (3,5-Dichloro-4-(8-chloro-5-(2-methoxy-2-oxoethoxy)-2-methyl-4-oxo-1,6-naphthyridin-1(4H)-yl)phenyl)boronic acid To a degassed (with argon) solution of methyl 2-((1-(4-bromo-2,6-dichlorophenyl)-8-chloro-2-methyl-4-oxo-1,4-dihydro-1,6-naphthyridin-5-yl)oxy)acetate (2.3 g, 4.55 mmol) in 1,4-dioxane (25 mL), in a screw capped sealed tube, was added bis(pinacolato)diboron (1.73 g, 6.82 mmol), potassium acetate (0.67 g, 6.82 mmol), PdCl$_2$(dppf) and DCM (0.37 g, 0.45 mmol). The reaction mixture was stirred at 90° C. for 8 h. The reaction mixture was filtered through a pad of Celite and rinsed with 1,4-dioxane. The filtrate was concentrated in vacuo to the crude title product (2.14 g, crude). ESI-MS m/z: 470.80 [M+H]$^+$ (Rt=1.41 min, LC-method 1).

Step 3: Methyl 2-((8-chloro-1-(2,6-dichloro-4-hydroxyphenyl)-2-methyl-4-oxo-1,4-dihydro-1,6-naphthyridin-5-yl)oxy)acetate To a solution of (3,5-dichloro-4-(8-chloro-5-(2-methoxy-2-oxoethoxy)-2-methyl-4-oxo-1,6-naphthyridin-1(4H)-yl) phenyl)boronic acid (1.94 g, 4.11 mmol) in MeOH:H$_2$O (10 mL: 10 mL) at 0° C. was added Montmorillonite K10 (1.69 g, 6.17 mmol) and 30% hydrogen peroxide (10 mL) dropwise at same temperature. The solution was stirred at room temperature for 2 h. The reaction mixture was concentrated in vacuo to get the crude product. The crude product was purified by MPLC using 24.0 g silica-gel column and 1-5% MeOH in dichloromethane to get the title product as brown solid (1.3 g, yield: 71%). ESI-MS m/z: 442.90 [M−H]$^+$ (Rt=1.43 min, LC-method 6).

Step 4: 2-((8-Chloro-1-(2,6-dichloro-4-hydroxyphenyl)-2-methyl-4-oxo-1,4-dihydro-1,6-naphthyridin-5-yl)oxy)acetic acid To a solution of methyl 2-((8-chloro-1-(2,6-dichloro-4-hydroxyphenyl)-2-methyl-4-oxo-1,4-dihydro-1,6-naphthyridin-5-yl)oxy)acetate (0.5 g, 1.13 mmol) in 1,2-dichloroethane (6 mL) was added trimethyltin hydroxide (2.05 g, 11.29 mmol). The solution so obtained was stirred at room temperature for 5 min, and then at 80° C. for 12 h. The volatiles were evaporated under reduced pressure to get the residue. The residue was acidified with 10% KHSO$_4$ and extracted with 10% MeOH in dichloromethane. The combined organic layers were washed with brine, dried over anhydrous sodium sulfate, and concentrated under reduced pressure to get the desired product as pale brown solid (0.23 g, yield: 42%). ESI-MS m/z: 429.00 [M+H]$^+$ (Rt=1.38 min, LC-method 6).

Step 5: N-(2-((tert-Butyldimethylsilyl)oxy)ethyl)-2-((8-chloro-1-(2,6-dichloro-4-hydroxyphenyl)-2-methyl-4-oxo-1,4-dihydro-1,6-naphthyridin-5-yl)oxy)acetamide To a solution of 2-((8-chloro-1-(2,6-dichloro-4-hydroxyphenyl)-2-methyl-4-oxo-1,4-dihydro-1,6-naphthyridin-5-yl) oxy)acetic acid (0.2 g, 0.48 mmol) in DMF (3 mL) was added HATU (0.36 g, 0.95 mmol). The solution so obtained was stirred at room temperature for 5 min. To this solution was added 2-((tert-butyldimethylsilyl)oxy)ethan-1-amine (0.1 g, 0.57 mmol) and DIPEA (0.15 g, 1.19 mmol) and the resulting solution was stirred at room temperature for 12 h. The reaction mixture was diluted with water and extracted with EtOAc. The combined organic layers were washed with brine, dried over anhydrous sodium sulfate, and concentrated under reduced pressure to get the title product as pale brown solid (0.22 g, yield: 79%). ESI-MS m/z: 586.15 [M+H]$^+$ (Rt=1.63 min, LC-method 6).

Step 6: N-(2-((tert-Butyldimethylsilyl)oxy)ethyl)-2-((8-chloro-1-(2,6-dichloro-4-(2-hydroxyethoxy)phenyl)-2-methyl-4-oxo-1,4-dihydro-1,6-naphthyridin-5-yl)oxy)acetamide To a solution of N-(2-((tert-butyldimethylsilyl)oxy) ethyl)-2-((8-chloro-1-(2,6-dichloro-4-hydroxyphenyl)-2-methyl-4-oxo-1,4-dihydro-1,6-naphthyridin-5-yl)oxy)acetamide (0.22 g, 0.38 mmol) in DMF (3 mL) was added silver carbonate (0.31 g, 1.12 mmol) and 2-bromoethanol (0.07 g; 0.56 mmol). The resulting reaction mixture was stirred at 80° C. for 12 h. The reaction mixture was diluted with water and extracted with EtOAc. The combined organic layers were washed with brine, dried over anhydrous sodium sulfate, and concentrated under reduced pressure to get the crude product. The crude product was purified by MPLC using 12.0 g silica-gel column and 20-60% EtOAc in hexane to get the title product as pale brown solid (0.13 g, yield: 56%). ESI-MS m/z: 630.15 [M+H]$^+$ (Rt=1.59 min, LC-method 6).

Step 7: 2-((8-Chloro-1-(2,6-dichloro-4-(2-hydroxyethoxy)phenyl)-2-methyl-4-oxo-1,4-dihydro-1,6-naphthyridin-5-yl)oxy)-N-(2-hydroxyethyl)acetamide To a solution of N-(2-((tert-butyldimethylsilyl)oxy) ethyl)-2-((8-chloro-1-(2,6-dichloro-4-(2-hydroxyethoxy) phenyl)-2-methyl-4-oxo-1,4-dihydro-1,6-naphthyridin-5-yl) oxy)acetamide (0.13 g, 0.21 mmol) in dry dioxane (2 mL) was added 4.0 HCl in 1,4-dioxane (2 mL) at 0° C. The solution so obtained was stirred at ambient temperature for 1 h. The volatiles were evaporated under reduced pressure to get the residue. The residue was dissolved in ethyl acetate and washed with saturated sodium bicarbonate solution. The organic layer was washed with brine, dried over anhydrous sodium sulfate, and concentrated under reduced pressure to get the crude product. The crude product was purified by preparative HPLC (Column: X SELECT (250 mm×19.0 mm, 5.0 m); mobile phase: 0.02% NH$_4$OH in water, and acetonitrile; gradient elution). The fractions were lyophilized to get the title product as off-white powder (0.046 g, yield: 30%). C-2: ESI-MS m/z: 516.05 [M+H]$^+$ (Rt=1.35 min, LC-method 6); $^1$H NMR (300 MHz, CHLOROFORM-d3) δ ppm=8.21 (s, 1H), 7.27 (s, 2H), 6.55 (s, 1H), 4.92 (s, 2H), 4.18 (t, J=4.2 Hz, 2H), 3.92 (t, J=4.5 Hz, 2H), 3.71 (t, J=6.0 Hz, 2H), 3.49 (t, J=6.0 Hz, 2H), 2.04 (S, 3H).

Example 3: 3-((8-Chloro-1-(2,6-dichloro-4-(2-hydroxy-2-methylpropoxy)phenyl)-2-methyl-4-oxo-1,4-dihydro-1,6-naphthyridin-5-yl)oxy)-N-methylpropanamide (Compound C-3)

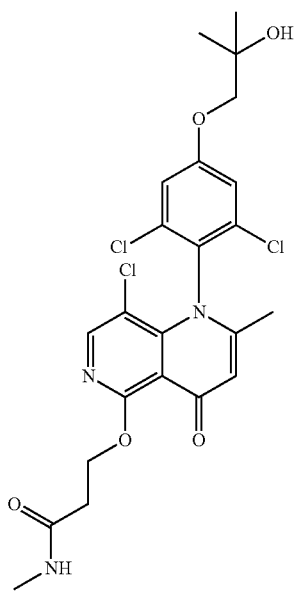 [SMILES: CNC(=O)CCOc1ncc(Cl)c2c1c(=O)cc(C)n2-c1c(Cl)cc(OCC(C)(C)O)cc1Cl]

Step 1: 3-((8-Chloro-1-(2,6-dichloro-4-fluorophenyl)-2-methyl-4-oxo-1,4-dihydro-1,6-naphthyridin-5-yl)oxy)-N-methylpropanamide To a solution of 5,8-dichloro-1-(2,6-dichloro-4-fluorophenyl)-2-methyl-1,6-naphthyridin-4(1H)-one (intermediate F1, 1.0 g, 2.55 mmol) in acetonitrile (10 mL), was added 3-hydroxy-N-methylpropanamide (0.32 g, 3.06 mmol), $K_2CO_3$ (0.88 g, 6.38 mmol) and DMAP (0.09 g, 0.77 mmol). The reaction mixture was stirred at 80° C. for 16 h. The reaction mixture was diluted with water and extracted with EtOAc. The combined organic layers were washed with brine, dried over $Na_2SO_4$, filtered, and concentrated under reduced pressure to get the crude product. The crude product was purified by MPLC using 40 g of a Silicycle cartridge and 0-2% MeOH in dichloromethane as eluent to get the title product as an off white solid (0.78 g, yield: 67%). ESI-MS m/z: 458.1 [M+1]$^+$ (Rt=1.40 min, LC-method-5).

Step 2: 3-((8-Chloro-1-(2,6-dichloro-4-(2-hydroxy-2-methylpropoxy)phenyl)-2-methyl-4-oxo-1,4-dihydro-1,6-naphthyridin-5-yl)oxy)-N-methylpropanamide To a stirred solution of 3-((8-chloro-1-(2,6-dichloro-4-fluorophenyl)-2-methyl-4-oxo-1,4-dihydro-1,6-naphthyridin-5-yl)oxy)-N-methylpropanamide (0.78 g, 1.71 mmol) in DMF (8 mL) were added 2-methylpropane-1,2-diol (0.46 g, 5.12 mmol) and $Cs_2CO_3$ (1.67 g, 5.12 mmol). The resulting reaction mixture was stirred at room temperature for 4 h. The reaction mixture was diluted with water and extracted with EtOAc. The combined organic layers were washed with brine, dried over $Na_2SO_4$, filtered, and concentrated under reduced pressure to get crude product. The crude product was purified by MPLC using 40 g of a Silicycle cartridge and 0-2% MeOH in dichloromethane as eluent to get the title product as off white solid (0.22 g, yield: 24%). C-3: ESI-MS m/z: 527.90 [M+H]$^+$ (Rt=1.42 min, LC-method-6). $^1$H NMR (400 MHz, METHANOL-d4) δ ppm=8.19 (s, 1H), 7.27 (s, 2H), 6.51 (s, 1H), 4.66 (t, J=5.6 Hz, 2H), 3.91 (s, 2H), 2.78 (s, 3H), 2.76 (t, J=6.0 Hz, 2H), 2.03 (s, 3H), 1.33 (s, 6H).

Example 4: 2-((8-Chloro-1-(2,6-dichloro-4-(2-hydroxy-2-methylpropoxy)phenyl)-2-methyl-4-oxo-1,4-dihydro-1,6-naphthyridin-5-yl)oxy)-N-methylacetamide (Compound C-4)

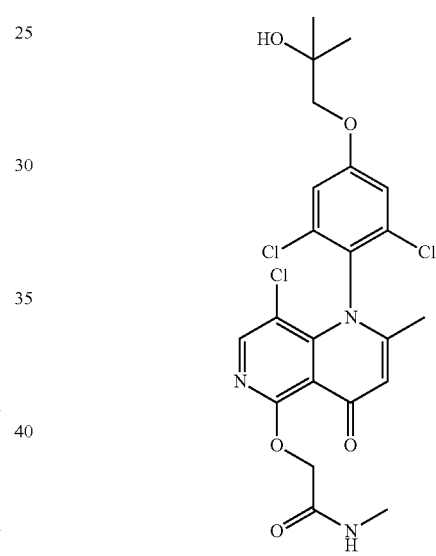

Step 1: 2-((8-Chloro-1-(2,6-dichloro-4-fluorophenyl)-2-methyl-4-oxo-1,4-dihydro-1,6-naphthyridin-5-yl)oxy)-N-methylacetamide To a stirred solution of 5,8-dichloro-1-(2,6-dichloro-4-fluorophenyl)-2-methyl-1,6-naphthyridin-4(1H)-one (intermediate F1, 0.3 g, 0.76 mmol) in acetonitrile (8 mL) was added $K_2CO_3$ (0.31 g, 2.29 mmol) DMAP (0.03 g, 0.22 mmol) and 2-hydroxy-N-methylacetamide (0.1 g, 1.14 mmol). The reaction mixture was heated at 80° C. for 16 h. The reaction mixture was diluted with water and extracted with EtOAc. The combined organic layers were washed with brine, dried over $Na_2SO_4$, filtered, and concentrated under reduced pressure to get the crude product. The crude product was purified by MPLC using a 12 g Silicycle cartridge and 0-2% MeOH in dichloromethane as eluent to get the title product as white solid. (0.2 g, yield: 59%). ESI-MS m/z: 444.0 [M+H]$^+$ (Rt=1.48 min, LC-method 6).

Step 2: 2-((8-Chloro-1-(2,6-dichloro-4-(2-hydroxy-2-methylpropoxy)phenyl)-2-methyl-4-oxo-1,4-dihydro-1,6-naphthyridin-5-yl)oxy)-N-methylacetamide To a stirred solution of 2-((8-chloro-1-(2,6-dichloro-4-fluorophenyl)-2-methyl-4-oxo-1,4-dihydro-1,6-naphthyridin-5-yl)oxy)-N-methylacetamide (0.13 g, 0.29 mmol) in DMF (5 mL) was added Cs$_2$CO$_3$ (0.28 g, 0.87 mmol) and 2-methylpropane-1,2-diol (0.04 g, 0.43 mmol). The reaction mixture was stirred at ambient temperature for 16 h. The reaction mixture was diluted with water and extracted with EtOAc. The combined organic layers were washed with brine, dried over Na$_2$SO$_4$, filtered, and concentrated under reduced pressure to get crude product. The crude product was purified by MPLC using 12 g Silicycle cartridge and 0-5% MeOH in dichloromethane as eluent and preparative HPLC (column: X SELECT C-18 (250 mm×19 mm, 5.0 μm); mobile phase: 0.1% formic acid in water and acetonitrile; gradient elution) to get the title product as an off white solid (0.023 g, yield: 15%). C-4: ESI-MS m/z: 514.05 [M+H]$^+$ (Rt=1.42 min, LC-method 6); $^1$H NMR (300 MHz, METHANOL-d4) δ ppm=8.21 (s, 1H), 7.28 (s, 2H), 6.55 (s, 1H), 4.91 (s, 2H), 3.91 (s, 2H), 2.89 (s, 3H), 2.05 (s, 3H), 1.33 (s, 6H).

Example 5: 2-((8-Chloro-1-(2,6-dichloro-4-(2-hydroxyethoxy)phenyl)-2-methyl-4-oxo-1,4-dihydro-1,6-naphthyridin-5-yl)oxy)-N-methylacetamide (Compound C-5)

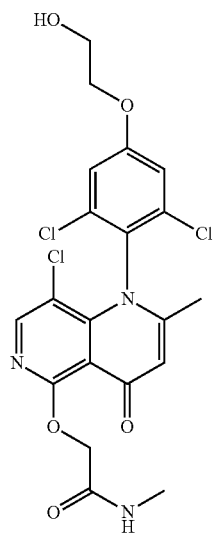 [SMILES: CNC(=O)COc1ncc(Cl)c2c1c(=O)cc(C)n2-c1c(Cl)cc(OCCO)cc1Cl]

0.027 g (yield: 22%) of an off-white colored powder of Example 5 was prepared in an analogous way to Example 4 using step-1 intermediate of Example 4 and ethylene glycol. C-5: ESI-MS m/z: 486.05 [M+H]$^+$ (Rt=1.38 min, LC-method 6); $^1$H NMR (400 MHz, CHLOROFORM-d3) δ ppm=8.8 (brs, 1H), 8.10 (s, 1H), 7.03 (s, 2H), 6.44 (s, 1H), 4.91 (s, 2H), 4.17 (t, J=4.4 Hz, 2H), 4.05 (t, J=5.2 Hz, 2H), 2.98 (d, J=4.8 Hz, 3H), 2.08 (t, 1H), 1.97 (s, 3H).

Example 6: (R)-3-((8-Chloro-1-(2,6-dichloro-4-(2-hydroxypropoxy)phenyl)-2-methyl-4-oxo-1,4-dihydro-1,6-naphthyridin-5-yl)oxy)-N-methylpropanamide (Compound C-6)

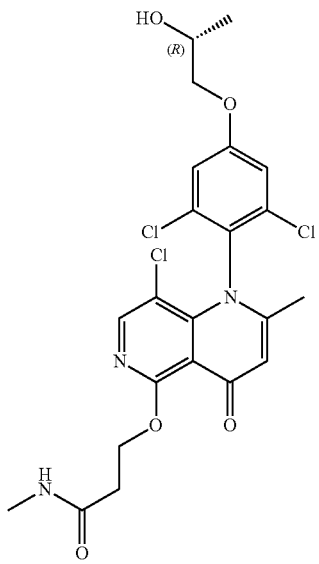

To a stirred solution of 3-((8-chloro-1-(2,6-dichloro-4-fluorophenyl)-2-methyl-4-oxo-1,4-dihydro-1,6-naphthyridin-5-yl)oxy)-N-methylpropanamide (0.4 g, 0.87 mmol) [step-1 of Example 3)] in DMF (10 mL) was added (R)-propane-1,2-diol (0.17 g, 1.31 mmol) and Cs$_2$CO$_3$ (0.09 g, 2.62 mmol). The reaction mixture was stirred at 50° C. for 3 h. The reaction mixture was partitioned between water and EtOAc. The organic layer was separated, washed with brine, dried over anhydrous sodium sulphate, and evaporated under reduced pressure to get the crude product. The crude compound was purified by MPLC using 24 g Silicycle cartridge and 0-10% methanol in dichloromethane to get the mixture of regio-isomers as pale yellow solid (0.23 g, yield: 51%). The regio isomers were separated by chiral prep. HPLC [LUX CELLULOSE-4, C-18 (250 mm×21.2 mm, 5.0 μm) column; hexane (A) and 0.1% HCOOH in IPA: MeOH (1:1) (B); isocratic elution] to get the title product as an off-white powder (0.15 g, yield: 68%). C-6: ESI-MS m/z: 514.0 [M+H]$^+$ (Rt=0.71 min, LC-method 2); $^1$H NMR (300 MHz, CD$_3$OD) δ ppm=8.19 (s, 1H), 7.26 (s, 2H), 6.51 (s, 1H), 4.67 (t, J=5.7 Hz, 2H), 4.14-3.94 (m, 3H), 2.78-2.72 (m, 5H), 2.02 (s, 3H), 1.29 (d, J=6.3 Hz, 3H).

Example 7: (R)-3-((8-Chloro-1-(2,6-dichloro-4-(2-hydroxyethoxy)phenyl)-2-methyl-4-oxo-1,4-dihydro-1,6-naphthyridin-5-yl)oxy)-N,2-dimethylpropanamide (Compound C-7)

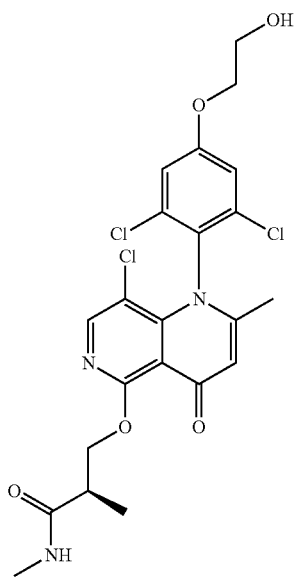 [SMILES: CNC(=O)[C@H](C)COc1ncc(Cl)c2c1c(=O)cc(C)n2-c1c(Cl)cc(OCCO)cc1Cl]

Step 1: (R)-3-hydroxy-N,2-dimethylpropanamide

To a stirred solution of methyl (R)-3-hydroxy-2-methylpropanoate (0.5 g, 4.24 mmol) in MeOH (5 mL) in a screw capped sealed tube was added 40% methylamine in methanol (20.5 mL, 114.34 mmol). The contents of sealed tube were stirred at 85° C. for 20 h. The reaction mixture was evaporated under reduced pressure to get the title product as a yellow solid (0.45 g, 95%). $^1$H NMR (400 MHz, CHLOROFORM-d3) δ ppm=5.98 (bs, 1H), 3.72 (m, 2H), 2.82 (d, 3H), 2.47 (m, 1H), 1.172 (d, 3H).

Step 2: (R)-3-((8-chloro-1-(2,6-dichloro-4-fluorophenyl)-2-methyl-4-oxo-1,4-dihydro-1,6-naphthyridin-5-yl)oxy)-N,2-dimethylpropanamide To a solution of 5,8-dichloro-1-(2,6-dichloro-4-fluorophenyl)-2-methyl-1,6-naphthyridin-4(1H)-one (intermediate F1, 0.3 g, 0.77 mmol) in acetonitrile (4.00 mL), was added (R)-3-hydroxy-N,2-dimethylpropanamide (0.11 g, 0.92 mmol), K$_2$CO$_3$ (0.26 g, 1.91 mmol), and DMAP (0.03 g, 0.23 mmol). The resulting reaction mixture was stirred at 80° C. for 16 h. The reaction mixture was diluted with water and extracted with EtOAc. The organic layer was washed with brine, dried over anhydrous sodium sulphate, and evaporated under reduced pressure to get the crude product. The crude compound was purified by MPLC using 12 g Silicycle cartridge and 0-3% of MeOH in dichloromethane to get the title product as an off-white solid (0.25 g, yield: 69%). ESI-MS m/z: 471.8 [M+H]$^+$ (Rt=1.49 min, LC-method-6).

Step 3: (R)-3-((8-Chloro-1-(2,6-dichloro-4-(2-hydroxyethoxy)phenyl)-2-methyl-4-oxo-1,4-dihydro-1,6-naphthyridin-5-yl)oxy)-N,2-dimethylpropanamide To a stirred solution of (R)-3-((8-chloro-1-(2,6-dichloro-4-fluorophenyl)-2-methyl-4-oxo-1,4-dihydro-1,6-naphthyridin-5-yl)oxy)-N,2-dimethylpropanamide (0.24 g, 0.51 mmol) in DMF (3 mL) was added ethylene glycol (0.09 g, 1.53 mmol), and Cs$_2$CO$_3$ (0.49 g, 1.53 mmol). The reaction mixture was stirred at ambient temperature for 4 h. The reaction mixture was diluted with water and extracted with EtOAc. The organic layer was washed with brine, dried over anhydrous sodium sulphate, and evaporated under reduced pressure to get the crude product. The crude compound was purified by MPLC using 12 g Silicycle cartridge and 0-3% of MeOH in dichloromethane to get the title product as off-white solid (0.071 g, yield: 27%). C-7: ESI-MS m/z: 513.9 [M+H]$^+$ (Rt=1.39 min, LC-method-6). ESI-MS m/z: 515.90 [M+3H]$^+$ (Rt=1.39 min, LC-method-6). $^1$H NMR (400 MHz, CD$_3$OD) δ ppm=8.18 (s, 1H), 7.26 (s, 2H), 6.51 (s, 1H), 4.49-4.45 (m, 2H), 4.17 (t, J=4.8 Hz, 2H), 3.91 (t, J=5.2 Hz, 2H), 2.83-279 (m, 1H), 2.77 (s, 3H), 2.026 (s, 3H), 1.27 (d, J=7.2 Hz, 3H).

Example 8: (S)-3-((8-Chloro-1-(2,6-dichloro-4-(2-hydroxyethoxy)phenyl)-2-methyl-4-oxo-1,4-dihydro-1,6-naphthyridin-5-yl)oxy)-N,2-dimethylpropanamide (Compound C-8)

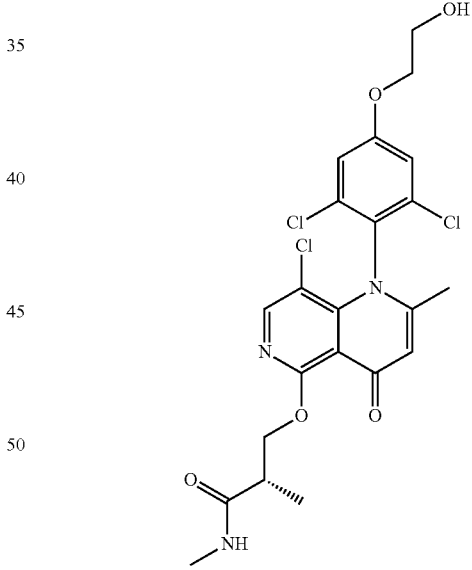

0.038 g (off-white solid, yield: 18%) of Example 8 was prepared in an analogous way to Example 7 using (S)-3-hydroxy-2-methylpropanoate instead of (R)-3-hydroxy-2-methylpropanoate. The crude product was purified by preparative HPLC (column: X-select C-18 (19 mm×250 mm, μm); mobile phase: 0.1% HCOOH in water, and acetonitrile; gradient elution). C-8: ESI-MS m/z: 514.2 [M+H]$^+$ (Rt=0.78 min, LC-method-5). $^1$H NMR (400 MHz, METHANOL-d4) δ ppm=8.18 (s, 1H), 7.26 (s, 2H), 6.51 (s, 1H), 4.49-4.45 (m, 2H), 4.18 (t, J=4.4 Hz, 2H), 3.91 (t, J=5.2 Hz, 2H), 2.90 (m, 1H), 2.77 (s, 3H), 2.03 (s, 3H), 1.27 (d, J=7.2 Hz, 3H).

Example 9: N-(2-((8-chloro-1-(2,6-dichloro-4-(2-hydroxyethoxy)phenyl)-2-methyl-4-oxo-1,4-dihydro-1,6-naphthyridin-5-yl)oxy)ethyl)acetamide (Compound C-9)

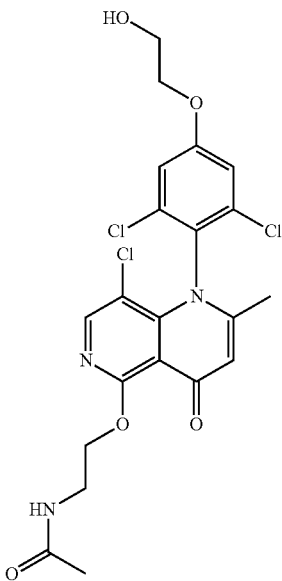 [SMILES: CC(=O)NCCOc1ncc(Cl)c2c1c(=O)cc(C)n2-c1c(Cl)cc(OCCO)cc1Cl]

Step 1: tert-Butyl (2-((8-chloro-1-(2,6-dichloro-4-fluorophenyl)-2-methyl-4-oxo-1,4-dihydro-1,6-naphthyridin-5-yl)oxy)ethyl)carbamate To a stirred solution of 5,8-dichloro-1-(2,6-dichloro-4-fluorophenyl)-2-methyl-1,6-naphthyridin-4(1H)-one (intermediate F1, 0.7 g, 1.79 mmol) in acetonitrile (20 mL) was added tert-butyl (2-aminoethyl) carbamate (0.35 g, 2.14 mmol), $K_2CO_3$ (0.74 g, 5.36 mmol) and DMAP (0.07 g, 0.54 mmol). The reaction mixture was stirred at 80° C. for 6 h. The reaction mixture was partitioned between water and EtOAc and the aqueous layer was extracted with EtOAc. The organic layer was washed with brine, dried over anhydrous sodium sulfate and evaporated under reduced pressure to get the crude product. The crude compound was purified by MPLC using 12 g Silicycle cartridge and 20-100% ethyl acetate in hexane to get the title product as an off-white solid (0.62 g, yield: 67%). ESI-MS m/z: 516.6 (M+H)+ (Rt=1.79 min, LC-method 4).

Step 2: 5-(2-Aminoethoxy)-8-chloro-1-(2,6-dichloro-4-fluorophenyl)-2-methyl-1,6-naphthyridin-4(1H)-one hydrochloride To a stirred solution of tert-butyl (2-((8-chloro-1-(2,6-dichloro-4-fluorophenyl)-2-methyl-4-oxo-1,4-dihydro-1,6-naphthyridin-5-yl)oxy)ethyl)carbamate (0.6 g, 1.16 mmol) in dioxane (5 mL) was added 4.0 M HCl in 1,4-dioxane (10 mL). The reaction mixture was stirred at 30° C. for 6 h. The volatiles were evaporated under reduced pressure to get the title product as an off-white solid (0.55 g, yield: 100%). The obtained product was used directly in the next step.

Step 3: N-(2-((8-Chloro-1-(2,6-dichloro-4-fluorophenyl)-2-methyl-4-oxo-1,4-dihydro-1,6-naphthyridin-5-yl)oxy)ethyl)acetamide To a suspension of 5-(2-aminoethoxy)-8-chloro-1-(2,6-dichloro-4-fluorophenyl)-2-methyl-1,6-naphthyridin-4(1H)-one hydrochloride (0.54 g, 1.213 mmol) in dichloromethane (10 mL) at 0° C., was added triethylamine (0.49 mL, 3.64 mmol) and acetyl chloride (0.12 mL, 1.82 mmol). The reaction mixture was stirred at 30° C. for 5 h. The reaction mixture was partitioned between water and EtOAc and the aqueous layer was extracted with EtOAc. The organic layer was washed with brine, dried over anhydrous sodium sulphate, and evaporated under reduced pressure to get the crude product. The crude product was purified by MPLC using 24 g Silicycle cartridge and 20-70% ethyl acetate in hexane to get the title product as a yellow semi-solid (0.45 g, yield: 81%). ESI-MS m/z: 458.0 (M+H)+ (Rt=1.29 min, LC-method 5).

Step 4: N-(2-((8-Chloro-1-(2,6-dichloro-4-(2-hydroxyethoxy)phenyl)-2-methyl-4-oxo-1,4-dihydro-1,6-naphthyridin-5-yl)oxy)ethyl)acetamide To a stirred solution of N-(2-((8-chloro-1-(2,6-dichloro-4-fluorophenyl)-2-methyl-4-oxo-1,4-dihydro-1,6-naphthyridin-5-yl)oxy)ethyl)acetamide (0.2 g, 0.44 mmol) in DMF (5 mL) was added ethylene glycol (0.04 g, 0.65 mmol) and $Cs_2CO_3$ (0.43 g, 1.31 mmol). The reaction mixture was stirred at 30° C. for 6 h. The organic layer was washed with brine, dried over anhydrous sodium sulphate, and evaporated under reduced pressure to get the crude product. The crude product was purified by MPLC using 24 g Silicycle cartridge and 0-5% methanol in dichloromethane to get the title product as an off-white powder (0.058 g, yield: 32%). C-9: ESI-MS m/z: 499.85 [M+H]+ (Rt=1.35 min, LC-method 6); $^1$H NMR (300 MHz, METHANOL-d4) δ ppm=8.18 (s, 1H), 7.26 (s, 2H), 6.53 (s, 1H), 4.55 (t, J=5.1 Hz, 2H), 4.18 (t J=4.2 Hz, 2H), 3.92 (t J=4.5 Hz, 2H), 3.65 (t, J=5.4 Hz, 2H), 2.03 (s, 3H), 1.97 (s, 3H).

Example 10: (S)-3-((8-Chloro-1-(2,6-dichloro-4-(2-hydroxypropoxy)phenyl)-2-methyl-4-oxo-1,4-dihydro-1,6-naphthyridin-5-yl)oxy)-N-methylpropanamide (Compound C-10)

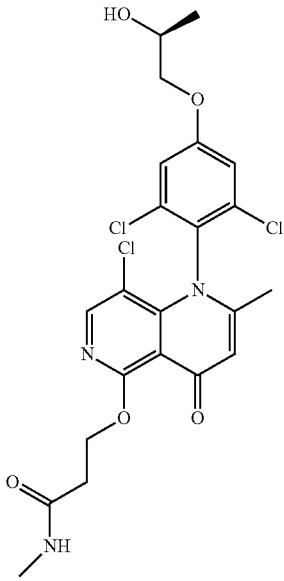 [SMILES: CNC(=O)CCOc1ncc(Cl)c2c1c(=O)cc(C)n2-c1c(Cl)cc(OC[C@H](C)O)cc1Cl]

To a stirred solution of 3-((8-chloro-1-(2,6-dichloro-4-fluorophenyl)-2-methyl-4-oxo-1,4-dihydro-1,6-naphthyridin-5-yl)oxy)-N-methylpropanamide [step-1 of Example 1]⁺ (0.450 g, 0.98 mmol) in DMF (5 mL) was added (S)-propane-1,2-diol (0.11 g, 1.47 mmol) and potassium carbonate (0.19 g, 1.39 mmol). The reaction mass was stirred at 80° C. for 24 h. The reaction mixture was partitioned between water and EtOAc. The combined organic phases were washed with water, brine, dried over Na$_2$SO$_4$ and evaporated under reduced pressure to yield the crude product. The crude product was purified by MPLC (Combi-Flash, 12 g Redisep column, and 0-15% MeOH in dichloromethane) and preparative HPLC (column: Kinetex C18 (150 mm×21.2 mm, 5.0 pun) column; mobile phase: water and acetonitrile; gradient elution) to get the title product as an off-white solid (0.024 g, yield: 10%). C-10: ESI-MS m/z: 514.4 [M+H]⁺ (Rt=0.78 min, LC-method 5); ¹H NMR (300 MHz, CHLOROFORM-d3) δ ppm=8.73 (s, 1H), 8.09 (s, 1H), 7.02 (s, 2H), 6.43 (s, 1H), 5.29 (s, 1H), 4.57-4.59 (m, 2H), 4.26-4.36 (m, 1H), 4.01-3.88 (m, 2H), 2.88 (d, J=3.2 Hz, 3H), 2.77-2.72 (m, 2H), 2.29-2.27 (m, 1H), 1.96 (s, 3H), 1.34 (d, J=4.5 Hz, 3H).

Example 11: 3-((8-Chloro-1-(2,6-dichloro-4-(2-hydroxyethoxy)phenyl)-2-methyl-4-oxo-1,4-dihydro-1,6-naphthyridin-5-yl)oxy)-N,2,2-trimethylpropanamide (Compound C-11)

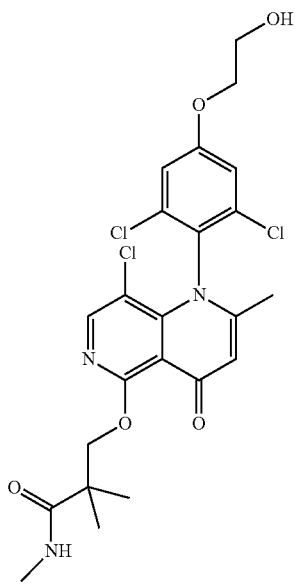 [SMILES: CNC(=O)C(C)(C)COc1ncc(Cl)c2c1c(=O)cc(C)n2-c1c(Cl)cc(OCCO)cc1Cl]

Step 1: 3-Hydroxy-N,2,2-trimethylpropanamide

To a stirred solution of methyl 3-hydroxy-2,2-dimethylpropanoate (0.5 g; 4.23 mmol) in MeOH (12 mL) in a screw capped sealed tube was added 40% methylamine in methanol (12 mL, 114.28 mmol). The resulting solution was stirred at 85° C. for 12 h. The volatiles were evaporated under high vacuum to get the title product (0.5 g, yield: 100%). ¹H NMR (400 MHz, CHLOROFORM-d3) δ ppm=3.70 (s, 2H), 2.80 (t, J=4.8 Hz, 3H), 1.19 (s, 3H), 1.17 (s, 3H).

Step 2: 3-((8-Chloro-1-(2,6-dichloro-4-fluorophenyl)-2-methyl-4-oxo-1,4-dihydro-1,6-naphthyridin-5-yl)oxy)-N,2,2-trimethylpropanamide To a stirred solution of 5,8-dichloro-1-(2,6-dichloro-4-fluorophenyl)-2-methyl-1,6-naphthyridin-4(1H)-one (intermediate F1, 0.25 g; 0.64 mmol) and 3-hydroxy-N,2,2-trimethylpropanamide (0.13 g, 0.96 mmol) in acetonitrile (2.5 mL) was added potassium carbonate (0.22 g, 1.59 mmol) and DMAP (0.02 g, 0.19 mmol). The resulting reaction mixture was stirred at 80° C. for 16 h. The reaction mixture was partitioned between water and EtOAc. The combined organic phases were washed with water, brine, dried over Na$_2$SO$_4$ and evaporated under reduced pressure to yield the crude product. The crude product was purified by MPLC (Combi-Flash, 12 g Redisep column, and 20-100% ethyl acetate in hexane) to get the title product as off-white solid (0.2 g, yield: 64%). ESI-MS m/z: 486.3 [M+H]⁺ (Rt=1.68 min, LC-method 5).

Step 3: 3-((8-Chloro-1-(2,6-dichloro-4-(2-hydroxyethoxy)phenyl)-2-methyl-4-oxo-1,4-dihydro-1,6-naphthyridin-5-yl)oxy)-N,2,2-trimethylpropanamide To a solution of 3-((8-chloro-1-(2,6-dichloro-4-fluorophenyl)-2-methyl-4-oxo-1,4-dihydro-1,6-naphthyridin-5-yl)oxy)-N,2,2-trimethylpropanamide (0.2 g, 0.41 mmol) and ethylene glycol (0.1 g, 1.64 mmol) in DMF (3 mL) was added cesium carbonate (0.47 g, 1.44 mmol). The resulting reaction mixture was stirred at room temperature for 5 h. The reaction mixture was partitioned between water and EtOAc. The combined organic phases were washed with water, brine, dried over Na$_2$SO$_4$ and evaporated under reduced pressure to yield the crude product. The crude product was purified by MPLC (Combi-Flash, 12 g Rediff column, and 0-3% methanol in dichloromethane) and preparative HPLC (column: YMC-C18 (20 mm×150 mm, 5.0 μm); mobile phase: 0.02% ammonia in water and acetonitrile, gradient elution) to get the title product as off-white solid (0.065 g, yield: 34%). C-11: ESI-MS m/z: 528.2 [M+H]⁺ (Rt=1.37 min, LC-method 5); ¹H NMR (300 MHz, METHANOL-d4) δ ppm=8.19 (s, 1H), 7.27 (s, 2H), 6.53 (s, 1H), 4.33 (s, 2H), 4.17 (s, 2H), 3.91 (s, 2H), 2.79 (s, 3H), 2.04 (s, 3H), 1.29 (s, 6H).

Example 12: (R)-3-((8-Chloro-1-(2,6-dichloro-4-(2-hydroxyethoxy)phenyl)-2-methyl-4-oxo-1,4-dihydro-1,6-naphthyridin-5-yl)oxy)-2-hydroxy-N-methylpropanamide (Compound C-12)

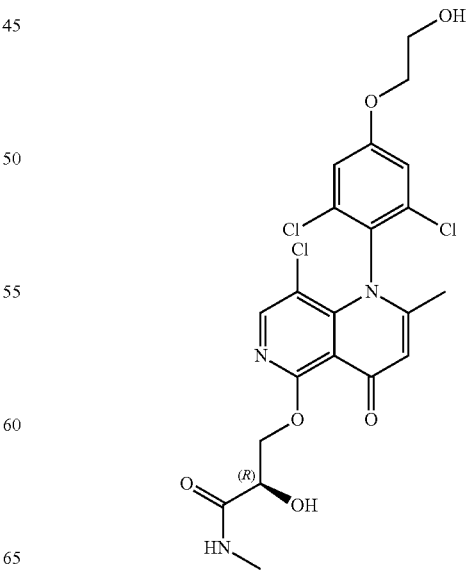

0.01 g (off white powder, yield: 10%) of Example 12 was prepared in an analogous way to Example 13 using O-benzyl-D-serine instead of O-benzyl-L-serine. C-12: ESI-MS m/z: 515.9 [M+H]+ (Rt=1.36 min, LC-method-6). ¹H NMR (300 MHz, METHANOL-d4) δ ppm=8.51 (bs, 1H), 8.19 (s, 1H), 7.25 (s, 2H), 6.53 (s, 1H), 4.64-4.57 (m, 2H), 4.49 (t, J=4.8 Hz, 1H), 4.17-4.14 (t, J=4.4 Hz, 2H), 3.90 (t, J=4.8 Hz, 2H), 2.79 (s, 3H), 2.02 (s, 3H). Chiral HPLC (Rt=6.50 min, Chiral HPLC method 1): 99.0%.

Example 13: (S)-3-((8-Chloro-1-(2,6-dichloro-4-(2-hydroxyethoxy)phenyl)-2-methyl-4-oxo-1,4-dihydro-1,6-naphthyridin-5-yl)oxy)-2-hydroxy-N-methylpropanamide (Compound C-13)

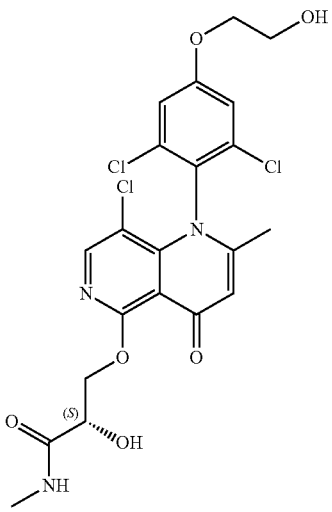

Step 1: (S)-3-(Benzyloxy)-2-hydroxypropanoic acid

To a solution of O-benzyl-L-serine (10.0 g 51.23 mmol) in 1.0 M H₂SO₄ (123 mL) at 0° C. was added 0.5 M NaNO₂ in water (300 mL; 290.98 mmol) dropwise for 1 h at 0° C. The solution so obtained was slowly warmed to ambient temperature for 20 h. The reaction mixture was basified to pH 6-7 using 1.0 M NaOH in water and washed with EtOAc. The aqueous layer was acidified to pH 2 using 1.0 M H₂SO₄ and extracted with EtOAc. The combined organic phases were washed with brine, dried over anhydrous Na₂SO₄, and concentrated under reduced pressure to get the product as a pale yellow oil (9.71 g, yield: 97%). ¹H NMR (400 MHz, CHLOROFORM-d3) δ ppm=7.36-7.26 (m, 5H), 4.59 (dd, 2H, J=2.8 Hz, 14.8 Hz), 4.38 (t, J=3.6 Hz, 1H), 3.83-3.76 (m, 2H).

Step 2: Methyl (S)-3-(benzyloxy)-2-hydroxypropanoate

To (S)-3-(benzyloxy)-2-hydroxypropanoic acid (9.7 g, 49.43 mmol) in methanol (50 mL) at 0° C. was dropwise added SOCl₂ (0.72 mL, 9.88 mmol) for 5 minutes at 0° C. The reaction mixture so obtained was stirred at ambient temperature for 1 h. To this reaction mixture was added trimethyl orthoformate (10.81 mL, 98.86 mmol). The resulting reaction mixture was stirred at ambient temperature for 20 h. The volatiles were evaporated under reduced pressure to get the crude product. The crude product was purified by Combi-Flash column chromatography using 80 g Silicycle cartridge and 0-20% EtOAc in hexane to get the desired product as a colorless oil (8.58 g yield: 83%). ESI-MS m/z: 211.10 [M+H]+, (Rt=1.09 min, LC-method 3). ¹H NMR (400 MHz, CHLOROFORM-d3) δ ppm=7.36-7.26 (m, 5H), 4.61 (d, 1H, J=12.0 Hz), 4.53 (d, J=12.4 Hz, 1H), 4.34-4.31 (m, 1H), 3.78 (s, 3H), 3.75 (d, J=3.6 Hz, 2H), 3.15 (d, J=6.8 Hz, 1H).

Step 3: Methyl (S)-3-(benzyloxy)-2-((tert-butyldimethylsilyl)oxy)propanoate

To a stirred solution of methyl (S)-3-(benzyloxy)-2-hydroxypropanoate (8.5 g 40.41 mmol) in dichloromethane (120 mL) at 0° C. was added DMAP (0.99 g; 8.08 mmol), imidazole (3.05 g, 44.85 mmol). The solution so obtained was stirred at 0° C. for 15 min. To this solution was added TBSCl (6.76 g, 44.86 mmol) and stirred at ambient temperature for 44 h. The reaction mixture was diluted with dichloromethane and washed with brine. The organic layer was dried over anhydrous sodium sulphate and evaporated under reduced pressure to get the crude product. The crude product was purified by Combi-Flash column chromatography using 80 g Silicycle cartridge and 0-20% EtOAc in hexane to get the desired product as a colorless oil (12.4 g, yield: 95%). ¹H NMR (300 MHz, CHLOROFORM-d3) δ ppm=7.31-7.26 (m, 5H), 4.58 (d, J=2.1 Hz, 2H), 4.41 (t, J=6.0 Hz, 1H), 3.73 (s, 3H), 3.66 (t, J=3.9 Hz, 2H), 0.91 (s, 9H), 0.10 (s, 3H), 0.08 (s, 3H).

Step 4: Methyl (S)-2-((tert-butyldimethylsilyl)oxy)-3-hydroxypropanoate

To a stirred solution of methyl (S)-3-(benzyloxy)-2-((tert-butyldimethylsilyl)oxy)-propanoate (6.0 g, 18.490 mmol) in dichloromethane (20 mL) was added 10% palladium on carbon (0.65 g). The reaction mixture so obtained was stirred under hydrogen atmosphere (1 atmospheric pressure) for 16 h. The reaction mixture was filtered through a pad of Celite and rinsed with dichloromethane. The filtrate was evaporated under reduced pressure to get the crude product. The crude material was purified by Combi-Flash using 40 g Silicycle cartridge and 0-30% EtOAc in hexane to get the title product as a colorless oil (2.57 g, yield: 59%). ¹H NMR (300 MHz, CHLOROFORM-d3) δ ppm=4.29 (t, J=4.5 Hz, 1H), 3.79 (d, J=4.5 Hz, 2H), 3.74 (s, 3H), 2.22 (t, J=6.6 Hz, 1H), 0.90 (s, 9H), 0.13 (s, 3H), 0.08 (s, 3H).

Step 5: (S)-3-((tert-Butyldimethylsilyl)oxy)-2-hydroxy-N-methylpropanamide

To a solution of methyl (S)-2-((tert-butyldimethylsilyl)oxy)-3-hydroxypropanoate (2.5 g, 10.66 mmol) in MeOH (5 mL) was added 40% methylamine in methanol (61.5 mL, 160.00 mmol). The resulting reaction mixture was stirred at 85° C. for 12 h. The volatiles were evaporated under high vacuum to get the title product (2.2 g, crude). Note: During amide formation migration of the silyl group occurred to yield the product indicated in the title. ESI-MS m/z: 233.75 (M+H)+, (Rt=1.454 min, LC-method 6). ¹H NMR (300 MHz, CHLOROFORM-d3) δ ppm=4.15 (d, 1H), 4.07 (t, 1H), 3.81-3.65 (m, 1H), 2.94-2.82 (m, 3H), 0.88 (s, 9H), 0.07 (s, 6H).

Step 6: (S)-3-((tert-Butyldimethylsilyl)oxy)-2-((8-chloro-1-(2,6-dichloro-4-fluorophenyl)-2-methyl-4-oxo-1,4-dihydro-1,6-naphthyridin-5-yl)oxy)-N-methylpropanamide To a solution of 5,8-dichloro-1-(2,6-dichloro-4-fluorophenyl)-2-methyl-1,6-naphthyridin-4(1H)-one (intermediate F1, 1.0 g, 2.55 mmol) and (S)-3-((tert-butyldimethylsilyl)oxy)-2-hydroxy-N-methylpropanamide (0.72 g, 3.06 mmol) in acetonitrile (10 mL) was added potassium carbonate (0.88 g, 6.38 mmol), DMAP (0.06 g, 0.51 mmol). The resulting reaction mixture was stirred at 80° C. for 16 h. The reaction mixture was diluted with water and extracted with EtOAC. The combined organic phases were washed with water, brine, dried over $Na_2SO_4$ and evaporated under reduced pressure to yield the crude product. The crude product was purified by MPLC (Combi-Flash, 40 g Rediff column and 20-100% ethyl acetate in hexane to get the title product as a pale brown semi-solid solid (0.52 g, yield: 35%). ESI-MS m/z: 588.05 (M+H)$^+$, (Rt=1.74 min, LC-method 5). $^1$H NMR (300 MHz, CHLOROFORM-d3) δ ppm=9.13 (s, 1H), 8.06 (s, 1H), 7.28 (s, 2H), 6.43 (s, 1H), 5.65 (t, J=2.7 Hz, 1H), 4.25 (d, J=2.7 Hz, 2H), 2.93 (d, J=4.5 Hz. 3H), 2.04 (s, 3H), 0.81 (s, 9H), −0.05 (d, J=5.7 Hz, 6H).

Step 7: (S)-3-((tert-Butyldimethylsilyl)oxy)-2-((8-chloro-1-(2,6-dichloro-4-(2-hydroxy ethoxy) phenyl)-2-methyl-4-oxo-1,4-dihydro-1,6-naphthyridin-5-yl)oxy)-N-methylpropanamide To a solution of (S)-3-((tert-butyldimethylsilyl)oxy)-2-((8-chloro-1-(2,6-dichloro-4-fluorophenyl)-2-methyl-4-oxo-1,4-dihydro-1,6-naphthyridin-5-yl)oxy)-N-methylpropanamide (0.4 g, 0.68 mmol) and ethylene glycol (0.06 g, 1.02 mmol) in acetonitrile (6 mL) in a screw capped microwave vial was added cesium carbonate (0.44 g, 1.36 mmol). The resulting reaction mixture was stirred at 80° C. in an Anton Parr microwave reactor for 30 min. (Note: This reaction was performed in 4×0.1 g batches). The combined reaction mixtures were diluted with water and extracted with EtOAC. The combined organic phases were washed with water, brine, dried over $Na_2SO_4$ and evaporated under reduced pressure to yield the crude product. The crude product was purified by MPLC using 24 g Redisep column and 20-100% ethyl acetate in hexane to get the title product as a pale yellow semi-solid (0.15 g, yield: 20%). ESI-MS m/z: 630.2 (M+H)$^+$, (Rt=1.591 min, LC-method 5). $^1$H NMR (400 MHz, CHLOROFORM-d3) δ ppm=9.21 (d, 1H), 8.06 (s, 1H), 7.03 (s, 2H), 6.43 (s, 1H), 5.65 (t, 1H, J=2.1 Hz), 4.17 (t, 2H, J=4 Hz), 4.05-4.02 (m, 2H), 3.74 (s, 2H), 2.93 (d, 3H, J=4.84 Hz), 2.10 (d, 1H, J=6 Hz), 1.97 (s, 3H), 0.81 (s, 9H), −0.04 (m, 6H).

Step 8: (S)-3-((8-Chloro-1-(2,6-dichloro-4-(2-hydroxyethoxy)phenyl)-2-methyl-4-oxo-1,4-dihydro-1,6-naphthyridin-5-yl)oxy)-2-hydroxy-N-methylpropanamide To a solution of ((S)-3-((tert-butyldimethylsilyl)oxy)-2-((8-chloro-1-(2,6-dichloro-4-(2-hydroxyethoxy)phenyl)-2-methyl-4-oxo-1,4-dihydro-1,6-naphthyridin-5-yl)oxy)-N-methyl propanamide (0.15 g, 0.24 mmol) in THF (4 mL) at 0° C. was added 1.0 M TBAF in THF (0.36 mL, 0.36 mmol). The reaction mixture so obtained was stirred at ambient temperature for 1 h. The reaction mixture was quenched with ice cold water and extracted with EtOAC. The combined organic phases were washed with water, brine, dried over $Na_2SO_4$ and evaporated under reduced pressure to yield the crude product. The crude product was purified by Combi-Flash using 12 g Redisep silica-gel column and 0-1.5% MeOH in dichloromethane and further purified by Combi-Flash using 12 g Redisep silica-gel column and 0-2% MeOH in dichloromethane to get pure desired product as an off white solid (0.038 g, yield: 31%). Note: During deprotection of the silyl group rearrangement of the ether to the title compound occurred. C-13: HRMS m/z: calc. 516.0496 [M+H]$^+$, found 516.0592. ESI-MS m/z: 515.9 [M+H]$^+$ (Rt=1.35 min, LC-method 6); $^1$H NMR (300 MHz, METHANOL-d4) δ ppm=8.19 (s, 1H), 7.26 (s, 2H), 6.52 (s, 1H), 4.63-4.55 (m, 2H), 4.49-4.47 (m, 1H), 4.18 (t, J=4.2 Hz, 2H), 3.91 (t, J=4.5 Hz, 2H), 2.81 (s, 3H), 2.03 (s, 3H). Chiral HPLC (Rt=4.80 min, Chiral HPLC method 1): 97.9%.

Example 14: (S)-3-((8-chloro-1-(2,6-dichloro-4-(2-hydroxy-2-methylpropoxy)phenyl)-2-methyl-4-oxo-1,4-dihydro-1,6-naphthyridin-5-yl)oxy)-2-hydroxy-N-methylpropanamide (Compound C-14)

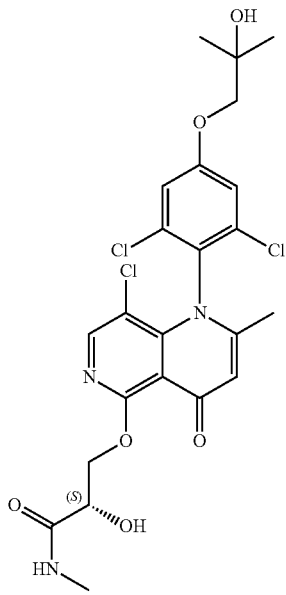

To a solution of (S)-3-((tert-butyldimethylsilyl)oxy)-2-((8-chloro-1-(2,6-dichloro-4-fluorophenyl)-2-methyl-4-oxo-1,4-dihydro-1,6-naphthyridin-5-yl)oxy)-N-methylpropanamide [step-6 of Example 13]$^+$ (0.5 g, 0.85 mmol) and 2-methylpropane-1,2-diol (0.15 g, 1.7 mmol) in DMF (5 mL) was added cesium carbonate (0.83 g, 2.55 mmol). The resulting reaction mixture was stirred at ambient temperature for 2 h. The reaction mixture was diluted with water and extracted with EtOAC. The combined organic phases were washed with water, brine, dried over $Na_2SO_4$ and evaporated under reduced pressure to yield the crude product. The crude product was purified by Combi-Flash using 12 g Redisep silica-gel column and 0-2% MeOH in dichloromethane and preparative HPLC (column: ATLANTIS-T3 (250 mm×19 mm, 5.0 μm); mobile phase: 0.1% HCOOH in water and acetonitrile; gradient elution) to get the desired product as off white solid (0.003 g, yield: 3%). C-14: ESI-MS m/z: 544.10 [M+H]$^+$ (Rt=1.10 min, LC-method 3); $^1$H NMR (300 MHz, METHANOL-d4) δ ppm=8.19 (s, 1H), 7.27 (s, 2H), 6.52 (s, 1H), 4.63-4.59 (m, 2H), 4.49-4.47 (m, 1H), 3.91 (s, 2H), 2.81 (s, 3H), 2.03 (s, 3H), 1.33 (s, 6H). Chiral HPLC (Rt=8.04 min, Chiral HPLC method 2): 98.6%.

Example 15: 3-((8-Chloro-1-(2,6-dichloro-4-((3-hydroxyoxetan-3-yl)methoxy)phenyl)-2-methyl-4-oxo-1,4-dihydro-1,6-naphthyridin-5-yl)oxy)-N-methylpropanamide (Compound C-15)

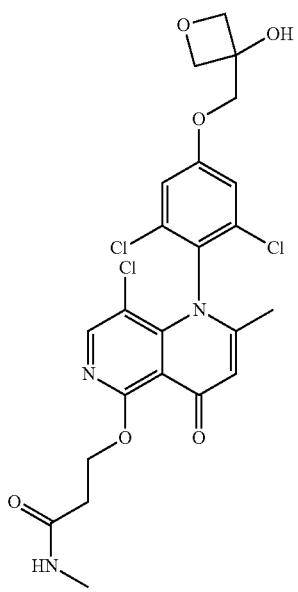 [SMILES: CNC(=O)CCOc1ncc(Cl)c2c1c(=O)cc(C)n2-c1c(Cl)cc(OCC2(O)COC2)cc1Cl]

Step 1: 3-(Hydroxymethyl)oxetan-3-ol

To a solution of 3-methyleneoxetane (500 mg, 7.13 mmol) in THF (1.0 mL) and H$_2$O (1.0 mL) at 0° C. was sequentially added osmium tetraoxide (4%) (0.1 mL, 7.13 mmol) and H$_2$O$_2$(50%) (1.0 mL, 16.32 mmol). The mixture was allowed to come to room temperature and stirred for 1 hr. Then it was diluted with 3 mL water and filtered through a pad of Celite. The filtrate was concentrated on a rotovap at 42° C. and 50 mbar for 30 min to give the title compound. $^1$H NMR (400 MHz, METHANOL-d4) δ ppm=4.63-4.48 (m, 4H), 3.70 (s, 2H).

Step 2: 3-((8-Chloro-1-(2,6-dichloro-4-fluorophenyl)-2-methyl-4-oxo-1,4-dihydro-1,6-naphthyridin-5-yl)oxy)-N-methylpropanamide To a solution of 5,8-dichloro-1-(2,6-dichloro-4-fluorophenyl)-2-methyl-1,6-naphthyridin-4(1H)-one (intermediate F1, 1500 mg, 3.826 mmol) and 3-hydroxy-N-methylpropanamide (512.9 mg, 4.974 mmol) in CH$_3$CN (50 mL) was added DMAP (233.7 mg, 1.913 mmol) and K$_2$CO$_3$ (1586 mg, 11.48 mmol). The mixture was stirred at 80° C. for 16 hours. Then it was allowed to cool to room temperature and filtered and washed with MeOH. The filtrate was concentrated to dry. The residue was purified by flash column 0-10% MeOH/DCM to provide the title compound. ESI-MS m/z: 458.1 [M+H]$^+$ (Rt=0.93 min, LC-method 7).

Step 3: 3-((8-Chloro-1-(2,6-dichloro-4-((3-hydroxyoxetan-3-yl)methoxy)phenyl)-2-methyl-4-oxo-1,4-dihydro-1,6-naphthyridin-5-yl)oxy)-N-methylpropanamide To a solution of 3-((8-chloro-1-(2,6-dichloro-4-fluorophenyl)-2-methyl-4-oxo-1,4-dihydro-1,6-naphthyridin-5-yl)oxy)-N-methylpropanamide (300 mg, 0.654 mmol) and 3-(hydroxymethyl) oxetan-3-ol (204 mg, 1.96 mmol) in DMF (6 mL) was added Cs$_2$CO$_3$ (1.07 g, 3.27 mmol). The mixture was stirred at 40° C. for 24 hours. Then it was allowed to cool down to room temperature, diluted in MeOH and filtered. The filtrate was purified by HPLC to give title compound. C-15: ESI-MS m/z: 541.9 [M+H]V (Rt=0.93 min, LC-method 7), $^1$H NMR (400 MHz, METHANOL-d4) δ ppm=8.20 (s, 1H), 7.33 (s, 2H), 6.52 (s, 1H), 4.71-4.59 (m, 6H), 4.33 (s, 2H), 2.79 (s, 3H), 2.75 (t, J=5.9 Hz, 2H), 2.04 (s, 3H).

Example 16: 3-((8-Chloro-1-(2,6-dichloro-4-(2-hydroxyethoxy)phenyl)-2-methyl-4-oxo-1,4-dihydro-1,6-naphthyridin-5-yl)oxy)-2,2-difluoro-N-methylpropanamide (Compound C-16)

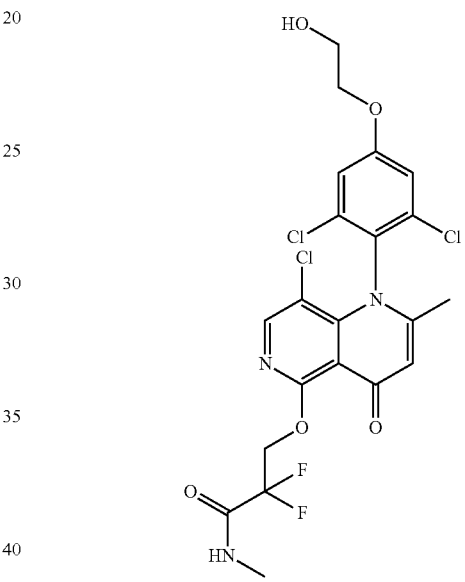

Step 1: 2,2-Difluoro-3-hydroxy-N-methylpropanamide

To a solution of ethyl 2,2-difluoro-3-hydroxypropanoate (0.2 g, 0.65 mmol) in MeOH (1.0 mL) in a screw capped sealed tube was added 40% methylamine in methanol (2.0 mL). The reaction mixture was stirred at 80° C. for 16 h. The volatiles were evaporated under reduced pressure to get the crude product (0.12 g, yield: 40%). $^1$H NMR (300 MHz, METHANOL-d4D) δ ppm=6.49 (bs, 1H), 4.06-3.97 (m, 2H), 2.93 (s, 3H).

Step 2: 3-((8-Chloro-1-(2,6-dichloro-4-fluorophenyl)-2-methyl-4-oxo-1,4-dihydro-1,6-naphthyridin-5-yl)oxy)-2,2-difluoro-N-methylpropanamide To a solution of 5,8-dichloro-1-(2,6-dichloro-4-fluorophenyl)-2-methyl-1,6-naphthyridin-4(1H)-one (intermediate F1, 0.35 g, 0.88 mmol) and 2,2-difluoro-3-hydroxy-N-methylpropanamide (0.11 g, 0.79 mmol) in acetonitrile (5 mL) was added K$_2$CO$_3$ (0.3 g, 2.19 mmol) and DMAP (0.03 g, 0.26 mmol). The resulting reaction mixture was stirred at 80° C. for 16 h. The reaction mixture was poured into water and extracted with EtOAc. The combined organic layers were washed with brine, dried over anhydrous Na$_2$SO$_4$ and concentrated under reduced pressure to get the crude product. The crude product was purified by MPLC using 24 g Silicycle column cartridge and 40-70% EtOAc in hexane to get the title product as an off-white solid (0.2 g, yield: 37%). ESI-MS m/z: 493.8 [M+H]$^+$ (Rt=1.08 min, LC-method 6).

Step 3: 3-((8-Chloro-1-(2,6-dichloro-4-(2-hydroxyethoxy)phenyl)-2-methyl-4-oxo-1,4-dihydro-1,6-naphthyridin-5-yl)oxy)-2,2-difluoro-N-methylpropanamide To a solution of 3-((8-chloro-1-(2,6-dichloro-4-fluorophenyl)-2-methyl-4-oxo-1,4-dihydro-1,6-naphthyridin-5-yl)oxy)-2,2-difluoro-N-methylpropanamide (0.06 g, 0.12 mmol) in DMF (3 mL) in a microwave vial was added K$_2$CO$_3$ (0.04 g, 0.30 mmol) and ethylene glycol (0.01 g, 0.18 mmol). The resulting reaction mixture was stirred at 80° C. in an Anton Parr microwave reactor for 3 h. The reaction mixture was poured into water and extracted with EtOAc. The combined organic layers were washed with brine, dried over anhydrous Na$_2$SO$_4$ and concentrated under reduced pressure to get the crude product. The crude product was purified twice by MPLC using 24 g Redisep cartridge and 5-10% methanol in dichloromethane to get the title product as off-white solid (0.008 g, yield: 15%). C-16: ESI-MS m/z: 536.05 [M+H]$^+$ (Rt=0.83 min, LC-method-3). $^1$H NMR (400 MHz, METHANOL-d4) δ ppm=8.22 (s, 1H), 7.27 (s, 2H), 6.52 (s, 1H), 4.87-4.81 (m, 2H), 4.18 (t, J=4.4 Hz, 2H), 3.92 (t, J=4.8 Hz, 2H), 2.88 (s, 3H), 2.04 (s, 3H).

Example 17: 2-(4-(5-(2-Amino-2-oxoethoxy)-8-chloro-2-methyl-4-oxo-1,6-naphthyridin-1(4H)-yl)-3,5-dichlorophenoxy)-N-methylacetamide (Compound C-17)

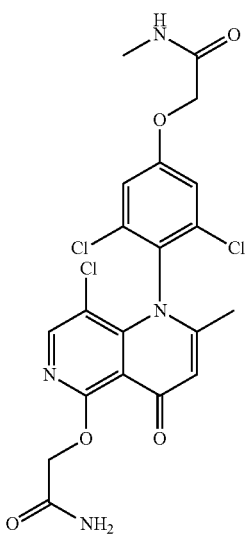 [SMILES: CNC(=O)COc1cc(Cl)c(-n2c(C)cc(=O)c3c(OCC(N)=O)ncc(Cl)c32)c(Cl)c1]

Step 1: 2-((1-(4-Bromo-2,6-dichlorophenyl)-8-chloro-2-methyl-4-oxo-1,4-dihydro-1,6-naphthyridin-5-yl)oxy)acetamide To a solution of 1-(4-bromo-2,6-dichlorophenyl)-5,8-dichloro-2-methyl-1,6-naphthyridin-4(1H)-one (intermediate F2, 5.0 g, 11.06 mmol), K$_2$CO$_3$ (4.57 g, 33.18 mmol) in acetonitrile (50 mL) in a screw capped sealed tube was added 2-hydroxyacetamide (0.83 g, 11.06 mmol) and DMAP (0.67 g, 5.53 mmol). The contents of the sealed tube were stirred at 75° C. 24 h. The reaction mixture was filtered off and rinsed with CH$_3$CN. The organic layer was concentrated in vacuo. The residue was purified by MPLC using 40 g Redisep column and 20-100% EtOAc in hexane to get the title product as an off white solid (4.5 g, yield: 83%). ESI-MS m/z: 489.85 [M+H]$^+$ (Rt=1.48 min, LC-method 6).

Step 2: (4-(5-(2-Amino-2-oxoethoxy)-8-chloro-2-methyl-4-oxo-1,6-naphthyridin-1(4H)-yl)-3,5-dichlorophenyl)boronic acid To a degassed (with argon) solution of 2-((1-(4-bromo-2,6-dichlorophenyl)-8-chloro-2-methyl-4-oxo-1,4-dihydro-1,6-naphthyridin-5-yl)oxy)acetamide(4.0 g, 8.14 mmol), bis(pinacolato)diboron (3.09 g, 12.21 mmol), and potassium acetate (1.19 g, 12.21 mmol) in 1,4-dioxane (40 mL) in a screw capped sealed tube was added PdCl$_2$dppf·DCM (0.66 g, 0.81 mmol). The contents of the sealed tube were stirred at 90° C. for 4 h. The reaction mixture was filtered through a pad of Celite and rinsed with 1,4-dioxane. The filtrate was evaporated under reduced pressure to get the crude product as light brown solid (4.2 g, crude). Thus, obtained crude product was used in the next step without further purification. ESI-MS m/z: 456.0 [M+H]$^+$ (Rt=1.38 min, LC-method 1).

Step 3: 2-((8-Chloro-1-(2,6-dichloro-4-hydroxyphenyl)-2-methyl-4-oxo-1,4-dihydro-1,6-naphthyridin-5-yl)oxy)acetamide To a solution of 4-(5-(2-amino-2-oxoethoxy)-8-chloro-2-methyl-4-oxo-1,6-naphthyridin-1(4H)-yl)-3,5-dichlorophenyl)boronic acid (2.5 g, 5.48 mmol) in MeOH: water (20 mL, 1:1) was added Montmorilite K-10 (2.25 g, 8.22 mmol) and 30% hydrogen peroxide (100 mL). The resulting reaction mixture was stirred at ambient temperature for 4 h. The reaction mixture was quenched with excess of ice water and extracted with EtOAc. The combined organic layers were washed brine, dried over anhydrous sodium sulphate, and concentrated under reduced pressure to get the crude product. The crude product was purified by Combi-Flash column chromatography using 24 g Silicycle cartridge and 20-100 ethyl acetate in hexane to get the title product as off-white solid (1.3 g, yield: 55%). ESI-MS m/z: 429.9 [M+H]$^+$ (Rt=1.41 min, LC-method 1).

Step 4: 2-(4-(5-(2-Amino-2-oxoethoxy)-8-chloro-2-methyl-4-oxo-1,6-naphthyridin-1(4H)-yl)-3,5-dichlorophenoxy)-N-methylacetamide To a solution of 2-((8-chloro-1-(2,6-dichloro-4-hydroxyphenyl)-2-methyl-4-oxo-1,4-dihydro-1,6-naphthyridin-5-yl)oxy)acetamide (0.1 g, 0.23 mmol) in DMF (4 mL) was added potassium carbonate (0.96 g, 0.7 mmol) and 2-bromo-N-methylacetamide (0.05 g, 0.35 mmol). The reaction mixture was stirred at room temperature for 4 h. The reaction mixture was diluted with water and extracted with EtOAc. The combined organic layers were washed with brine, dried over anhydrous sodium sulfate and concentrated under reduced pressure to get the crude product. The crude product was purified by Combi-Flash column chromatography using 12 g Redisep column and 70-100% EtOAc in hexane to get the title product as an off-white solid (0.035 g, yield: 38%). C-17: ESI-MS m/z: 499.0 [M+H]$^+$ (Rt=1.37 min, LCmethod-1). $^1$H NMR (300 MHz, DMSO-d$_6$) δ ppm=8.27 (s, 1H), 8.13 (m, 2H), 7.60 (s, 1H), 7.41 (s, 2H), 6.55 (s, 1H), 4.74 (s, 2H), 4.66 (s, 2H), 2.68 (d, J=4.8 Hz, 3H), 1.94 (s, 3H).

Example 18: 3-((8-Chloro-1-(2,6-dichloro-4-(2-hydroxyethoxy)phenyl)-2-methyl-4-oxo-1,4-dihydro-1,6-naphthyridin-5-yl)oxy)propenamide (Compound C-18)

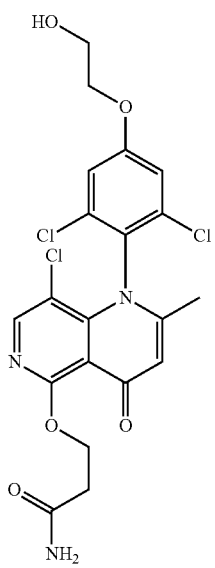 [SMILES: Cc1cc(=O)c2c(OCCC(N)=O)ncc(Cl)c2n1-c1c(Cl)cc(OCCO)cc1Cl]

To a solution of 250 mg (0.565 mmol) of 3-((8-chloro-1-(2,6-dichloro-4-hydroxyphenyl)-2-methyl-4-oxo-1,4-dihydro-1,6-naphthyridin-5-yl)oxy)propenamide [prepared in an analogous way to step-1 to step-3 of Example 17 using 3-hydroxypropanamide instead of 2-hydroxacetamide] in DMF (5 mL) was added silver carbonate (0.46 g, 1.69 mmol) and 2-bromoethanol (0.14 g, 1.13 mmol). The reaction mixture was stirred at 80° C. for 16 h. The reaction mixture was diluted with water and extracted with EtOAc. The combined organic layers were washed with brine wash, dried over anhydrous sodium sulfate and concentrated under reduced pressure to get the crude product. The crude product was purified by Combi-Flash column chromatography using 12 g Redisep column and 20-100% EtOAc in hexane and subsequent preparative HPLC (column: GEMINI 250 mm×21.2 mm, 5.0 μm); mobile phase: 0.02% NH$_4$OH in water and acetonitrile, gradient elution) to get the title product as an off-white solid (0.022 g, yield: 8%). C-18: ESI-MS m/z: 487.35 [M+1]$^+$ (Rt=1.38 min, LC-method-1). $^1$H NMR (300 MHz, DMSO-d$_6$) δ ppm=8.23 (s, 1H), 7.70 (s, 1H), 7.34 (s, 2H), 6.94 (s, 1H), 6.43 (s, 1H), 4.52 (t, J=6.0 Hz, 2H), 4.14 (t, J=3.9 Hz, 2H), 3.74 (t, J=4.8 Hz, 2H), 2.58 (t, J=6.0 Hz, 3H), 1.89 (s, 3H).

Example 19: N-(3-(8-Chloro-1-(2,6-dichloro-4-(2-hydroxyethoxy)phenyl)-2-methyl-4-oxo-1,4-dihydro-1,6-naphthyridin-5-yl)propyl)acetamide (Compound C-19)

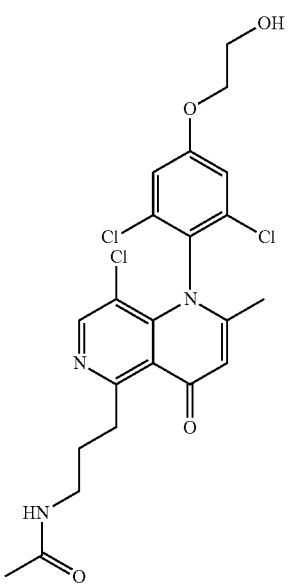 [SMILES: CC(=O)NCCCc1ncc(Cl)c2c1c(=O)cc(C)n2-c1c(Cl)cc(OCCO)cc1Cl]

Step 1: tert-Butyl (3-(8-chloro-1-(2,6-dichloro-4-fluorophenyl)-2-methyl-4-oxo-1,4-dihydro-1,6-naphthyridin-5-yl)propyl)carbamate To a sealed vial charged with tert-butyl allylcarbamate (241 mg, 1.53 mmol) in 3 mL THF under N$_2$ was added (1s,5s)-9-borabicyclo[3.3.1]nonane (0.5M in THF) (3.32 mL, 1.66 mmol) dropwise. The mixture was stirred at room temperature for 16 hours. To a flask charged with 5,8-dichloro-1-(2,6-dichloro-4-fluorophenyl)-2-methyl-1,6-naphthyridin-4(1H)-one (intermediate F1, 500 mg, 1.28 mmol), Pd(Ph$_3$P)$_4$ (147 mg, 128 μmol) and potassium phosphate (2.0M solution) (1.28 mL, 2.55 mmol) in DMF (10.0 mL) under N$_2$ was added above solution by syringe. The reaction mixture was heated at 80° C. under N$_2$ for 2 hours. Then it was cooled down to room temperature, diluted with EtOAc and washed with water. The aq. layer was extracted with EtOAc. Combined organic layer was concentrated under reduced pressure. The residue was purified by flash column EtOAc/Heptane 0-100% to provide title compound. ESI-MS m/z: 514.3 [M+H]$^+$ (Rt=1.20 min, LC-method 7).

Step 2: 5-(3-Aminopropyl)-8-chloro-1-(2,6-dichloro-4-fluorophenyl)-2-methyl-1,6-naphthyridin-4(1H)-one hydrochloride To a solution of tert-butyl (3-(8-chloro-1-(2,6-dichloro-4-fluorophenyl)-2-methyl-4-oxo-1,4-dihydro-1,6-naphthyridin-5-yl)propyl)carbamate (582 mg, 1.13 mmol) in dioxane (3 mL) was added HCl (4M in dioxane) (2.83 mL, 11.3 mmol). The mixture was stirred at 23° C. for 2 hours. Concentrated under reduced pressure and the residue was dried under high vacuum to provide title compound. ESI-MS m/z: 414.2 [M+H]$^+$ (Rt=0.77 min, LC-method 7).

Step 3: N-(3-(8-Chloro-1-(2,6-dichloro-4-fluorophenyl)-2-methyl-4-oxo-1,4-dihydro-1,6-naphthyridin-5-yl)propyl)acetamide To a solution of 5-(3-aminopropyl)-8-chloro-1-(2,6-dichloro-4-fluorophenyl)-2-methyl-1,6-naphthyridin-4(1H)-one hydrochloride (490 mg, 1.00 mmol) and acetic acid (302 mg, 5.02 mmol) in DMF (10 mL) was added TEA (712 mg, 7.03 mmol) and HATU (497 mg, 1.31 mmol). The mixture was stirred at 23° C. for 1 hour. Diluted in MeOH and filtered. The filtrate was purified by HPLC to give title compound. ESI-MS m/z: 456.2 [M+H]$^+$ (Rt=0.91 min, LC-method 7).

Step 4: N-(3-(8-Chloro-1-(2,6-dichloro-4-(2-hydroxyethoxy)phenyl)-2-methyl-4-oxo-1,4-dihydro-1,6-naphthyridin-5-yl)propyl)acetamide To a solution of N-(3-(8-chloro-1-(2,6-dichloro-4-fluorophenyl)-2-methyl-4-oxo-1,4-dihydro-1,6-naphthyridin-5-yl)propyl)acetamide (200 mg, 0.44 mmol) and ethane-1,2-diol (81.5 mg, 1.31 mmol) in DMF (6 mL) was added Cs$_2$CO$_3$ (428 mg, 1.31 mmol). The mixture was stirred at 23° C. for 16 hour. It was diluted in MeOH and filtered. The filtrate was purified by HPLC to give the title compound. C-19: ESI-MS m/z: 498.1 [M+H]$^+$ (Rt=0.79 min, LC-method 7), $^1$H NMR (400 MHz, METHANOL-d4) δ ppm=8.49 (s, 1H), 7.29 (s, 2H), 6.54 (s, 1H), 4.26-4.15 (m, 2H), 3.99-3.87 (m, 2H), 3.57-3.44 (m, 2H), 2.07 (s, 3H), 1.98 (s, 3H), 1.97-1.90 (m, 2H), 2H overlap with solvent.

Example 20: 8-Chloro-1-(2,6-dichloro-4-(2-hydroxyethoxy)phenyl)-2-methyl-5-(2-(methylsulfonyl)ethyl)-1,6-naphthyridin-4(1H)-one (Compound C-20)

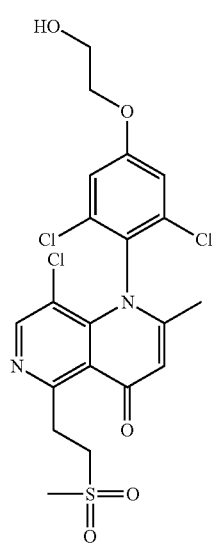 [SMILES: Cc1cc(=O)c2c(CCS(C)(=O)=O)ncc(Cl)c2n1-c1c(Cl)cc(OCCO)cc1Cl]

Step 1: 8-Chloro-1-(2,6-dichloro-4-fluorophenyl)-2-methyl-5-vinyl-1,6-naphthyridin-4(1H)-one To a stirred solution of 5,8-dichloro-1-(2,6-dichloro-4-fluorophenyl)-2-methyl-1,6-naphthyridin-4(1H)-one (intermediate F1, 0.4 g, 1.02 mmol) in THF (10 mL) was added tributyl(vinyl)stannane (0.39 g, 1.22 mmol) and then purged with N$_2$ gas. To this solution was added tri-2-furylphosphine (0.02 g, 0.1 mmol) and Pd$_2$(dba)$_3$ (0.09 g, 0.1 mmol). The reaction mixture was stirred at 70° C. for 16 h. The reaction mixture was diluted with water and extracted with EtOAc. The combined organic phases were washed with brine, dried over Na$_2$SO$_4$ and the solvent was removed under reduced pressure to get the crude product. The crude product was purified by MPLC (Combi-Flash, 24 g column, Gradient Elusion, 0-40% EtOAc in hexane) to obtain the title product as a pale yellow solid (0.21 g, yield: 54%). ESI-MS m/z: 384.40 [M+3H]$^+$ (Rt=1.54 min, LC-method 1).

Step 2: 8-Chloro-1-(2,6-dichloro-4-(2-hydroxyethoxy)phenyl)-2-methyl-5-vinyl-1,6-naphthyridin-4(1H)-one To a solution of 8-chloro-1-(2,6-dichloro-4-fluorophenyl)-2-methyl-5-vinyl-1,6-naphthyridin-4(1H)-one (0.2 g, 0.521 mmol) in DMF (3 mL) was added ethylene glycol (0.04 g, 0.63 mmol), and K$_2$CO$_3$ (0.22 g, 1.56 mmol). The reaction mixture was stirred at 80° C. for 16 h. The reaction mixture was diluted with water and EtOAc and extracted with EtOAc The combined organic phases were washed brine, dried over Na$_2$SO$_4$ and the solvent was removed under reduced pressure to get the crude product. The crude product was purified by MPLC (Combi-Flash, 12 g column, gradient elution, 0-10% MeOH in dichloromethane) to obtain the desired product as a pale yellow solid (0.1 g, yield: 48%). ESI-MS m/z: 424.90 [M+1H]$^+$ (Rt=1.45 min, LC-method 6).

Step 3: 8-Chloro-1-(2,6-dichloro-4-(2-hydroxyethoxy)phenyl)-2-methyl-5-(2-(methylsulfonyl)ethyl)-1,6-naphthyridin-4(1H)-one To a solution of 8-chloro-1-(2,6-dichloro-4-(2-hydroxyethoxy)phenyl)-2-methyl-5-vinyl-1,6-naphthyridin-4(1H)-one (0.08 g, 0.19 mmol) in ethanol (3 mL) was added sodium methane sulfinate (0.19 g, 1.89 mmol) and acetic acid (0.01 g, 0.19 mmol). The reaction mixture was stirred at 60° C. for 16 h. The reaction mixture was concentrated under reduced pressure to get the crude product. The crude product was purified by preparative HPLC (Column: X SELECT, 250 mm×19 mm, 5.0 µm), mobile phase: 0.02% NH$_4$OH in water, and acetonitrile; gradient elusion) to get the title product as off-white solid (0.04 g, yield: 56%). C-20: ESI-MS m/z: 504.95 [M+1H]$^+$ (Rt=1.38 min, LC-method-6). $^1$H NMR (300 MHz, DMSO-d$_6$) δ ppm=8.59 (s, 1H), 7.38 (s, 2H), 6.59 (s, 1H), 4.99 (t, J=5.4 Hz, 1H), 4.17 (t, J=4.8 Hz, 2H), 3.86-3.82 (m, 2H), 3.76 (m, 2H), 3.56-3.51 (m, 2H), 3.06 (s, 3H), 1.96 (s, 3H).

Example 21: 8-Chloro-1-(2,6-dichloro-4-(2-hydroxyethoxy)phenyl)-2-methyl-5-(2-(methyl sulfonyl)propyl)-1,6-naphthyridin-4(1H)-one (Compound C-21)

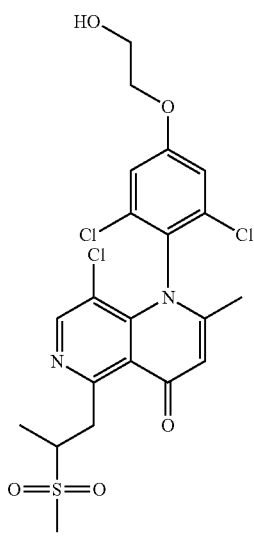 [SMILES: Cc1cc(=O)c2c(CC(C)S(C)(=O)=O)ncc(Cl)c2n1-c1c(Cl)cc(OCCO)cc1Cl]

Step 1: 5-Allyl-8-chloro-1-(2,6-dichloro-4-fluorophenyl)-2-methyl-1,6-naphthyridin-4(1H)-one To a stirred solution of 5,8-dichloro-1-(2,6-dichloro-4-fluorophenyl)-2-methyl-1,6-naphthyridin-4(1H)-one (intermediate F1, 0.05 g, 1.28 mmol) in THF (5 mL) was added tributyl(allyl)stannane (0.51 g, 1.53 mmol) and then purged with N$_2$ gas. To this solution was added tri-2-furylphosphine (0.03 g, 0.13 mmol) and Pd$_2$(dba)$_3$ (0.12 g, 0.13 mmol). The reaction mixture was stirred at 70° C. for 4 h. The reaction mixture was diluted with water and extracted with EtOAc. The organic phases were washed brine, dried over Na$_2$SO$_4$ and the solvent was removed under reduced pressure to get the crude product. The crude product was purified by MPLC (Combi-Flash, 12 g column, gradient elution, 20-100% EtOAc in hexane) to obtain the desired product as a pale yellow solid (0.27 g, yield: 53.25%). ESI-MS m/z: 397.0 [M+1H]$^+$ (Rt=1.77 min, LC-method 5).

Step 2: 5-Allyl-8-chloro-1-(2,6-dichloro-4-(2-hydroxyethoxy)phenyl)-2-methyl-1,6-naphthyridin-4(1H)-one To a solution of 5-allyl-8-chloro-1-(2,6-dichloro-4-fluorophenyl)-2-methyl-1,6-naphthyridin-4(1H)-one (0.25 g, 0.63 mmol) in DMF (3 mL) was added ethylene glycol (0.05 g, 0.75 mmol), and K$_2$CO$_3$ (0.26 g, 1.88 mmol). The reaction mixture was stirred at 80° C. for 16 h. The reaction mixture was diluted with water extracted with EtOAc. The combined organic phases were washed once with cold water, dried over Na$_2$SO$_4$ and the solvent was removed under reduced pressure to get crude product. The crude product was purified by MPLC (Combi-Flash, 12 g column gradient elution, 0-10% MeOH in dichloromethane) to obtain the desired product as an off-white solid (0.24 g, yield: 87%). ESI-MS m/z: 441.2 [M+3H]$^+$ (Rt=0.48 min, LC-method 4).

Step 3: 8-Chloro-1-(2,6-dichloro-4-(2-hydroxyethoxy)phenyl)-2-methyl-5-(2-(methylsulfonyl) propyl)-1,6-naphthyridin-4(1H)-one To a solution of 5-allyl-8-chloro-1-(2,6-dichloro-4-(2-hydroxyethoxy)phenyl)-2-methyl-1,6-naphthyridin-4(1H)-one (0.23 g, 0.52 mmol) in ethanol (8 mL) was added sodium methane sulfinate (0.53 g, 5.23 mmol), and acetic acid (0.03 g, 0.52 mmol). The reaction mixture was stirred at 60° C. for 16 h. The reaction mixture was concentrated under reduced pressure to get crude product. The crude product was purified by preparative HPLC (Column: Waters xbridge C18, 20 mm×150 mm, 5.0 μm); mobile phase: 0.02% NH$_4$OH in water and acetonitrile; gradient elution) to get the mixture of enantiomers as off-white solid (0.1 g, yield: 45%). The enantiomers were separated by preparative chiral HPLC [Column: LUX AMYLOSE-2, 250 mm×21.2 mm, 5.0 μm, hexane, and 0.1% formic acid in EtOH: MeOH (1:1); isocratic elution] to get the fast-eluting enantiomer as an off-white solid (0.03 g, yield: 22% based on single enantiomer). C-21: ESI-MS m/z: 519.1 [M+H]$^+$ (Rt=0.44 min, LC-method-4). $^1$H NMR (300 MHz, METHANOL-d4) δ ppm=8.54 (s, 1H), 7.28 (s, 2H), 6.55 (s, 1H), 4.31-4.25 (m, 1H), 4.19 (t, J=4.5 Hz, 2H), 3.92 (t, J=5.1 Hz, 2H), 3.86-3.82 (m, 1H), 3.56-3.48 (m, 1H), 3.08 (s, 3H), 2.06 (s, 3H), 1.34 (d, J=7.2 Hz, 3H).

Example 22: 8-Chloro-1-(2,6-dichloro-4-(2-hydroxy-2-methylpropoxy)phenyl)-2-methyl-5-(3-(methylsulfonyl)propyl)-1,6-naphthyridin-4(1H)-one (Compound C-22)

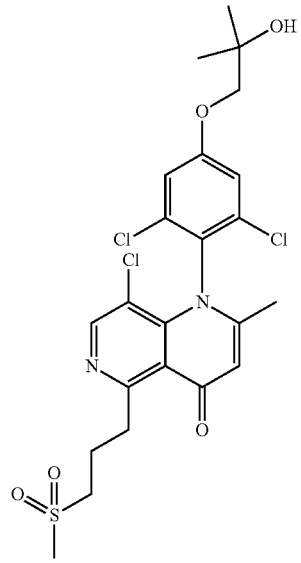 [SMILES: Cc1cc(=O)c2c(CCCS(C)(=O)=O)ncc(Cl)c2n1-c1c(Cl)cc(OCC(C)(C)O)cc1Cl]

Step 1: 8-Chloro-1-(2,6-dichloro-4-fluorophenyl)-2-methyl-5-(3-(methylthio)propyl)-1,6-naphthyridin-4(1H)-one To a sealed vial charged with allyl(methyl)sulfane (0.202 mL, 1.837 mmol) in 3 mL THF under N$_2$ was added 9-BBN (0.5M in THF) (3.98 mL, 1.990 mmol) dropwise. The mixture was stirred at room temperature for 16 hours. To a flask charged with 5,8-dichloro-1-(2,6-dichloro-4-fluorophenyl)-2-methyl-1,6-naphthyridin-4(1H)-one (intermediate F1, 600 mg, 1.530 mmol), K$_3$PO$_4$ (2.0 M) (1.530 mL, 3.06 mmol), and Pd(PPh$_3$)$_4$ (177 mg, 0.153 mmol) in DMF (15 mL) under N$_2$ was added above solution by syringe. The reaction mixture was heated to 80° C. under N$_2$ for 2 hours. Then it was allowed to cool down to room temperature, diluted with EtOAc and washed with water. The aqueous layer was extracted with EtOAc. Combined organic layers were dried over anhydrous Na$_2$SO$_4$, filtered and concentrated under reduced pressure to provide crude title compound. This was used on next step without purification. ESI-MS m/z: 445.0 [M+H]$^+$ (Rt=1.17 min, LC-method 7).

Step 2: 8-Chloro-1-(2,6-dichloro-4-fluorophenyl)-2-methyl-5-(3-(methylsulfonyl)propyl)-1,6-naphthyridin-4(1H)-one To a solution of Oxone (1881 mg, 3.06 mmol) in H$_2$O (50 mL) and MeOH (25 mL) was added 8-chloro-1-(2,6-dichloro-4-fluorophenyl)-2-methyl-5-(3-(methylthio)propyl)-1,6-naphthyridin-4(1H)-one (682 mg, 1.53 mmol) in MeOH (25 mL) dropwise. The mixture was stirred at 23° C. for 4 hours. Then it was concentrated under the reduced pressure to around 50 mL and extracted with EtOAc three times. The combined organic layers were concentrated and purified by flash column 0-100% EtOAc/heptane to provide the title compound. ESI-MS m/z: 476.9 [M+H]$^+$ (Rt=0.94 min, LC-method 7).

Step 3: 8-Chloro-1-(2,6-dichloro-4-(2-hydroxy-2-methylpropoxy)phenyl)-2-methyl-5-(3-(methylsulfonyl)propyl)-1,6-naphthyridin-4(1H)-one To a solution of 2-methylpropane-1,2-diol (113 mg, 1.256 mmol) and 8-chloro-1-(2,6-dichloro-4-fluorophenyl)-2-methyl-5-(3-(methylsulfonyl)propyl)-1,6-naphthyridin-4(1H)-one (200 mg, 0.419 mmol) in DMF (4 mL) was added Cs$_2$CO$_3$ (409 mg, 1.256 mmol). The reaction mixture was stirred at 50° C. for 16 hours. Then it was allowed to cool down to room temperature, diluted with MeOH and filtered. The filtrate was purified by HPLC to provide the title compound. C-22: ESI-MS m/z: 547.3 [M+H]$^+$ (Rt=0.91 min, LC-method 7), $^1$H NMR (400 MHz, METHANOL-d4) δ ppm=8.54 (s, 1H), 7.30 (s, 2H), 6.56 (s, 1H), 3.94 (s, 2H), 3.65-3.58 (m, 2H), 3.32-3.24 (m, 2H), 3.01 (s, 3H), 2.35-2.22 (m, 2H), 2.07 (s, 3H), 1.36 (s, 6H).

Example 23: GIRK1/4 Activity Assay

The GIRK1/4 activity of a compound according to the present invention was assessed by the following in vitro method.
Buffers:
 a. External buffer: 10 mM NaCl, 50 mM Na Gluconate, 80 mM K Gluconate, 1.8 mM CaCl$_2$, 1 mM MgCl$_2$, 10 mM HEPES, 10 mM Glucose, pH 7.4; osmolarity 300-310 Osm/L.
 b. Internal buffer: 30 mM KCl, 100 mM K Gluconate, 1 mM MgCl$_2$, 10 mM HEPES, 1 mM EGTA, 10 mM NaCl, pH 7.2; osmolarity 284-292 Osm/L.
Compounds:
 c. Prepare seven-fold compound dilution series (10 mM to 20 uM) in 100% DMSO, in 384-well polypropylene plates.
 d. Propafenone (Sigma Aldrich, catalog number P4670) was used as a positive control and DMSO for neutral control
 e. Resuspend 1 µl of compounds in DMSO into 66.7 µl external buffer in 384-well polypropylene plate and load into Plate 1 section of Molecular Devices Quattro®
Quattro Setup:
 f. Load 384-well Population Patch Plate (Molecular Devices #9000-0902) into Quattro
 g. Fill Quattro F-soak trough with 20% DMSO and 50% EtOH
 h. Fill Quattro buffer trough with external buffer
 i. Attach internal buffer flask to Quattro internal buffer tubing
 j. Attach PBS (Phosphate Buffered Saline, minus Ca$^{++}$ and Mg$^{++}$, pH7.4) bottle to F-head & E-head wash on Quattro
Antibiotic:
 k. Resuspend 5.1-5.8 mg amphotericin B (Sigma Aldrich, catalog number A2411) in 175 µl DMSO
 l. Add the resulting solution to 50 mL internal buffer and attach to antibiotic tubing port on Quattro
Cells:
 m. Use GIRK1/4 HEK293 stable cells (obtained from ChanTest, 14656 Neo Parkway, Cleveland, Ohio 44128) grown to ~80% confluency in the following cell culture medium: DMEM containing 10% (v/v) Fetal Bovine Serum, Penicillin/Streptomycin (at "IX" concentration from a 100× stock), 0.5 mg/mL G418 and 0.1 mg/mL Zeocin.
 n. Detach cells using Detachin (Genlantis, 11011 Torreyana, San Diego, CA 92121), washed with PBS (minus Ca$^{++}$ and Mg$^{++}$) and resuspend in external buffer (5 mL final volume at 2.0-2.1×10$^6$ cells/mL)
 o. Load into cell trough of Quattro
Assay Protocol:
Quattro was controlled using IonWorks v2 software to perform the following steps:
 p. Added 3.5 µl cells plus 3.5 µl external buffer to wells of Quattro Patch Plate®
 q. Circulated amphotericin B and internal buffer onto cells
 r. Applied the following voltage protocol: Pulse 1: 15 mV for 300 milliseconds (ms), followed by Pulse 2: −120 mV for 400 ms, then Pulse 3: −15 mV for 400 ms, and finally Pulse 4: −120 mV to 40 mV over 500 ms (this is a voltage ramp).
 s. Measured magnitude of inward potassium current at time point between 1200-1220 ms from start of Pulse 1 (i.e., during the voltage ramp phase).
 t. Added 3.5 µl of diluted compounds (or DMSO) to wells and repeated steps c-d (final compound concentrations are 50 uM to 0.1 uM, and each concentration was tested in quadruplicate—i.e., in 4 separate wells).
 u. The difference between current magnitude pre vs. post-compound gave a measure of GIRK1/4 inhibition.
Data Analysis:
IC$_{50}$ values were calculated by plotting the percentage of current inhibition (normalized to the DMSO-only control) as a function of compound concentration using standard data analysis software.

Using the test assay as described above compounds of the invention exhibit inhibitory activity in accordance to Table 5, provided infra.

Example 24: Pharmacokinetic Properties

The pharmacokinetic properties of the compounds in rats were assessed by the following in vivo studies as described below.

Animals

| | |
|---|---|
| Species, Strain, Gender | Rat, Spargue Dawley/CD, male |
| Age/Body weight | 8-10 weeks/240-320 grams |
| Animal model | Double jugular vein cannulated |
| No of animals | 3 rats/dose/route for discrete (non-crossover) study. In case of crossover study n = 3 for both IV and PO arms. |
| Housing | Animals were housed three per cage before surgery, in polypropylene cages (864 sq. cm floor, 18 cm height) containing irradiated corncob bedding material along with paper cuttings. Over the duration of the study, the temperature was maintained between 22 ± 3° C. and the relative humidity between 30% and 70%. 12 hour light and 12 hour dark photocycle was maintained in all rooms using automated timers. |
| Feeding/Water | The animals had free access to food and water throughout the entire experiment. |

Animal Model

At least four days before first drug administration, the rats (250-350 g) were anesthetized and, under aseptic conditions, catheters were surgically implanted into the left and right jugular veins (one for blood collection and the other one for intravenous injection). The catheters were exteriorized and fixed at the neck. For analgesic treatment, animals received analgesics before surgery and subsequently twice at appropriate times after surgery. The freely-moving animals equipped with catheters are kept individually in Macrolon cages, with free access to food and water throughout the experiment. After a recovery phase of at least 4 days, a single test compound was administered intravenously or orally, based upon the individual body weights.

Experimental Conditions

Body Weight

Rats were weighed prior to dose administration and the weight was recorded in raw data file.

Formulation

Intravenous Administration

The test articles were administered as solution in NMP:PEG 200 (10:90 v/v). Test articles where no solution can be obtained were rejected and not used in discrete or cassette dosing.

Oral Administration

The test article were administered as suspension in MC:Tween 80:water (0.5:0.1:99.4 w/v/v).

Dosing Regimen

Intravenous Administration

The test article was administered as solution and as a bolus injection or as short I.V. infusion (30 seconds) via the left jugular vein catheter to conscious rats. The dose volume was 0.5 mL/kg body weight.

The exact start and end time of dosing and exact dose volume was noted. A plastic syringe and/or a plastic infusion line was used.

Oral Administration

The test article was administered as a solution or suspension into the esophagus via a gavage tube to conscious rats. The dose volume was 5 mL/kg body weight. The exact start time of dosing and exact dose volume was noted.

Grouping, Route of Administration and Target Doses

| Study design | Group | No. of animals | Animal identification | Route of administration | Dose (mg/kg) |
|---|---|---|---|---|---|
| Discrete (non-crossover) | I | 3 | 1-3 | Intravenous | 0.3-1 |
| | II | 3 | 4-6 | Oral | 3 |

-continued

| Study design | Group | No. of animals | Animal identification | Route of administration | Dose (mg/kg) |
|---|---|---|---|---|---|
| Crossover | I | 3 | 1-3 | Intravenous and Oral | 0.3-1 (IV) 3 (PO) |

Doses for Discrete and Cassette Study

| Species | Use for discrete study | Use for cassette study | Route of administration | IV Dose per compound (mg/kg) | PO dose per compound (mg/kg) |
|---|---|---|---|---|---|
| Rat | Yes | Yes | IV | 0.3 | NA |
| Rat | Yes | No | IV | 1 | NA |
| Rat | Yes | Yes | PO | NA | 3 |
| Rat | Yes | Yes | IV/PO | 0.3 | 3 |
| Rat | Yes | No | IV/PO | 1 | 3 |

Clinical Signs

Animals were checked before and following dosing and any clinical signs observed were recorded.

Sampling Collection

Blood samples (20 µL) were collected from the right jugular vein catheter of cannulated animals (if JV catheter becomes non patent during the PK experiment (i.e., after dosing), blood can exceptionally be collected by tail vein puncture but it must be clearly specified into the in-life observations and data study rep) in tubes containing 10% of blood of 2% W/V K2 EDTA (2.0 mg/mL) at the different time intervals. Blood was collected following IV dosing at 0.083, 0.25, 0.5, 1, 2, 4, 7 and 24 h post dose. Blood was collected following PO dosing: 0.25, 0.5, 1, 2, 4, 7 and 24 h post dose.

It is important that the exact dosing and sampling times were recorded. Time points can be changed as and when required with proper justification. After the last sampling time, the rats were euthanized by $CO_2$.

The blood samples were immediately be placed on ice, and frozen to −20° C. or lower and stored until analyzed. The tubes were kept in plastic bag/Storage rack pre-labeled with name of the compound, sample number study number, route of administration, time points and date.

Bioanalysis

Bioanalysis of Formulation

An aliquot of each dosing formulation were sampled, diluted appropriately and analyzed for drug concentration. The observed concentration were scaled by the dilution factor to determine the final concentration.

Bioanalysis of Blood Samples

The concentrations of compounds in whole blood were quantified using a liquid chromatography/mass spectrometry (LC-MS/MS) assay. 20 µL of each blood sample were precipitated with 100 µL of acetonitrile containing generic internal standards (carbamazepine/telmisartan/verapamil; c=50 ng/mL). The samples were vortexed thoroughly then centrifuged (5 min, 4° C.). The supernatant (80 µL) was transferred to a clean 96-well plate and mixed with 80 µL of water.

The samples were injected (1 to 20 µL) onto suitable analytical columns, using various isocratic methods and flow rates. Mobile phases typically consisting of 0.1% formic acid in water (solvent A) and 0.1% formic acid in acetonitrile (solvent B) with additional modifiers, if needed. Compounds and the internal standards were eluted at various retention times. The HPLC systems were interfaced to mass spectrometers. MS/MS analyses were carried out using electrospray ionization (ESI), typically in the positive ionization mode. Compounds and the internal standards were monitored using multiple reaction monitoring (MRM).

The standard curves employed for sample quantitation ranged over several log units. The lower limit of quantitation (LLOQ) in blood was determined and used as cutoff for the analytical sensitivity. Known amounts of the compounds were spiked into blood to create quality control samples with six known concentrations in singlets. The accuracy of the in vivo blood sample concentration determination was considered acceptable when the intra-assay accuracies obtained for the quality control samples were within 70% to 130% of the expected concentrations. Subsequently, from the time concentration data, pharmacokinetic parameters were calculated by non-compartmental regression analyses using an in house fitting program.

Pharmacokinetic Analysis

From the time concentration data, pharmacokinetic parameters were calculated by non-compartmental regression analyses using an in house fitting program.

| AUClast (nM*h) | AUClast refers to the area under the concentration versus time curve from t = 0 to tlast. This data was calculated from t = 0 to Tlast using either the linear trapezoidal rule, the log-linear trapezoidal rule (when the decay between the time points is mono-exponential) or a combination of both. The choice of the method was thus up to the discretion of the PK analyst (e.g., MAP PTM). |
|---|---|
| CL (mL/min/kg) | The clearance, CL, was calculated as Dose/AUCinf following IV dosing. |
| F (%) | The extravascular bioavailability, F, was preferably calculated as the dose normalized ratio of extravascular AUCinf to intravenous AUCinf. As an example, for a substance dosed orally: F = [AUCinfPO/PO dose]/[IV AUCinfIV/IV dose] × 100% For studies with crossover design, F was calculated for each animal. For studies with serial sampling but no crossover design, the mean intravenous AUCinf was used to calculate bioavailability for each animal dosed by the extravascular route. If AUCinf is not available (either because λz is not defined or because the AUC extrapolation to infinite exceeded 25% of AUCinf), then AUClast was substituted for AUCinf in the calculation. |

TABLE 5

Inhibitory activity and pharmacokinetic properties in rats

| Example | GIRK¼ IC$_{50}$ (µM) | Rat Cl (mL/min/kg) | Rat AUC$_{0-24\,h}$ 3 mg/kg (nMh) | Rat F (%) |
|---|---|---|---|---|
| 1 | 0.09 | 20.2 | 3270 | 71 |
| 2 | 0.22 | 23.0 | 1288 | 29 |
| 3 | 0.22 | 5.7 | 7738 | 47 |
| 4 | 0.16 | 5.5 | 3674 | 22 |
| 5 | 0.06 | 14.6 | 2336 | 33 |
| 6 | 0.13 | 21.6 | 3570 | 82 |
| 7 | 0.07 | 13.6 | 4410 | 61 |
| 8 | 0.07 | n/a | n/a | n/a |
| 9 | 0.08 | 24.2 | 1460 | 40 |
| 10 | 0.33 | n/a | n/a | n/a |
| 11 | 0.16 | n/a | n/a | n/a |
| 12 | 0.20 | n/a | n/a | n/a |
| 13 | 0.06 | 18.4 | 2410 | 55 |
| 14 | 0.17 | n/a | n/a | n/a |
| 15 | 0.32 | 32.8 | 1290 | 46 |
| 16 | 0.03 | n/a | n/a | n/a |
| 17 | 0.25 | 31.7 | 2310 | 73 |
| 18 | 0.03 | 38.9 | 1702 | 65 |
| 19 | 0.05 | 27.9 | 1290 | 46 |
| 20 | 0.05 | 19.8 | 2407 | 44 |
| 21 | 0.17 | 10.4 | 3200 | 34 |
| 22 | 0.19 | 23.6 | 1360 | 37 |

A pharmacokinetic study of the compound of Example 1 in male Beagle dogs dosing 0.3 mg/kg IV as a solution and 1 mg/kg PO as a suspension resulted in the following PK parameters:

Clearance (Cl): 5.5 mL/min/kg;

AUC$_{0-24\,h}$: 5270 nMh; and

Oral bioavailability (F): 87%.

The low to moderate clearance and good oral bioavailability observed in both rats and dogs for the compounds of formula (I) according to the invention, especially for the compound of Example 1, is in line with an oral administration regimen in humans.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of formula (I):

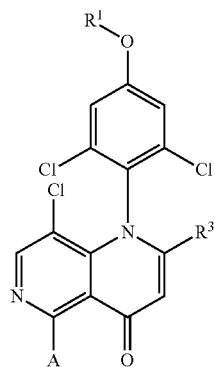

or a pharmaceutically acceptable salt thereof, wherein
$R^1$ is $(C_1-C_6)$alkyl substituted with one or more substituents independently selected from —OH, —C(O)NHRa and a 4- to 6-membered heterocycle which is optionally substituted with one or more —OH;
A is —OR$^2$ or $(C_1-C_6)$alkyl optionally substituted with one or more substituents independently selected from —SO$_2$(C$_1$-C$_4$)alkyl, —NHC(O)R$^b$, and —C(O)NHR$^c$;
$R^2$ is $(C_1-C_6)$alkyl substituted with one or more substituents independently selected from —NHC(O)R$^d$ and —C(O)NHR$^e$, wherein the $(C_1-C_6)$alkyl is further optionally substituted with one or more substituents independently selected from halo, —OH and —CN;
$R^a$, $R^b$, $R^c$, $R^d$, and $R^e$ are each independently selected from H and $(C_1-C_6)$alkyl optionally substituted with one or more —OH; and
$R^3$ is $(C_1-C_4)$alkyl.

2. A compound according to claim 1 or a pharmaceutically acceptable salt thereof, wherein $R^1$ is selected from

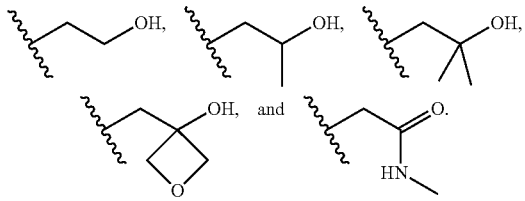

3. A compound according to claim 1 or a pharmaceutically acceptable salt thereof, wherein A is —OR$^2$.

4. A compound according to claim 1 or a pharmaceutically acceptable salt thereof, wherein R$^e$ is selected from H and (C$_1$-C$_4$)alkyl optionally substituted with one or more —OH.

5. A compound according to claim 1 or a pharmaceutically acceptable salt thereof, wherein R$^2$ is (C$_1$-C$_4$)alkyl substituted with one or more substituents independently selected from —NHC(O)CH$_3$, —C(O)NHCH$_3$, —C(O)NHCH$_2$CH$_2$OH, and —C(O)NH$_2$, and wherein the (C$_1$-C$_4$) alkyl is further optionally substituted with one or more substituents independently selected from halo, —OH and —CN.

6. A compound according to claim 1 or a pharmaceutically acceptable salt thereof, wherein R$^2$ is selected from

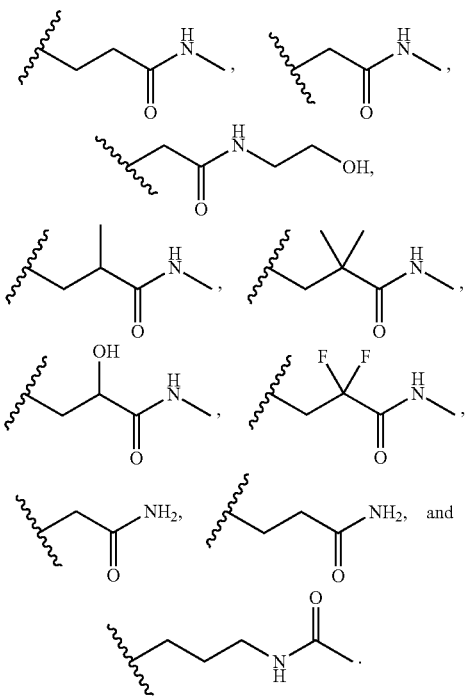

7. A compound according to claim 1 or a pharmaceutically acceptable salt thereof, wherein R$^3$ is —CH$_3$.

8. A compound according to claim 1 or a pharmaceutically acceptable salt thereof, wherein said compound is selected from the group consisting of:
3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide;
2-((8-chloro-1-(2,6-dichloro-4-(2-hydroxyethoxy)phenyl)-2-methyl-4-oxo-1,4-dihydro-1,6-naphthyridin-5-yl)oxy)-N-(2-hydroxyethyl)acetamide;
3-((8-chloro-1-(2,6-dichloro-4-(2-hydroxy-2-methylpropoxy)phenyl)-2-methyl-4-oxo-1,4-dihydro-1,6-naphthyridin-5-yl)oxy)-N-methylpropanamide;
2-((8-chloro-1-(2,6-dichloro-4-(2-hydroxy-2-methylpropoxy)phenyl)-2-methyl-4-oxo-1,4-dihydro-1,6-naphthyridin-5-yl)oxy)-N-methylacetamide;
2-((8-chloro-1-(2,6-dichloro-4-(2-hydroxyethoxy)phenyl)-2-methyl-4-oxo-1,4-dihydro-1,6-naphthyridin-5-yl)oxy)-N-methylacetamide;
(R)-3-((8-chloro-1-(2,6-dichloro-4-(2-hydroxypropoxy)phenyl)-2-methyl-4-oxo-1,4-dihydro-1,6-naphthyridin-5-yl)oxy)-N-methylpropanamide;
(R)-3-((8-chloro-1-(2,6-dichloro-4-(2-hydroxyethoxy)phenyl)-2-methyl-4-oxo-1,4-dihydro-1,6-naphthyridin-5-yl)oxy)-N,2-dimethylpropanamide;
(S)-3-((8-chloro-1-(2,6-dichloro-4-(2-hydroxyethoxy)phenyl)-2-methyl-4-oxo-1,4-dihydro-1,6-naphthyridin-5-yl)oxy)-N,2-dimethylpropanamide;
N-(2-((8-chloro-1-(2,6-dichloro-4-(2-hydroxyethoxy)phenyl)-2-methyl-4-oxo-1,4-dihydro-1,6-naphthyridin-5-yl)oxy)ethyl)acetamide;
(S)-3-((8-chloro-1-(2,6-dichloro-4-(2-hydroxypropoxy)phenyl)-2-methyl-4-oxo-1,4-dihydro-1,6-naphthyridin-5-yl)oxy)-N-methylpropanamide;
3-((8-chloro-1-(2,6-dichloro-4-(2-hydroxyethoxy)phenyl)-2-methyl-4-oxo-1,4-dihydro-1,6-naphthyridin-5-yl)oxy)-N,2,2-trimethylpropanamide;

(R)-3-((8-chloro-1-(2,6-dichloro-4-(2-hydroxyethoxy)phenyl)-2-methyl-4-oxo-1,4-dihydro-1,6-naphthyridin-5-yl)oxy)-2-hydroxy-N-methylpropanamide;

(S)-3-((8-chloro-1-(2,6-dichloro-4-(2-hydroxyethoxy)phenyl)-2-methyl-4-oxo-1,4-dihydro-1,6-naphthyridin-5-yl)oxy)-2-hydroxy-N-methylpropanamide;

(S)-3-((8-chloro-1-(2,6-dichloro-4-(2-hydroxy-2-methylpropoxy)phenyl)-2-methyl-4-oxo-1,4-dihydro-1,6-naphthyridin-5-yl)oxy)-2-hydroxy-N-methylpropanamide;

3-((8-chloro-1-(2,6-dichloro-4-((3-hydroxyoxetan-3-yl)methoxy)phenyl)-2-methyl-4-oxo-1,4-dihydro-1,6-naphthyridin-5-yl)oxy)-N-methylpropanamide;

3-((8-chloro-1-(2,6-dichloro-4-(2-hydroxyethoxy)phenyl)-2-methyl-4-oxo-1,4-dihydro-1,6-naphthyridin-5-yl)oxy)-2,2-difluoro-N-methylpropanamide;

2-(4-(5-(2-amino-2-oxoethoxy)-8-chloro-2-methyl-4-oxo-1,6-naphthyridin-1(4H)-yl)-3,5-dichlorophenoxy)-N-methylacetamide;

3-((8-chloro-1-(2,6-dichloro-4-(2-hydroxyethoxy)phenyl)-2-methyl-4-oxo-1,4-dihydro-1,6-naphthyridin-5-yl)oxy)propanamide;

N-(3-(8-chloro-1-(2,6-dichloro-4-(2-hydroxyethoxy)phenyl)-2-methyl-4-oxo-1,4-dihydro-1,6-naphthyridin-5-yl)propyl)acetamide;

8-chloro-1-(2,6-dichloro-4-(2-hydroxyethoxy)phenyl)-2-methyl-5-(2-(methylsulfonyl)ethyl)-1,6-naphthyridin-4(1H)-one;

8-chloro-1-(2,6-dichloro-4-(2-hydroxyethoxy)phenyl)-2-methyl-5-(2-(methylsulfonyl)propyl)-1,6-naphthyridin-4(1H)-one; and 8-chloro-1-(2,6-dichloro-4-(2-hydroxy-2-methylpropoxy)phenyl)-2-methyl-5-(3-(methylsulfonyl)propyl)-1,6-naphthyridin-4(1H)-one.

9. A compound according to claim 1 or a pharmaceutically acceptable salt thereof, wherein said compound is in a crystalline form selected from a free form, a hydrate, a solvate, a polymorph and a co-crystal thereof.

10. A compound according to claim 9, wherein said compound is 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide in a crystalline form selected from:

(i) a free crystalline form named Modification A-1, characterized in that said crystalline form has an X-ray powder diffraction pattern comprising four or more 2θ values (+0.1 degree), when measured using a CuKα radiation with a wavelength of 1.5418 Å at a temperature of about 22° C., selected from 7.7, 11.3, 15.4, 16.4, 17.7, 21.2, 22.7, 23.3, 24.0, 26.4 and 27.2;

(ii) a hydrate crystalline form named Modification A-2, characterized in that said crystalline form has an X-ray powder diffraction pattern comprising four or more 2θ values (+0.1 degree), when measured using a CuKα radiation with a wavelength of 1.5418 Å at a temperature of about 22° C., selected from 7.6, 10.7, 15.2, 16.9, 21.4, 24.0, 25.8, 27.4, and 30.7;

(iii) a hydrate crystalline form named Modification A-3, characterized in that said crystalline form has an X-ray powder diffraction pattern comprising four or more 2θ values (+0.1 degree), when measured using a CuKα radiation with a wavelength of 1.5418 Å at a temperature of about 22° C., selected from 7.6, 15.3, 17.0, 20.7, 21.4, 22.2, 25.9, 29.1, and 32.3;

(iv) a hydrate crystalline form named Modification A-4, characterized in that said crystalline form has an X-ray powder diffraction pattern comprising four or more 2θ values (+0.1 degree), when measured using a CuKα radiation with a wavelength of 1.5418 Å at a temperature of about 22° C., selected from 7.3, 10.3, 15.5, 22.1, 23.1, 23.9, 25.5, 25.9, 26.4, and 31.2; and (v) a hydrate crystalline form named Modification A-5, characterized in that said crystalline form has an X-ray powder diffraction pattern comprising four or more 2θ values (+0.1 degree), when measured using a CuKα radiation with a wavelength of 1.5418 Å at a temperature of about 22° C., selected from 5.0, 9.9, 14.9, 15.9, 17.7, 19.8, 24.0, 25.5, and 27.2.

11. A compound according to claim 1 or a pharmaceutically acceptable salt thereof, wherein the compound is 3-((8-chloro-1-(2,6-dichloro-4-(2-hydroxyethoxy)phenyl)-2-methyl-4-oxo-1,4-dihydro-1,6-naphthyridin-5-yl)oxy)-N,2,2-trimethylpropanamide.

12. A compound according to claim 1 or a pharmaceutically acceptable salt thereof, wherein the compound is 3-((8-chloro-1-(2,6-dichloro-4-(2-hydroxyethoxy)phenyl)-2-methyl-4-oxo-1,4-dihydro-1,6-naphthyridin-5-yl)oxy)-N-methylpropanamide.

13. A compound according to claim 1 or a pharmaceutically acceptable salt thereof, wherein the compound is 2-((8-chloro-1-(2,6-dichloro-4-(2-hydroxyethoxy)phenyl)-2-methyl-4-oxo-1,4-dihydro-1,6-naphthyridin-5-yl)oxy)-N-methylacetamide.

14. A compound according to claim 1 or a pharmaceutically acceptable salt thereof, wherein the compound is N-(3-(8-chloro-1-(2,6-dichloro-4-(2-hydroxyethoxy)phenyl)-2-methyl-4-oxo-1,4-dihydro-1,6-naphthyridin-5-yl)propyl)acetamide.

15. A pharmaceutical composition comprising a compound according to claim 1 or a pharmaceutically acceptable salt thereof and one or more pharmaceutically acceptable carriers.

16. The pharmaceutical composition according to claim 15, further comprising at least one additional pharmaceutically active agent selected from Class I antiarrhythmic agents, Class II antiarrhythmic agents, Class III antiarrhythmic agents, Class IV antiarrhythmic agents, Class V antiarrhythmic agents, cardiac glycosides and other drugs affecting atrial refractoriness; haemostasis modulators, antithrombotics; thrombin inhibitors; factor VIIa inhibitors; anticoagulants, factor Xa inhibitors, and direct thrombin inhibitors; antiplatelet agents, cyclooxygenase inhibitors, adenosine diphosphate (ADP) receptor inhibitors, phosphodiesterase inhibitors, glycoprotein IIB/IIA, adenosine reuptake inhibitors; anti-dyslipidemia agents, HMG-CoA reductase inhibitors, other cholesterol-lowering agents; bile acid sequestrants; cholesterol absorption inhibitors; cholesteryl ester transfer protein (CETP) inhibitors; inhibitors of the ileal bile acid transport system (IBAT inhibitors); bile acid binding resins; nicotinic acid and analogues thereof; anti-oxidants; omega-3 fatty acids; antihypertensive agents, including adrenergic receptor antagonists, beta blockers, alpha blockers, mixed alpha/beta blockers; adrenergic receptor agonists, alpha-2 agonists; angiotensin converting enzyme (ACE) inhibitors, calcium channel blockers; angiotensin II receptor antagonists; aldosterone receptor antagonists; centrally acting adrenergic drugs, central alpha agonists; and diuretic agents; anti-obesity agents, pancreatic lipase inhibitors, microsomal transfer protein (MTP) modulators, diacyl glycerolacyltransferase (DGAT) inhibitors, cannabinoid (CBI) receptor antagonists; insulin and insulin analogues; insulin secretagogues; agents that improve incretin action, dipeptidyl peptidase IV (DPP-4) inhibitors, glucagon-like peptide-I (GLP-1) agonists; insulin sensitizing agents, peroxisome proliferator activated receptor gamma (PPARγ) agonists, agents that modulate hepatic glucose balance, fructose 1,6-bisphosphatase inhibitors, glycogen phosphorylase inhibitors, glycogen synthase kinase inhibitors, glucokinase activators; agents designed to reduce/slow the absorption of glucose from the intestine, alpha-glucosidase inhibitors; agents which antagonize the actions of or reduce secretion of glucagon, amylin analogues; agents that prevent the reabsorption of glucose by the kidney, and sodium-dependent glucose transporter 2 (SGLT-2) inhibitors.

17. A method for treating or preventing a disease or disorder comprising administering to a patient in need thereof a therapeutically effective amount of a compound according claim 1, wherein the disease or disorder is selected from cardiac arrhythmia, atrial fibrillation, bradyarrhythmia, bradycardia, heart block, sick sinus syndrome, parasympathetic hyperactivation, primary hyperaldosteronism, hypotension, and vasovagal syncope.

18. A method for maintaining a sinus rhythm after cardioversion in a patient with persistent or recent onset of atrial fibrillation or preventing a recurrence in a patient with paroxysmal atrial fibrillation, the method comprising administering to a patient in need thereof a therapeutically effective amount of a compound according to claim 1.

19. The method according to claim 17, wherein administering the compound is orally.

20. A method for treating or preventing a disease or disorder comprising administering to a patient in need thereof a therapeutically effective amount of a pharmaceutical composition according claim 15, wherein the disease or disorder is selected from cardiac arrhythmia, atrial fibrillation, bradyarrhythmia, bradycardia, heart block, sick sinus syndrome, parasympathetic hyperactivation, primary hyperaldosteronism, hypotension, and vasovagal syncope.

21. A method for maintaining a sinus rhythm after cardioversion in a patient with persistent or recent onset of atrial fibrillation or preventing a recurrence in a patient with paroxysmal atrial fibrillation, the method comprising administering to a patient in need thereof a therapeutically effective amount of a pharmaceutical composition according claim 15.

\* \* \* \* \*